United States Patent
Yu et al.

(10) Patent No.: US 9,655,552 B2
(45) Date of Patent: May 23, 2017

(54) DEVICES FOR DETECTING OR FILTERING TUMOR CELLS

(71) Applicants: Chris C. Yu, Conneautville, PA (US); Xuedong Du, Shanghai (CN); He Yu, Honolulu, HI (US)

(72) Inventors: Chris C. Yu, Conneautville, PA (US); Xuedong Du, Shanghai (CN); He Yu, Honolulu, HI (US)

(73) Assignee: Shanghai Xinshenpai Technology Co., Ltd., Shanghai (CN)

( * ) Notice: Subject to any disclaimer, the term of this patent is extended or adjusted under 35 U.S.C. 154(b) by 340 days.

(21) Appl. No.: 14/072,609

(22) Filed: Nov. 5, 2013

(65) Prior Publication Data

US 2014/0057340 A1 Feb. 27, 2014

Related U.S. Application Data

(62) Division of application No. 14/155,584, filed as application No. PCT/US2012/036551 on May 4, 2012.

(Continued)

(51) Int. Cl.
*G01N 33/00* (2006.01)
*A61B 5/145* (2006.01)
(Continued)

(52) U.S. Cl.
CPC ............ *A61B 5/14546* (2013.01); *A61B 5/07* (2013.01); *A61B 5/1451* (2013.01); *A61B 5/14503* (2013.01); *A61B 5/14517* (2013.01); *A61B 5/14528* (2013.01); *A61B 10/0041* (2013.01); *B01L 3/502707* (2013.01); *B01L 3/502761* (2013.01); *C12Q 1/68* (2013.01); *G01N 1/34* (2013.01); *G01N 1/4077* (2013.01); *G01N 15/1056* (2013.01); *G01N 15/1484* (2013.01); *G01N 33/5091* (2013.01); *G01N 33/574* (2013.01); *A61B 2562/028* (2013.01); *A61B 2562/12* (2013.01); *B01L 2200/0647* (2013.01); *B01L 2200/0652* (2013.01); *B01L 2200/0663* (2013.01); *B01L 2200/0668* (2013.01); *B01L 2300/0636* (2013.01); *B01L 2300/0645* (2013.01); *B01L 2300/0681* (2013.01); *B01L 2300/0887* (2013.01); *B01L 2300/163* (2013.01); *B01L 2400/0487* (2013.01);

(Continued)

(58) Field of Classification Search
CPC ............ B01L 3/5027; B01L 3/502707; G01N 15/1056
See application file for complete search history.

(56) References Cited

U.S. PATENT DOCUMENTS

2004/0248167 A1* 12/2004 Quake .................. B01F 5/0646
435/6.19
2007/0007133 A1* 1/2007 Mang .................. A61B 5/14532
204/403.14

(Continued)

*Primary Examiner* — Jill Warden
*Assistant Examiner* — Brittany Fisher
(74) *Attorney, Agent, or Firm* — Weisun Rao; Greenberg Traurig, LLP

(57) ABSTRACT

Among others, the present invention provides devices each including a micro-filter, a shutter, a cell counter, a selector, a micro-surgical kit, a timer, and a data processing circuitry, wherein the micro-filter is capable of detecting or filtering circulating tumor cells.

5 Claims, 68 Drawing Sheets

Related U.S. Application Data

(60) Provisional application No. 61/482,900, filed on May 5, 2011.

(51) Int. Cl.

| | |
|---|---|
| G01N 15/10 | (2006.01) |
| C12Q 1/68 | (2006.01) |
| G01N 33/50 | (2006.01) |
| G01N 1/34 | (2006.01) |
| A61B 5/07 | (2006.01) |
| B01L 3/00 | (2006.01) |
| A61B 10/00 | (2006.01) |
| G01N 1/40 | (2006.01) |
| G01N 15/14 | (2006.01) |
| G01N 33/574 | (2006.01) |
| G01N 33/543 | (2006.01) |
| G01N 15/00 | (2006.01) |

(52) U.S. Cl.
CPC ............ *G01N 33/54366* (2013.01); *G01N 2001/4088* (2013.01); *G01N 2015/0065* (2013.01); *G01N 2015/1006* (2013.01); *G01N 2015/1062* (2013.01); *G01N 2015/1486* (2013.01)

(56) References Cited

U.S. PATENT DOCUMENTS

| | | | |
|---|---|---|---|
| 2008/0248972 A1* | 10/2008 | Nishizawa | G01N 33/543 506/32 |
| 2009/0188864 A1* | 7/2009 | Zheng | B01D 61/18 210/641 |
| 2009/0282899 A1* | 11/2009 | Nam | G01N 1/2214 73/31.07 |
| 2010/0154535 A1* | 6/2010 | Manalis | G01N 9/002 73/32 R |

* cited by examiner (a)

(b)

(c)

(k)

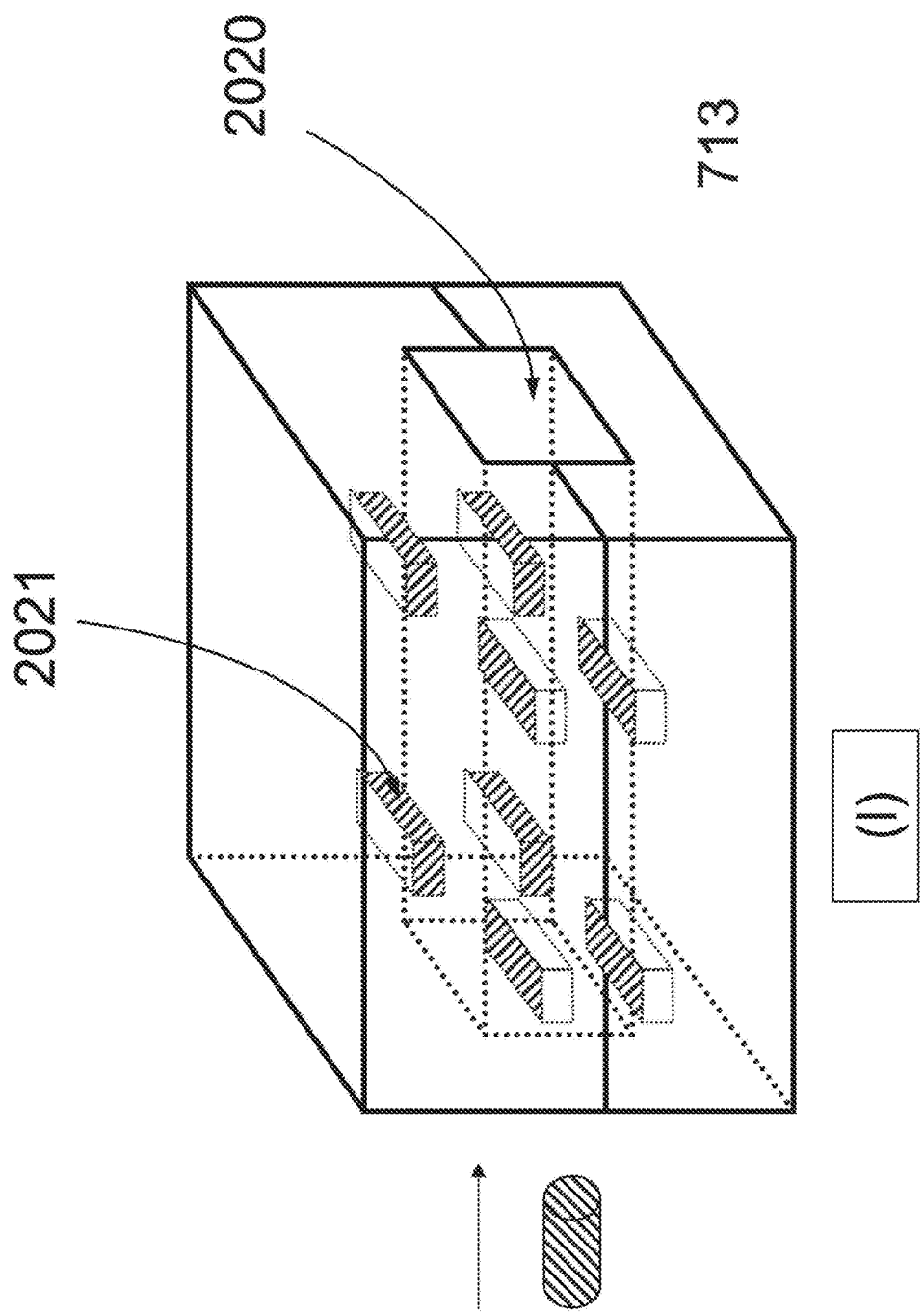

(m)

(n)

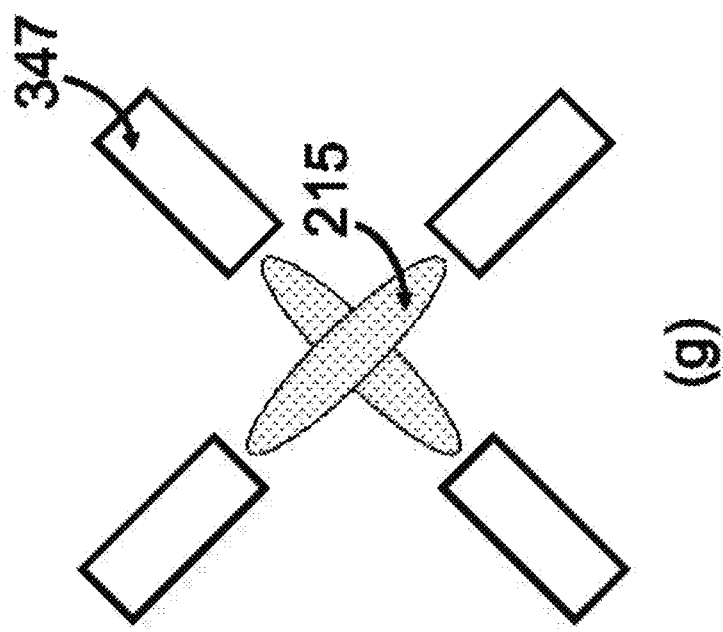
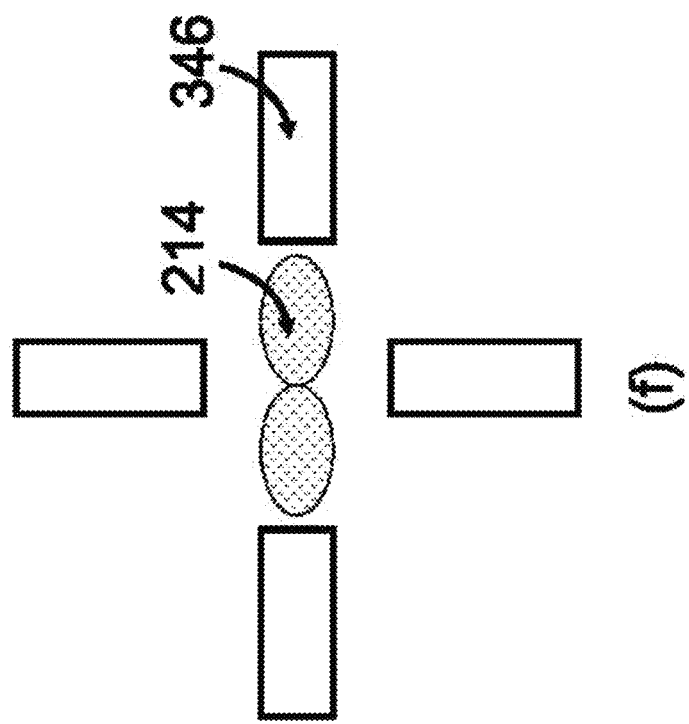
FIG. 8 (Cont.)

(r)

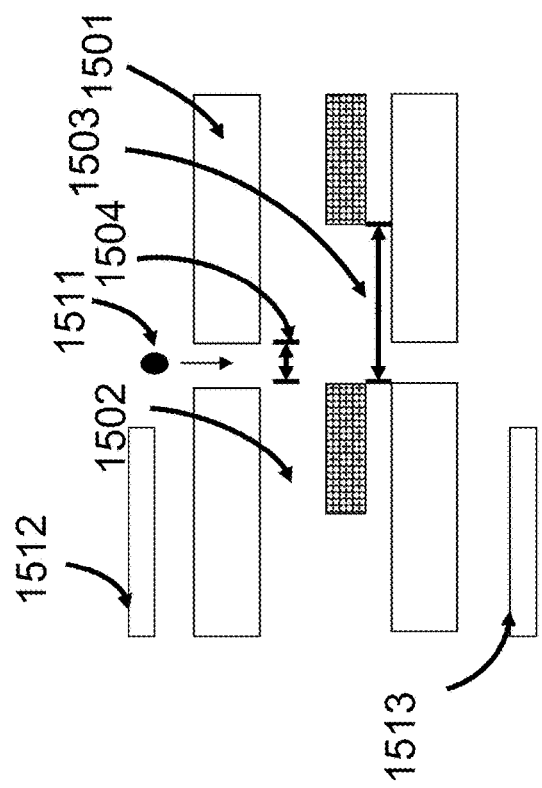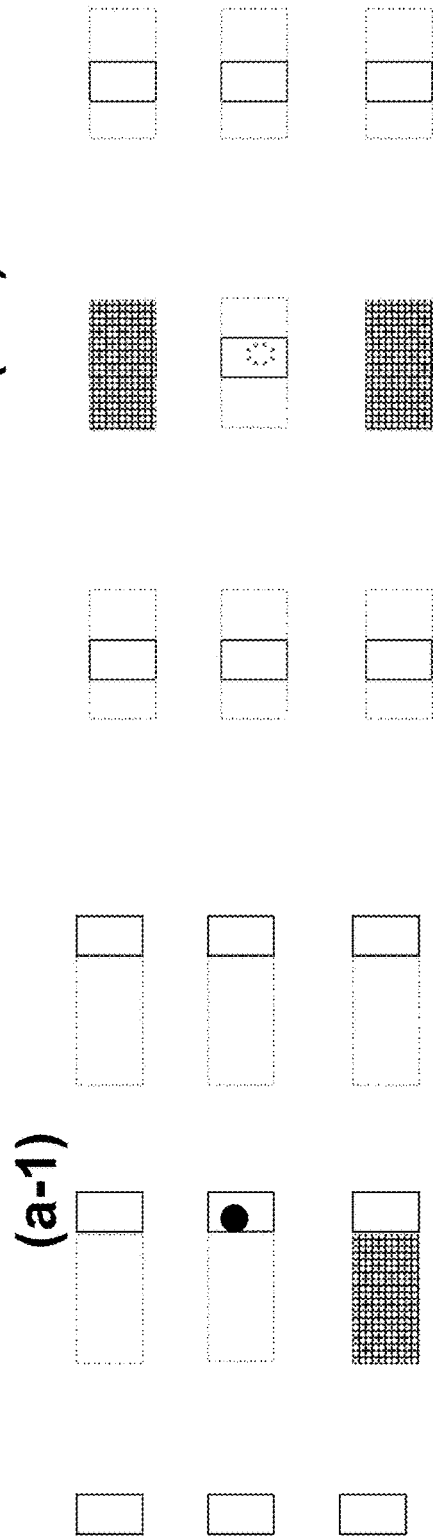
FIG. 15

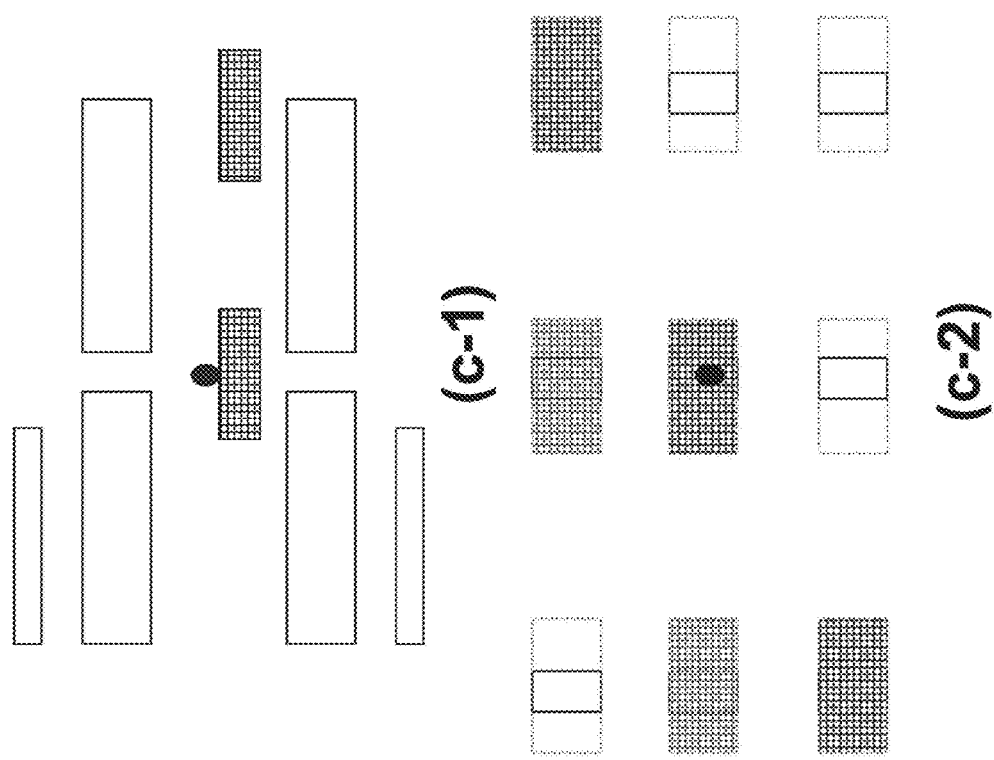

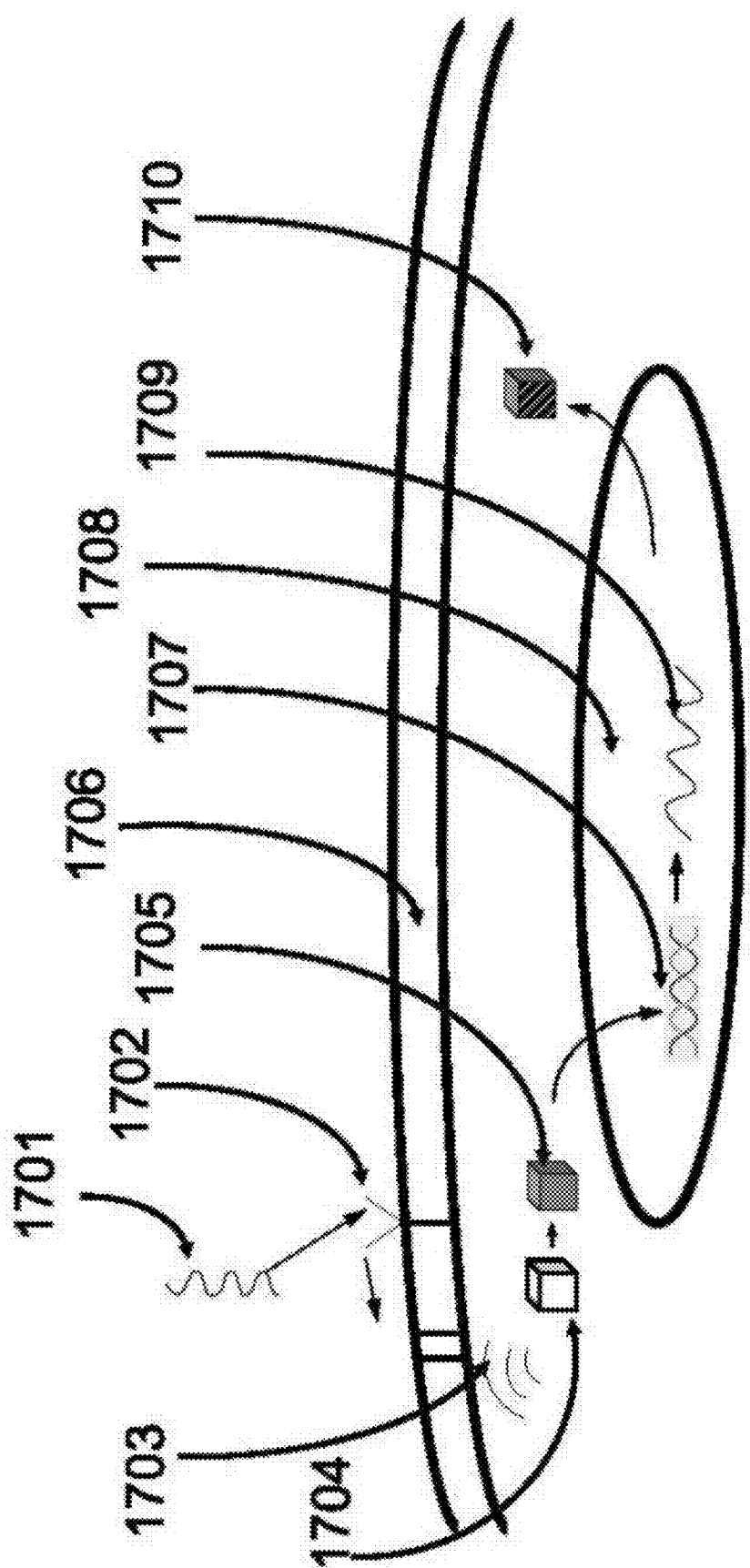
FIG. 17-a

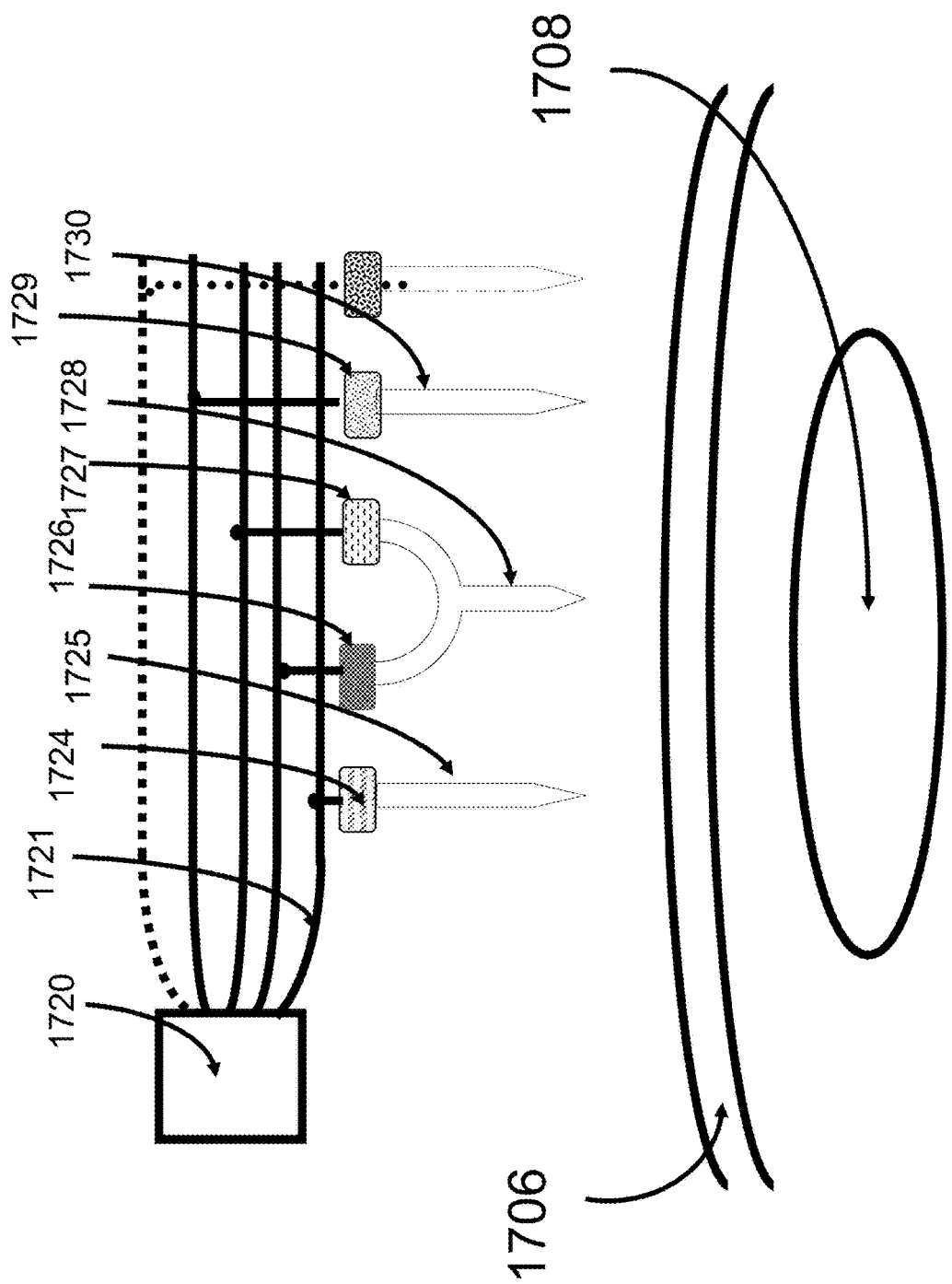
FIG. 17-b

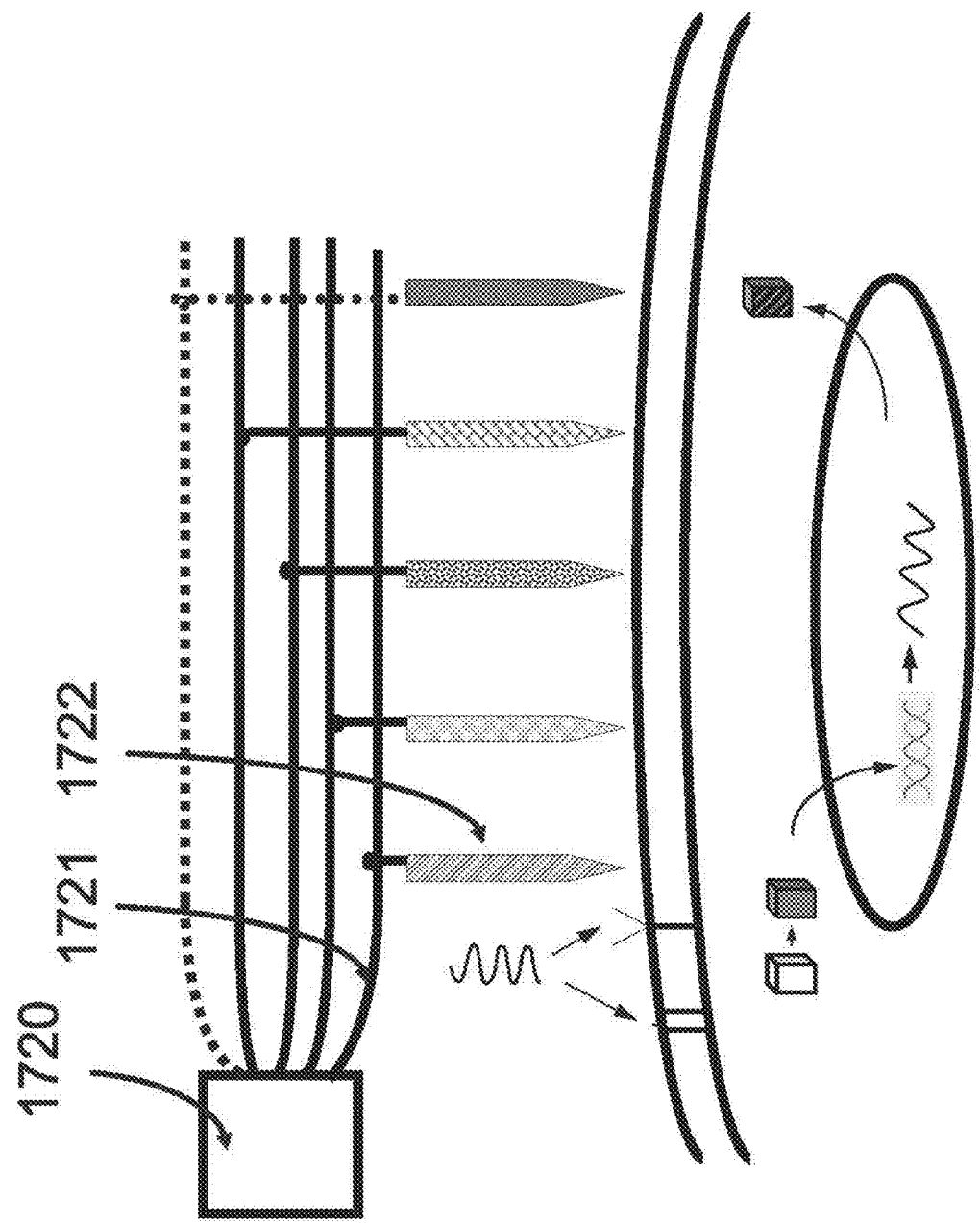

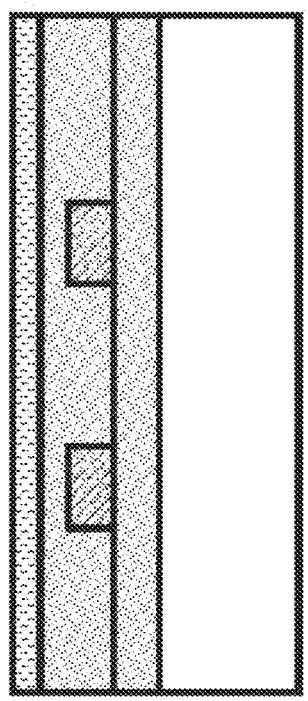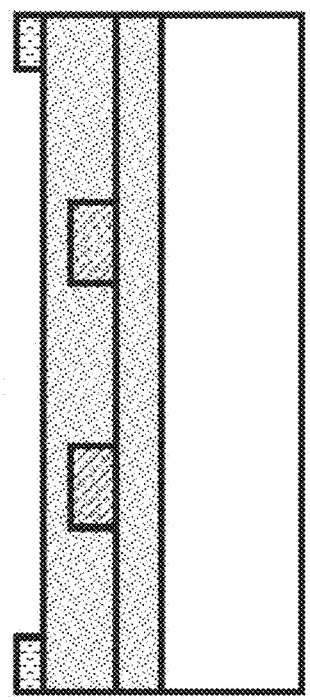
FIG. 19 (Cont.)

(c)

(a)

Detecting device covered with transparent panel (b)

DEVICES FOR DETECTING OR FILTERING TUMOR CELLS

CROSS-REFERENCE TO RELATED APPLICATIONS

This application is a divisional application of U.S. application Ser. No. 14/115,584, filed on Nov. 4, 2013, which is a U.S. national phase application and claims the benefit under 35 U.S.C. §371 of PCT/US2012/036551, filed on May 4, 2012, which in turn claims priority to U.S. Application No. 61/482,900, filed on May 5, 2011, the contents of all of which applications are incorporated herein by reference in their entireties.

BACKGROUND OF THE INVENTION

A tumor is an abnormal growth of body tissue and can be cancerous (malignant) or noncancerous (benign). Tumors, particularly cancerous tumors, are a serious threat to human well-being and their detection in early stage is critical in order to obtain effective treatment or cure. However, it is a huge challenge for conventional tumor detection methods to detect cancer earlier than symptomatically, or detect cancer at earlier stages of tumor metastasis. For example, conventional methods fail to identify about 40% of cancer patients who are in need of more or enhanced therapies. It is also important to detect any early signs of spread in cancer following cancer treatments to assess effectiveness of the treatment, as well as if and what follow-up treatment is needed. Conventional cancer detection techniques such as x-ray imaging and nuclear magnetic resonance (NMR) imaging fail to provide reliable information to the above critical applications.

Recent research and clinical studies have shown that cancer invasion to a human body may occur very early in tumor development. Early detection and early systemic therapies will result in a declining death rate from cancer. Metastasis, initiated by tumor cells transported through the circulation from the primary tumor to vital distant organs, is known to be the leading cause of cancer related deaths. The early spread of tumor cells to lymph nodes or bone marrow in peripheral blood is referred to as circulating tumor cells (CTCs or CTC). CTCs may still exist in a patient' peripheral blood even after the removal of the primary tumor.

CTCs are essential for establishing metastasis, and detection of CTCs is an important tool to assess the aggressiveness of a given tumor and its potential of subsequent growth at distant organs. Specific and sensitive detection of CTCs can be used to identify the overall cancer development or metastasis status, survival possibility, and assessment of the therapeutic response.

With more and more research on CTCs in recent years, its importance to cancer progression gets highly respected. However, CTCs exist in blood only on the order of 1 per billion to 10 billion. Present technique to separate and identify CTCs, on one hand, is quite labor intensive and expensive, and on the other hand lack accuracy and reliability. The procedure includes density gradient separation, immunomagnetic separation and density gradient immunomagnetic separation, and more hard work in dealing with the identification of the large volume filtered cells by human.

There is a pressing need to find solutions that can bring enhanced sensitivity, specificity, efficiency, convenience, and speed in early-stage CTC detection at reduced costs.

SUMMARY OF THE INVENTION

The present invention in general relates to a class of innovative methods and apparatus for detecting tumor cells, particularly circulating tumor cells (CTCs), by analyzing a biological subject (e.g., peripheral blood samples or other body fluids samples of a mammal), then diagnosing the cancer development or metastasis status thereof. It can also communicate with CTCs, and modify or correct certain aspects of CTCs. This invention utilizes novel micro-devices or an apparatus with micro-devices integrated onto it for carrying out diagnosis at microscopic levels, in vivo or in vitro, on the biological subject (e.g., fluidic samples such as blood or lymph) containing cells, (e.g., white and red blood cells, tumor cells). The apparatus can have multiple and enhanced functionalities due to the integrated micro-devices. These apparatus can be made by using state-of-the-art micro-device fabrication technologies and novel process flows such as integrated circuit fabrication technologies. Apparatus of this invention containing multiple micro-devices that can detect multiple parameters of a biological subject to be analyzed. These CTC detection apparatus are capable of detecting cancer diseases at their early stages with a high degree of sensitivity, specificity, speed, convenience (e.g., reduced equipment size), or affordability (e.g., reduced costs). Examples of cancers that can be detected by these apparatus include prostate cancer, lung cancer, colon cancer, breast cancer, brain cancer, cervical cancer, Hodgkin's lymphoma, non-Hodgkin's lymphoma, kidney cancer, leukemia, liver cancer, ovarian cancer, skin cancer, testicular cancer, thyroid cancer, pancreatic cancer, endometrial cancer, esophageal cancer, and uterine cancer.

Key component of the detection equipment is a class of novel micro-devices and their inventive fabrication process flows which enable it to perform at a much higher level than those of conventional disease detection equipments or technologies, due to much improved detection sensitivity, specificity, and speed. Examples of fabrication techniques that can be used to make the micro-devices described herein include but not limited to mechanical, chemical, chemical mechanical, electro-chemical-mechanical, electro-bio-chemical-mechanical, integrated circuit and semiconductor manufacturing techniques and processes. For a general description of some of the applicable fabrication technologies, see, e.g., R. Zaouk et al., Introduction to Microfabrication Techniques, in *Microfluidic Techniques* (S. Minteer, ed.), 2006, Humana Press; *Microsystem Engineering of Lab-on-a-chip Devices*, 1st Ed. (Geschke, Klank & Telleman, eds.), John Wiley & Sons., 2004. Micro-device functionalities would at least include sensing, detecting, measuring, diagnosing, monitoring, and analyzing for disease diagnosis. Multiple micro-devices can be integrated onto a piece of detection apparatus for further enhanced measurement sensitivity, specificity, speed and functionalities, with ability to measure the same parameter or a set of different parameters.

Optional components of the apparatus include components for addressing, controlling, forcing, receiving, amplifying, or storing information from each probe. Such components can be, e.g., a central control unit that includes a controlling circuitry, an addressing unit, an amplifier circuitry, a logic processing circuitry, a memory unit, an application specific chip, a signal transmitter, a signal receiver, a sensor, a micro-electro-mechanical device, a multi-functional device, or a micro-instrument to perform surgery, drug delivery, cleaning, or medical function.

Specifically, one aspect of this invention provides apparatus for detecting CTCs in a biological subject, each comprising a first micro-device and a first substrate supporting the first micro-device, wherein the first micro-device contacts a biological entity to be analyzed and is capable of measuring at the microscopic level an electrical, magnetic, electromagnetic, thermal, optical, fluorescent emission, radiation, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical property, or a combination thereof, of the biologic subject. The apparatus can further optionally include a device for reading the data from measuring the property.

In some embodiments, the difference in the measured property between the tested biologic subject and that of a biologic subject free of the disease (i.e., standard biological subject) or between the cells contained in the tested biological subject and normal cells is indicative of the possible existences of CTCs in the tested biological subject.

In some other embodiments, the electrical property is surface charge, surface potential, resting potential, electrical current, electrical field distribution, surface charge distribution, cell electronic properties, cell surface electronic properties, dynamic changes in electronic properties, dynamic changes in cell electronic properties, dynamic changes in cell surface electronic properties, dynamic changes in surface electronic properties, electronic properties of cell membranes, dynamic changes in electronic properties of membrane surface, dynamic changes in electronic properties of cell membranes, electrical dipole, electrical quadruple, oscillation in electrical signal (e.g., oscillation in ions, pulsing electrical field, pulsing surface charge, pulsing voltage), electrical current, capacitance, three-dimensional electrical or charge cloud distribution, electrical properties at telomere of DNA and chromosome, capacitance, or impedance; the thermal property is temperature or vibrational frequency; the optical property is optical absorption, optical transmission, optical reflection, optical-electrical property, brightness, or fluorescent emission; radiation property is radiation emission, signal triggered by radioactive material, or information probed by radioactive material; the chemical property is pH value, chemical reaction, bio-chemical reaction, bio-electro-chemical reaction, reaction speed, reaction energy, speed of reaction, oxygen concentration, oxygen consumption rate, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property is density, shape, volume, or surface area; the biological property is surface shape, surface area, surface charge, surface biological property, surface chemical property, pH, electrolyte, ionic strength, resistivity, cell concentration, or biological, electrical, physical or chemical property of solution; the acoustic property is frequency, speed of acoustic waves, acoustic frequency and intensity spectrum distribution, acoustic intensity, acoustical absorption, or acoustical resonance; the mechanical property is internal pressure, hardness, flow rate, viscosity, fluid mechanical properties, shear strength, elongation strength, fracture stress, adhesion, mechanical resonance frequency, elasticity, plasticity, or compressibility.

In some other embodiments, each of the apparatus further comprises at least one or more additional micro-devices. In these embodiments, each of the micro-devices contained in the apparatus comprises a conductive material, an electrically insulating material, or a semiconductor material; and each of the micro-devices can comprise the same or different material(s) and can measure the same or different properties at the same or different time. These multiple micro-devices can be spaced out, e.g., with a distance of at least 10 angstroms on the substrate. The multiple micro-devices integrated in a disease detection apparatus can sequentially or simultaneously various parameters from a biological entity being detected at macroscopic or microscopic levels.

In some other embodiments, each of the micro-devices has the size ranging from about 1 angstrom (Å) to about 5 millimeter (e.g., from 5 Å to 1 millimeter).

In some other embodiments, the apparatus comprises one or more additional substrates on which the micro-devices are placed. Each of the substrates can comprise the same or a different material (e.g., a conductive material or an insulator), can be in the same or a different shape (e.g., a slab, a tube, or an array), and each substrate can be a two- or three-dimensional object. They can take the form of cylinder, slabs, or any other desired shapes and configurations, in order to further improve their measurement sensitivity, specificity, speed, sample size, and reduce cost and size.

The apparatus of the current invention can further count, record, and analyze the number or amount of circulating tumor cells in a biological object, and mark the cancer progression based on the information obtained. The apparatus can further predict the treatment efficacy, the progression-free survival, and overall survival data.

In terms of detection apparatus to integrate micro-devices, in one novel detection apparatus design, to increase measurement sensitivity, micro-devices mounted on two slabs separated by a small spacing with sample to be measured between the two said slabs can be used to detect CTCs with improved speed, with micro-devices measuring cells in the sample in parallel. The surface area of the slabs can be maximized in order to have maximum number of micro-devices placed on the slabs and enhance measurement efficiency and speed. Optionally, multiple micro-devices integrated on the surface of the slabs can be closely spaced with their spacing matching that of cells.

In another novel configuration, a detection apparatus integrated with micro-devices is shaped in the form of a cylinder, with multiple micro-devices with detection probes integrated or mounted in the inter surfaces of the cylinder and with sample to be measured (such as blood, lymph) flowing through the cylinder.

One of the key novel aspects of this patent application is the design and fabrication process flows of micro-devices and methods of using the micro-devices for contacting and measuring properties, at microscopic levels and in a three dimensional space, of a biological entity (e.g., a single cell). The micro-devices have micro-probes arranged in a three dimensional manner with feature sizes as small as a cell and capable of trapping, sorting, probing, measuring, or modifying biological entities. The probe comprises a flexible supporting structure to extend or contract the probe to move the biological subject.

Another aspect of this invention relates to methods for fabricating a micro-device. The methods include depositing various materials on a substrate and, in the interims of depositing every two materials, pattern the materials by a microelectronic technology or process, wherein the micro-device is capable of measuring at the microscopic level the electric, magnetic, electromagnetic, thermal, optical, acoustical, biological, chemical, physical, or mechanical property of a biologic material that the micro-device is to contact.

Still another aspect of this invention relates to methods for fabricating a micro-device, which include depositing a first material on the substrate, patterning the first material by a microelectronic technology or process to give rise to at least one patterned residual and leaving part of the substrate surface uncovered by the first material, depositing a second non-conductive material atop the processed first material and the substrate, creating an opening in the second material and exposing part of the patterned residual of the first material, filling up the opening in the second material with a third material. In some embodiments, the microelectronic technology or process is thin film deposition, photolithography, etching, cleaning, diffusion, ion implantation, or chemical mechanical polishing.

Yet in still another aspect, the invention provides methods for fabricating a micro-device, which include the first step of depositing a first material onto a substrate; the second step of depositing a second material onto the first material and then patterning the second material with a microelectronic technology or process; and repeating the second step at least once with a material that can be the same as or different from the first or second material. The materials used in the repeated steps can be the same as or different from the first or second material. In some embodiments, at least one of the materials used in fabricating the micro-device is a piezoelectric material or a conductive material.

In some embodiments, multiple fabricated micro-devices can be coupled, joined, and connected by physical or electrical method to constitute the more advanced devices.

In some embodiments, the apparatus of this invention can be integrated on a single device (e.g., by using a semiconductor processing technology) or assembled on a board (e.g., by using a computer packaging technology).

In some embodiments, patterning of a material is done by a microelectronic technology or process (e.g., chemical vapor deposition, physical vapor deposition, or atomic layer deposition to deposit various materials on a substrate as an insulator or conductor; lithography and etch to transfer patterns from design to structure; chemical mechanical planarization for planarization or patterning; cleaning for particle or contaminant removal; thermal spiking or anneal to reduce the crystal defects; diffusion or ion implantation for doping elements into specific layers). In some embodiments, patterning is planarization by chemical mechanical polishing.

In some other embodiments, the methods further include removal of a stack of multiple layers of materials by wet etch or plasma etch.

In some embodiments, the micro-device can move in any direction. For instance, two micro-devices can move in opposite directions.

In some embodiments, the micro-device thus fabricated is so patterned that it is capable of trapping, sorting, probing, measuring, or modifying a biological entity; or that it can piece through the membrane of a cell.

Another novel area of this application is the invention of micro-indentation probes and micro-probes for measuring a wide range of physical properties (such as mechanical properties) of biological entities (e.g., cells). Examples of such physical properties include, but are not limited to, hardness, shear strength, elongation strength, fracture stress, elasticity, stiffness, and properties related to cell membranes as the membranes may be a critical component in disease diagnosis.

Still yet another aspect of this invention is the design, fabrication, and integration of the various components in the disease detection apparatus. These components include, e.g., a sample containment and delivery unit; a delivery unit to deliver oxygen or desired fluid to maintain and prolong the life of biological entities in the biological sample being tested; a sample pre-treatment (or pre-processing) unit to concentrate diseased entities (such as diseased cells) in the sample; an array of sample delivery channels; a central disease detection unit comprising multiple detection probes, a central control unit comprising a logic processing unit, a memory unit, a sensor, a signal transmitter, a signal receiver, a micro-electro-mechanical device, a multi-functional device, a micro-instrument to perform surgery, drug delivery, cleaning, or medical function, and an application specific chip; and a waste sample treatment unit in which used sample can be treated, recycled, processed for reuse, or disposed.

Finally, another key novel aspect of the current application is the design, integration, and fabrication process flow of micro-devices capable of making highly sensitive and advanced measurements on very weak signals in biological systems for detecting CTCs on under complicated environment with very weak signal and relatively high noise background. Those novel capabilities using the class of micro-devices disclosed in this invention for disease detection include, e.g., making dynamic measurements, real time measurements (such as time of flight measurements, and combination of using probe signal and detecting response signal), phase lock-in technique to reduce background noise, pre-amplification techniques, noise cancellation methods, and 4-point probe techniques to measure very weak signals, and unique and novel probes to measure various electronic, electromagnetic and magnetic properties of biological samples at the single cell level.

As used herein, the term "or" is meant to include both "and" and "or." In other words, the term "or" may also be replaced with "and/or."

As used herein, a singular noun is meant to include its plural meaning. For instance, a micro device can mean either a single micro device or multiple micro-devices.

As used herein, the term "patterning" means shaping a material into a certain physical form or pattern, including a plane (in which case "patterning" would also mean "planarization.")

As used herein, the term "a biological subject", "a biological entity" or "a biological sample" for analysis, detection, test, or diagnosis refers to the subject to be analyzed by an apparatus of this invention. It can be a fluidic sample containing cells, e.g., a blood or lymph sample drawn from a mammal. It also can be a body fluid or its treated solutions, e.g., a human peripheral blood, lymphocyte, bone marrow, or their treated solutions. A treated solution as used herein refers to a solution that has been used to treat (e.g., wash, clean, suspense, dialyze, or carry) a biological subject.

As used herein, the term "subject" generally refers to part or whole of a biological entity (such as a mammal, e.g., a human person).

As used herein, the term "microscopic level" refers to the subject being analyzed by the CTC detection apparatus of this invention is of a microscopic nature and can be a single cell, for example white blood cells, red blood cells, or tumor cells.

As used herein, a "micro-device" or "micro device" can be any of a wide range of materials, properties, shapes, and degree of complexity and integration. The term has a general meaning for an application from a single material to a very complex device comprising multiple materials with multiple sub units and multiple functions. The complexity contemplated in the present invention ranges from a very small, single particle with a set of desired properties to a fairly complicated, integrated unit with various functional units contained therein. For example, a simple micro-device could be a single spherical particle of a diameter as small as 100 angstroms with a desired hardness, a desired surface charge, or a desired organic chemistry absorbed onto its surface. A more complex micro device could be a 1 millimeter device with a sensor, a simple calculator, a memory unit, a logic unit, and a cutter all integrated onto it. In the former case, the particle can be formed via a fumed or colloidal precipitation process, while the device with various components integrated onto it can be fabricated using various integrated circuit manufacturing processes.

A micro device used in the present invention can range in size (e.g., diameter) from on the order of about 1 angstrom to on the order of about 5 millimeters. For instance, a micro-device ranging in size from on the order of about 10 angstroms to on the order of 100 microns can be used in this invention for targeting biological molecules, entities or compositions of small sizes such as cell structures. Or, a micro-device ranging in size from on the order of about one micron to the order of 5 millimeters can be used in the present invention for targeting relatively large biological matters such as a portion of a human organ. As an example, a simple micro-device defined in the present application can be a single particle of a diameter less than 100 angstroms, with desired surface properties (e.g., with surface charge or a chemical coating) for preferential absorption or adsorption onto a targeted cell.

The present invention further provides an apparatus for detecting a disease in a biological subject, which comprises a sample inlet, a pre-processing unit, a probing and detecting unit, a signal processing unit, a measurement result display unit, a disposal processing unit, a system for delivering the biological subject, a system for distributing the biological subject, a distribution channel, a re-charging unit, a detection device, a global positioning system, a motion device, a signal transmitter, a signal receiver, a sensor, a memory storage unit, a logic processing unit, an application specific chip, a unit for recycling and reclaiming the biological subject, a micro-electro-mechanical device, a multi-functional device, or a micro-instrument to perform surgery, drug delivery, cleaning, or medical function.

In some embodiments of the apparatus, the pre-processing unit comprises a sample filtration unit, a recharging unit, a constant pressure delivery unit, a sample disturbing unit, or a sample pre-probing disturbing unit. The pre-charging unit increases the contraction ratio of certain substance of interests (such as cancer cells) and therefore makes the apparatus more effective and efficient in detecting the targeted biological subject (such as cancer cells), which is particularly beneficial for detecting very low level of biological subject of interests (such as cancer or tumor cells, e.g., CTCs which have a concentration of one part in 1 billion to 10 billion).

In some embodiments, the filtration unit can filter off unwanted substance by physical filtration (e.g., based on the electronic charge or size of the substance) or separation by chemical (thereby completely removing the undesirable substances), bio-chemical, bio-physical, bio-electrical, bio-mechanical, electro-mechanical, electro-chemical, thermal, optical, electrical, magnetic, electro-magnetic, electro-chemical-mechanical, electro-biological, electro-bio-chemical, or biological means.

In some embodiments, the sample filtration unit can include an entrance channel, a disturbing fluid channel, an accelerating chamber, and a slit. The slit and the interior walls of the entrance channel define two channels (e.g., a top channel and a bottom channel) wherein the biological subject can be separated due to the differences in its property (e.g., electric or physical property).

In some embodiments, a disturbing fluid is injected into the channel, either before or after the biological subject passes a probing micro-device, to aid the traveling or separation of the biological subject inside the channel. A bio-compatible fluid can be injected into the disturbing fluid channel to separate the biological subject. For example, the bio-compatible fluid can be injected from the entrance of the disturbing fluid channel and deliver to an opening in the entrance channel wall. The bio-compatible fluid can be liquid or semi-liquid, and can include saline, water, plasma, an oxygen-rich liquid, or any combination thereof In some other embodiments, the angle between the entrance channel and the disturbing fluid channel ranges from about 0° to about 180° (e.g., from about 30° to about 150°, from about 60° to about 120°, or from about 75° to about 105°, or about 90°).

In some other embodiments, the width of each channel can range from about 1 nm to about 1 mm (e.g., from about 2 nm to about 0.6 mm or from about 10 nm to about 0.2 mm). The channel can be straight, curved, or angled. The interior wall of the channel defines a circular, oval, square, rectangular or polygon space. In some other embodiments, the channel is a circular carbon nano-tube and has a diameter from about 0.5 nm to about 1 micron and a length from about 5.0 nm to about 10 mm.

In some other embodiments, at least one of the channels comprises one probing device attached to the channel's sidewall, and the probing device is capable of measuring at the microscopic level an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical property, or a combination thereof, of the biologic material. For example, the electrical property can be surface charge, surface potential, resting potential, electrical current, electrical field distribution, surface charge distribution, cell electronic properties, cell surface electronic properties, dynamic changes in electronic properties, dynamic changes in cell electronic properties, dynamic changes in cell surface electronic properties, dynamic changes in surface electronic properties, electronic properties of cell membranes, dynamic changes in electronic properties of membrane surface, dynamic changes in electronic properties of cell membranes, electrical dipole, electrical quadruple, three-dimensional electrical or charge cloud distribution, electrical properties at telomere of DNA and chromosome, capacitance, or impedance; the thermal property can be temperature or vibrational frequency; the optical property can be optical absorption, optical transmission, optical reflection, optical-electrical property, brightness, or fluorescent emission; the radiation property can be radiation emission, signal triggered by radioactive material, or information probed by radioactive material; the chemical property can be pH value, chemical reaction, bio-chemical reaction, bio-electro-chemical reaction, reaction speed, reaction energy, speed of reaction, oxygen concentration, oxygen consumption rate, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property can be density, shape, volume, or surface area; the biological property can be surface shape, surface area, surface charge, surface biological property, surface chemical property, pH, electrolyte, ionic strength, resistivity, cell concentration, or biological, electrical, physical or chemical property of solution; the acoustic property can be frequency, speed of acoustic waves, acoustic frequency and intensity spectrum distribution, acoustic intensity, acoustical absorption, or acoustical resonance; the mechanical property can be internal pressure, hardness, flow rate, fluid mechanical properties, viscosity, shear strength, elongation strength, fracture stress, adhesion, mechanical resonance frequency, elasticity, plasticity, or compressibility.

In some embodiments, at least one of the channels comprises at least two probing devices attached to the channel's sidewalls, and the probing devices are capable of measuring at the microscopic level electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical property, or a combination thereof, of the biologic subject. The probing devices measure the same or different properties at the same time or different times.

The two or more probing devices can be placed with a desired distance between each other (at least 10 angstroms). Examples of the desired distance include from about 10 nm to about 100 mm, from about 100 nm to about 10 mm, from about 8 microns to about 200 microns, from about 1 mm to about 10 mm.

In some embodiments, the sample filtration unit can comprise an entrance channel, a bio-compatible filter, an exit channel, or any combination thereof. When a biological subject passes through the entrance channel toward the exit channel, the biological subject of a size larger than the filter hole will be blocked against the exit channel, resulting in the smaller biological subject being flushed out through the exit channel. A bio-compatible fluid is injected from the exit to carry the biological subject accumulated around the filter and flush out from the channel. The biological subject with a large size is then filtered for further analysis and detection in the detecting component or unit of the apparatus.

In some embodiments, the sample pre-probing disturbing unit can include one micro-device with a channel, a slit located inside the channel, and optionally two plates outside the channel. The two plates can apply a signal, e.g., an electronic voltage, to the biological subject traveling through the channel and separates it based on the electronic charge the biological subject carries. The slit and the interior channels of the channel define two channels where the separated biological subjects enter and optionally are detected for its property at the microscopic level.

In some embodiments., the sample pre-probing disturbing unit applies to the biological entity an electric, magnetic, electro-magnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical mechanical signal, or a combination of the above signals. The signal can be applied, .e.g., with the two plates described above or in other means (depending on the nature of the signal). The signal as applied can be pulsed or constant.

In some embodiments, the recharging unit recharges nutrient or respiring gas (such as oxygen) or fluid to the biological subject. Alternatively, it can also clean up the metabolite of the biological subject. With such a recharging unit, the life stability of the biological subject in the sample is sustained and its use is extended, thereby giving more accurate, stable, consistent, and reliable detecting results. Examples of nutrient include bio-compatible strong or weak electrolyte, amino acid, mineral, ions, catalysts, oxygen, oxygen-rich liquid, intravenous drip, glucose, and protein. Another example of the nutrient is a solution containing nano-particles that can be selectively absorbed by certain biological subjects (e.g., cells or viruses).

The recharging system can be separate from and outside of the other components of the apparatus. Alternatively, it can also be installed within one of the other components, e.g., the probing and detecting unit or the disposal processing unit.

In some other embodiments, the signal processing unit comprises an amplifier (e.g., a lock-in amplifier), an A/D (alternate/direct electric current) converter, a micro-computer, a manipulator, a display, and network connections.

In some instances, the signal processing unit collects more than one signal (i.e., multiple signals), and the multiple signals can be integrated to cancel noise out or to enhance the signal to noise ratio. The multiple signals can be signals from multiple locations or from multiple times.

Biological subjects that can be detected by the apparatus include, e.g., blood, urine, saliva, tear, sweat, and lymph. The detection results can indicate the possible occurrence or presence of a disease (e.g., one in its early stage) in the biological subject.

As used herein, the term "absorption" typically means a physical bonding between the surface and the material attached to it (absorbed onto it, in this case). On the other hand, the word "adsorption" generally means a stronger, chemical bonding between the two. These properties are very important for the present invention as they can be effectively used for targeted attachment by desired micro devices for measurement at the microscopic level.

As used herein, the term "contact" (as in "the first micro-device contacts a biologic entity") is meant to include both "direct" (or physical) contact and "non-direct" (or indirect or non-physical) contact. When two subjects are in "direct" contact, there is generally no measurable space or distance between the contact points of these two subjects; whereas when they are in "indirect" contact, there is a measurable space or distance between the contact points of these two subjects.

As used herein, the term "probe" or "probing," in addition to its dictionary meaning, could mean applying a signal (e.g., an electrical, acoustic, magnetic or thermal signal) to a subject, thereby stimulating the subject and causing it to have some kind of intrinsic response.

As used herein, the term "electric property" refers to surface charge, surface potential, resting potential, electrical current, electrical field distribution, surface charge distribution, cell electronic properties, cell surface electronic properties, dynamic changes in electronic properties, dynamic changes in cell electronic properties, dynamic changes in cell surface electronic properties, dynamic changes in surface electronic properties, electronic properties of cell membranes, dynamic changes in electronic properties of membrane surface, dynamic changes in electronic properties of cell membranes, electric dipole, electrical quadruple, three-dimensional electrical or charge cloud distribution, electrical properties at telomere of DNA and chromosome, break down voltage, capacitance, and impedance of a biological subject to be analyzed.

As used herein, the term "magnetic property" refers to a diamagnetic, paramagnetic, or ferromagnetic property.

As used herein, the term "electro-magnetic property" refers to a property that has both electric and magnetic dimensions.

As used herein, the term "thermal property" refers to temperature, freezing point, melting point, evaporation temperature, glass transition temperature, thermal conductivity, or vibrational energy of molecules.

As used herein, the term "optical property" refers to reflection, optical absorption, optical scattering, wave length dependent properties, color, luster, brilliance, scintillation, or dispersion.

As used herein, the term "radiation property" refers to radiation emission, signal triggered by radioactive material, or information probed by radioactive material. The meaning of "radiation property" used in the context of this application has been extended to how an entity such as a biological entity responds to or interacts with a radioactive material or a product (such as a positron) generated by a radioactive material.

As used herein, the term "acoustical property" refers to the characteristics found within a structure that determine the quality of sound in its relevance to hearing. It can generally be measured by the acoustic absorption coefficient. See, e.g., U.S. Pat. No. 3,915,016, for means and methods for determining an acoustical property of a material; T. J. Cox et al., *Acoustic Absorbers and Diffusers,* 2004, Spon Press.

As used herein, the term "biological property" is meant to generally include chemical and physical properties of a biological entity.

As used herein, the term "chemical property" refers to reactivity, pH value, ionic strength, or bonding strength within the biological sample.

As used herein, the term "physical property" refers to any measurable property the value of which describes a physical system's state at any given moment in time. The physical properties of a biological sample may include, but are not limited to absorption, albedo, area, brittleness, boiling point, capacitance, color, concentration, density, dielectric, electric charge, electrical conductivity, capacitance, electrical impedance, electric field, electric potential, emission, flow rate, fluidity, frequency, inductance, intrinsic impedance, intensity, irradiance, luminance, luster, malleability, magnetic field, magnetic flux, mass, melting point, momentum, permeability, permittivity, pressure, radiance, solubility, specific heat, strength, temperature, tension, thermal conductivity, velocity, viscosity, volume, and wave impedance.

As used herein, the term "mechanical property" refers to strength, hardness, toughness, elasticity, plasticity, brittleness, ductility, shear strength, elongation strength, fracture stress, fluid mechanical properties, or adhesion of the biological sample.

As used herein, the term "conductive material" (or its equivalent "electric conductor") is a material which contains movable electric charges. A conductive material can be a metal (e.g., aluminum, copper, silver, tungsten, or gold) or non-metallic (e.g., graphite, solutions of salts, plasmas, or conductive polymers). In metallic conductors, such as copper or aluminum, the movable charged particles are electrons (see electrical conduction). Positive charges may also be mobile in the form of atoms in a lattice that are missing electrons (known as holes), or in the form of ions, such as in the electrolyte of a battery.

As used herein, the term "electrically insulating material" (also known as "insulator" or "dielectric") refers to a material that resists the flow of electric current. An insulating material has atoms with tightly bonded valence electrons. Examples of electrically insulating materials include glass, silicon dioxide, or organic polymers (e.g., rubber, plastics, or Teflon).

As used herein, the term "semiconductor" (also known as "semiconducting material") refers to a material with electrical conductivity due to electron flow (as opposed to ionic conductivity) intermediate in magnitude between that of a conductor and an insulator. Examples of inorganic semiconductors include silicon-based materials. Examples of organic semiconductors include such aromatic hydrocarbons as the polycyclic aromatic compounds pentacene, anthracene, and rubrene; and polymeric organic semiconductors such as poly(3-hexylthiophene), poly(p-phenylene vinylene), polyacetylene and its derivatives. Semiconducting materials can be crystalline solids (e.g., silicon), amorphous (e.g., hydrogenated amorphous silicon and mixtures of arsenic, selenium and tellurium in a variety of proportions), or even liquid.

As used herein, the term "biological material" has the same meaning of "bio-material" as understood by a person skilled in the art. Without limiting its meaning, biological materials or biomaterials can generally be produced either in nature or synthesized in the laboratory using a variety of chemical approaches utilizing organic compounds (e.g., small organic molecules or polymers) or inorganic compounds (e.g., metallic components or ceramics). They generally can be used or adapted for a medical application, and thus comprise whole or part of a living structure or biomedical device which performs, augments, or replaces a natural function. Such functions may be benign, like being used for a heart valve, or may be bioactive with a more interactive functionality such as hydroxy-apatite coated hip implants. Bio-materials can also be used every day in dental applications, surgery, and drug delivery. For instance, a construct with impregnated pharmaceutical products can be placed into the body, which permits the prolonged release of a drug over an extended period of time. A bio-material may also be an autograft, allograft, or xenograft which can be used as a transplant material. All these materials that have found applications in other medical or biomedical fields can also be used in the present invention.

As used herein, the term "microelectronic technology or process" generally encompasses the technologies or processes used for fabricating micro-electronic and optical-electronic components. Examples include lithography, etching (e.g., wet etching, dry etching, or vapor etching), oxidation, diffusion, implantation, annealing, film deposition, cleaning, direct-writing, polishing, planarization (e.g., by chemical mechanical polishing), epitaxial growth, metallization, process integration, simulation, or any combinations thereof. Additional descriptions on microelectronic technologies or processes can be found in, e.g., Jaeger, Introduction to Microelectronic Fabrication, 2nd Ed., Prentice Hall, 2002; Ralph E. Williams, Modern GaAs Processing Methods, 2nd Ed., Artech House, 1990; Robert F. Pierret, Advanced Semiconductor Fundamentals, 2nd Ed., Prentice Hall, 2002; S. Campbell, The Science and Engineering of Microelectronic Fabrication, 2nd Ed., Oxford University Press, 2001, the contents of all of which are incorporated herein by reference in their entireties.

As used herein, the term "carbon nano-tube" generally refers to as allotropes of carbon with a cylindrical nano-structure. See, e.g., Carbon Nanotube Science, by P. J. F. Harris, Cambridge University Press, 2009, for more details about carbon nano-tubes.

Through the use of a single micro-device or a combination of micro-devices integrated into a CTC detection apparatus, the CTC detection capabilities can be significantly improved in terms of sensitivity, specificity, speed, cost, apparatus size, functionalities, multi-tasking, and ease of use, along with reduced invasiveness and side-effects. A large number of micro-device types capable of measuring a wide range of microscopic properties of biological sample for CTC detection can be integrated and fabricated into a single detection apparatus using micro-fabrication technologies and novel process flows disclosed herein. While for the purposes of demonstration and illustration, a few novel, detailed examples have been shown herein on how microelectronics or nano-fabrication techniques and associated process flows can be utilized to fabricate highly sensitive, multi-functional, and miniaturized detection devices, the principle and general approaches of employing microelectronics and nano-fabrication technologies in the design and fabrication of high performance detection devices have been contemplated and taught, which can and should be expanded to various combination of fabrication processes including but not limited to thin film deposition, patterning (lithography and etch), planarization (including chemical mechanical polishing), ion implantation, diffusion, cleaning, various materials, and various process sequences and flows and combinations thereof.

BRIEF DESCRIPTIONS OF THE FIGURES

FIG. 1 (a) is a perspective illustration of a CTC detection apparatus of this invention in which a biological sample placed in it or moving through it can be tested. FIG. 1(b) and FIG. 1(c) illustrate the apparatus which comprises multiple individual detection micro-devices.

FIG. 2 (a) is a perspective, cross-sectional illustration of a CTC detection apparatus of this invention with multiple micro-devices. A biological sample is placed in the apparatus or moving through it while one or more microscopic properties of this biological sample are measured with the multiple micro-devices. FIGS. 2(b)-2(l) are perspective illustrations of the novel process flow for fabricating the micro-device. FIGS. 2(m)-2(n) are cross-sectional views of an apparatus comprising multiple individual micro-devices.

Figure 13:
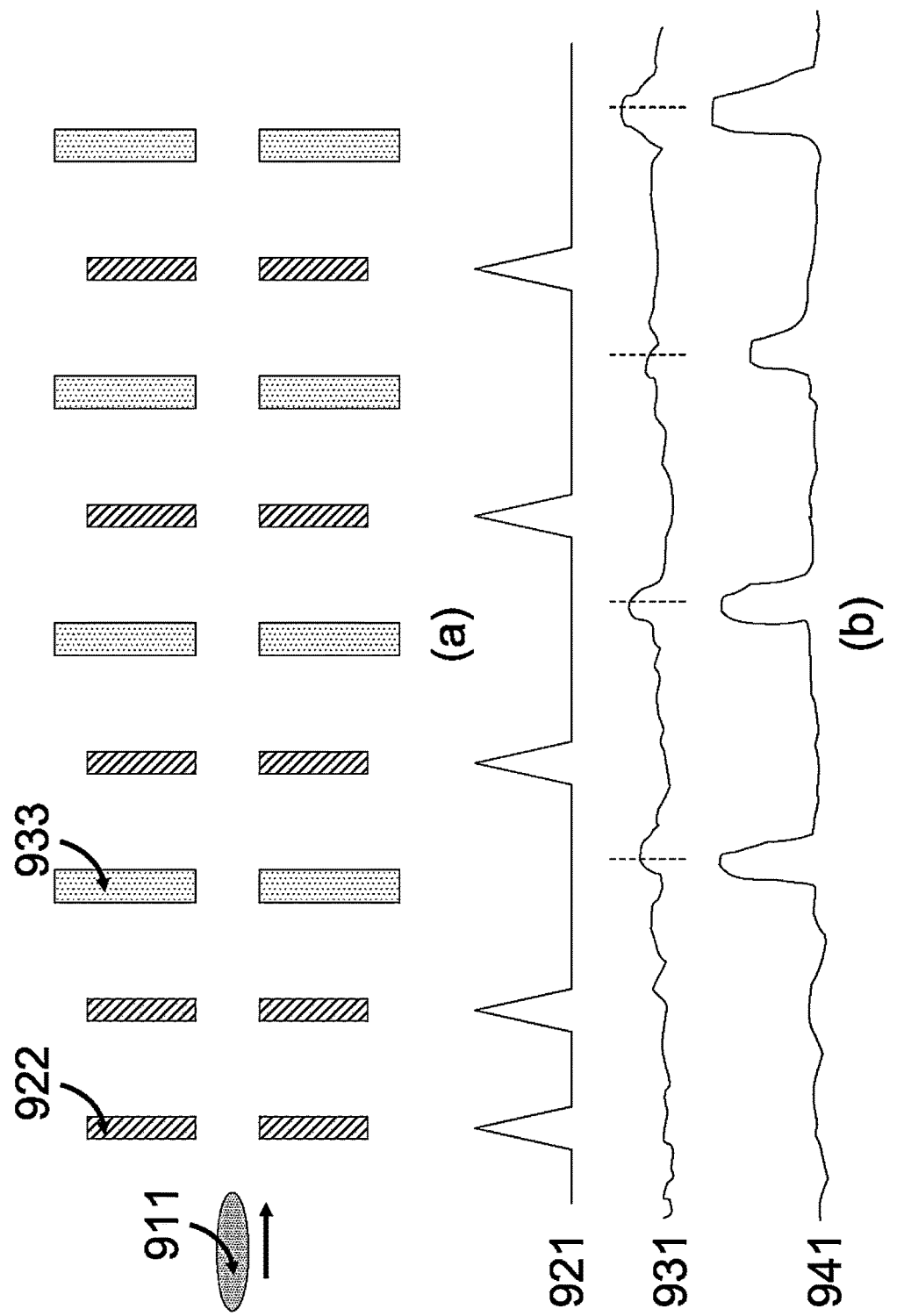

FIG. 13 illustrates a novel time of flight detection arrangement for CTC detection applications, in which both clock signal generator and signal detection probes are used, along with schematically recorded clock signal, probe signal (signal detected by probing micro-device), and processed and enhanced signal after signal filtering using phase lock-in processing technique to enhance the detected signal.

Figure 14:
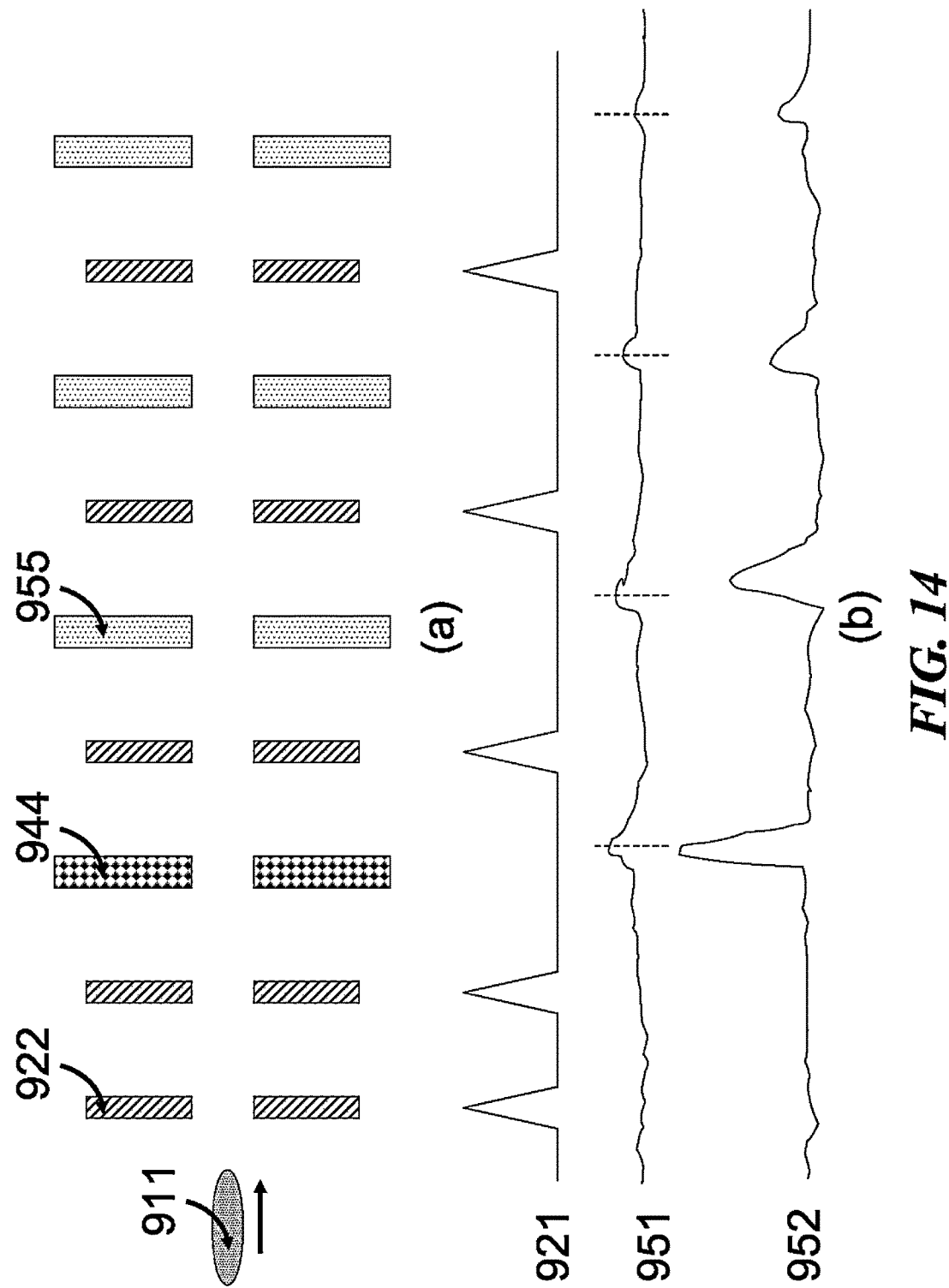

FIG. 14 illustrates yet another time of flight CTC detection arrangement in which clock signal generators, a probe signal generator, and signal detection probes are used, along with schematically recorded clock signal, detected signal by probing micro-device in response to probe signal, and processed and enhanced signal after signal filtering using phase lock-in processing technique to enhance the detected signal showing detected response signal as a function of time (response signal delays over time in this case).

FIG. 15 illustrates another novel time of flight CTC detection application, in which a set of novel micro-filters are utilized to detect biological entities via separation of biological entities by their various, specific properties such as size, weight, shape, electrical properties, or surface properties.

Figure 16:
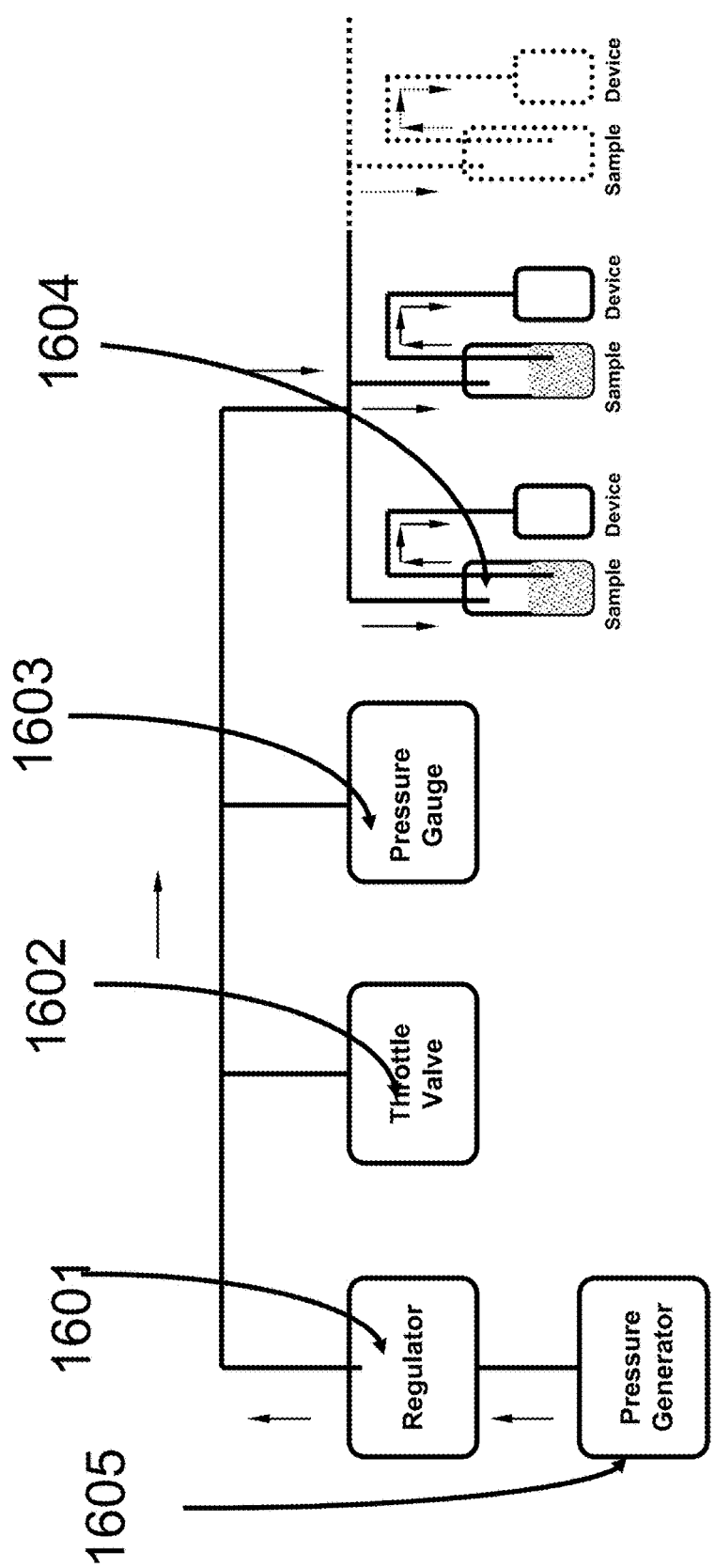

FIG. 16 illustrates a fluid delivery system, which is a pretreatment part for the CTC detection apparatus, and it delivers a sample or auxiliary material at a desired pressure and speed into a device.

FIGS. 17(b)-17(c) illustrate a novel device which can engage in cellular communications at the single cell level by simulating cellular signals and receiving the cell's responses which can be a signal of electric, magnetic, electro-magnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical property. FIG. 17(a) illustrates how the signal is processed and responded in a single cell.

Figure 18:
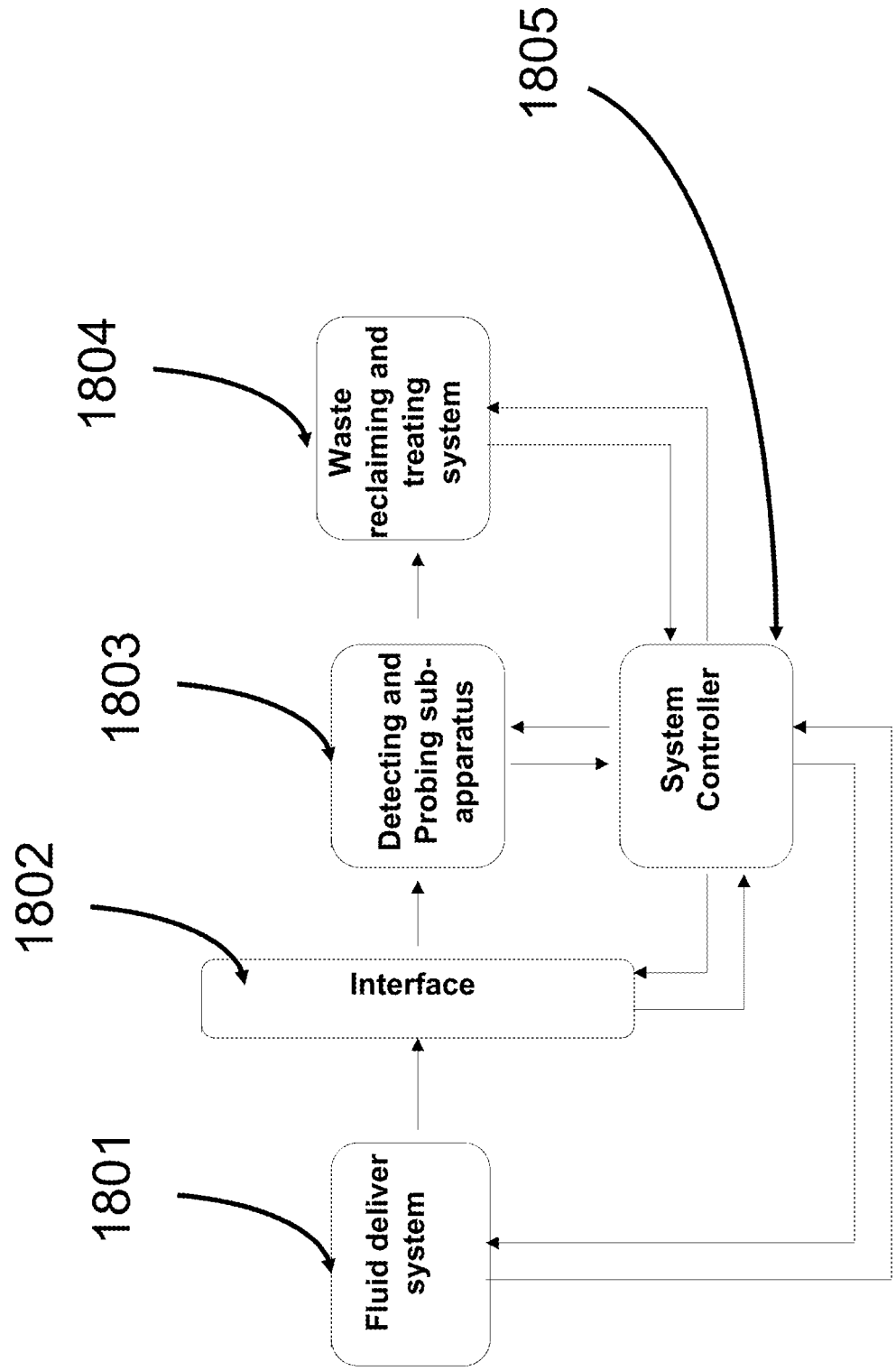

FIG. 18 illustrates a system block diagram of a CTC detection apparatus, comprising various functional modules.

Figure 19:
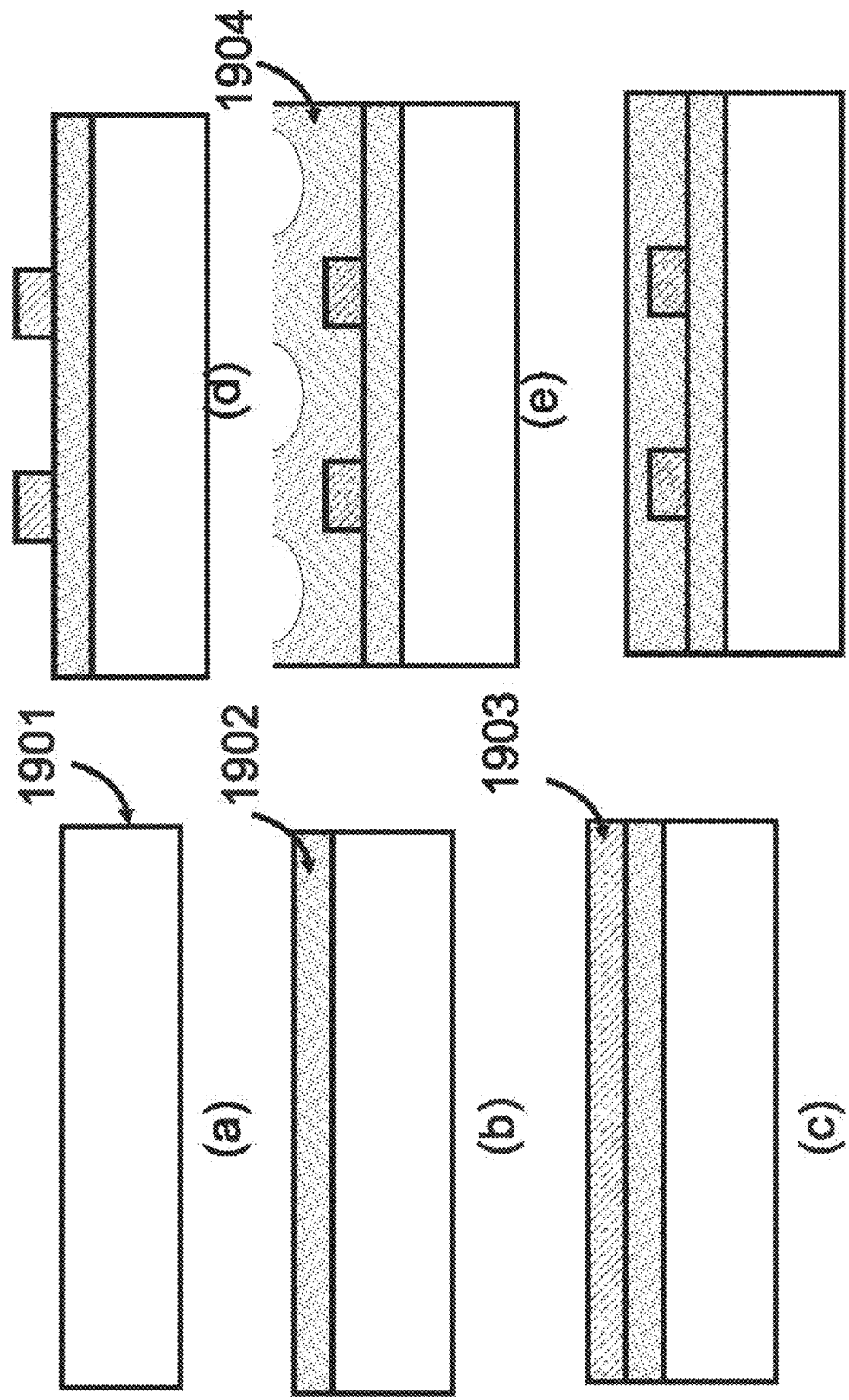
Figure 19:
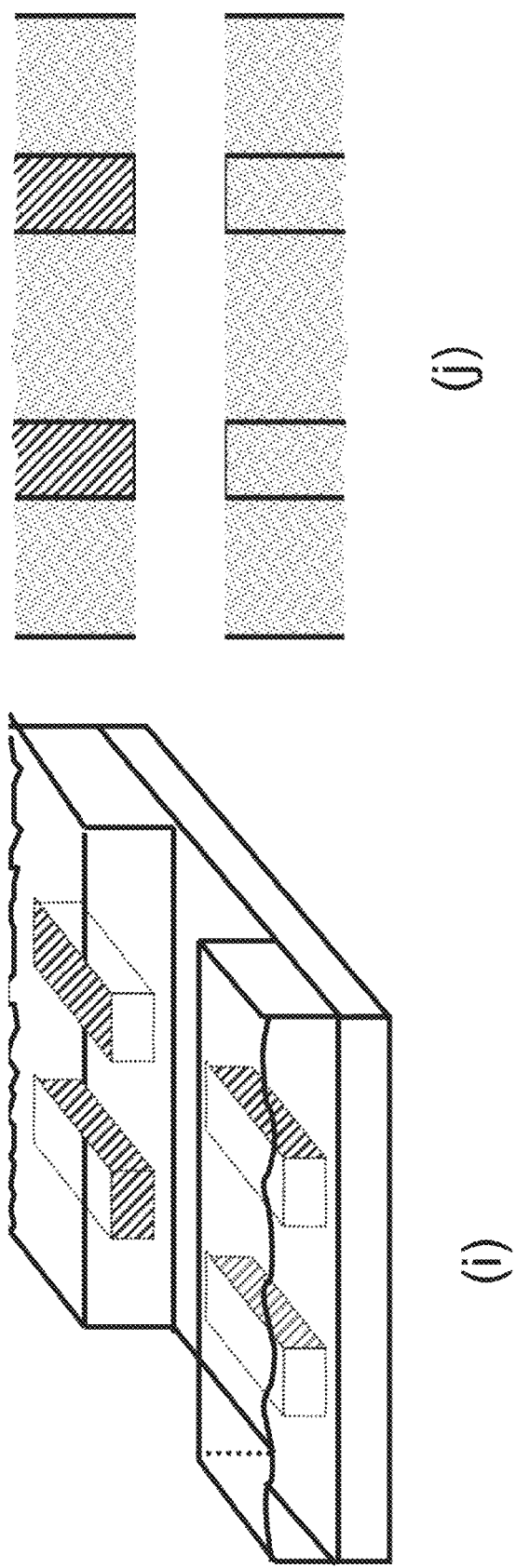
Figure 19:
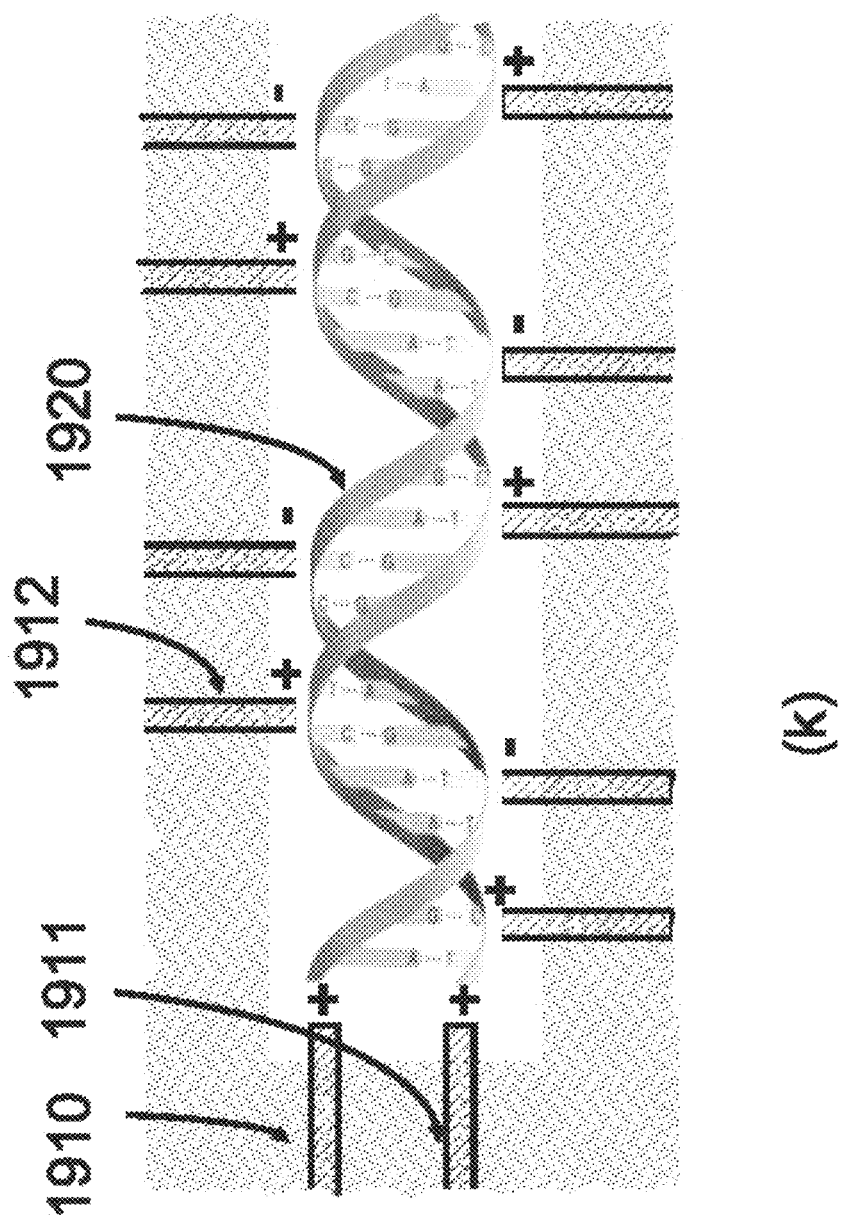
Figure 19:
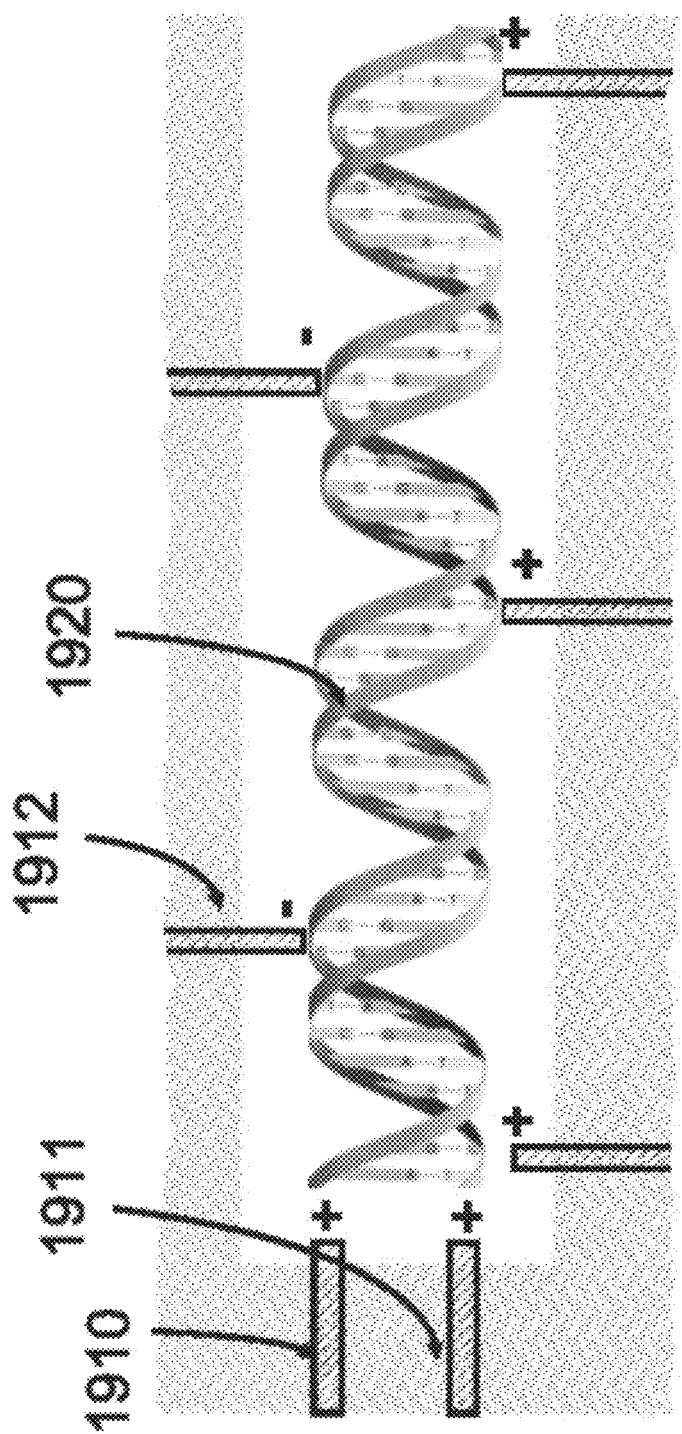

FIG. 19 illustrates an apparatus capable of communicating, trapping, sorting, analyzing, treating, or modifying a DNA and measuring the DNA's various properties.

Figure 20:
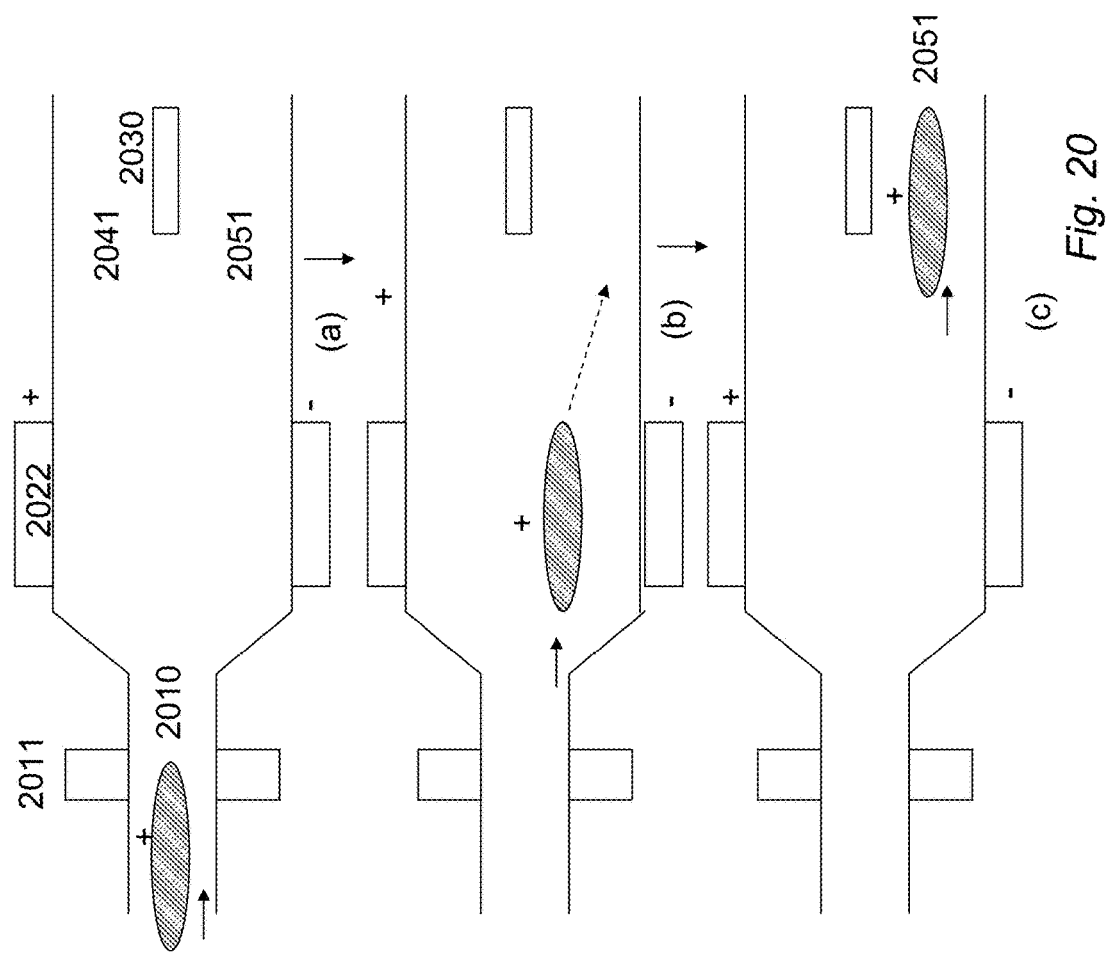

FIG. 20 illustrates an apparatus of this invention that can detect the surface charge on biological subjects and separate them by a slit based on the charge.

Figure 21:
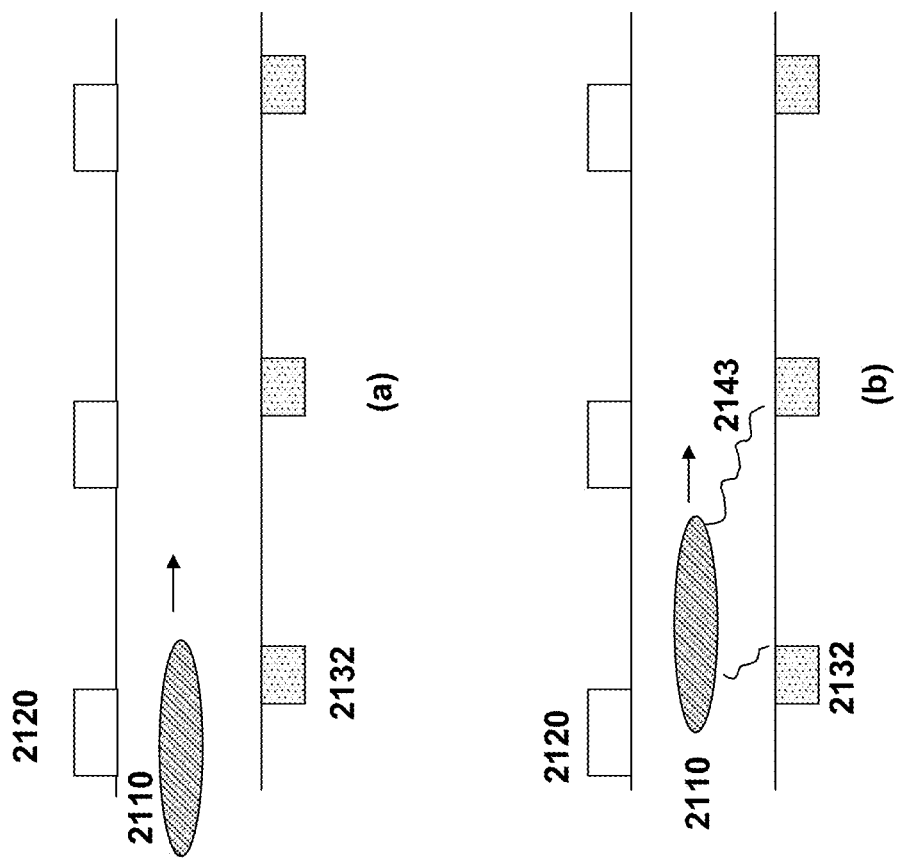

FIG. 21 illustrates another apparatus of this invention that can detect the optical properties of the biological subject with a set of optical sensors.

Figure 22:
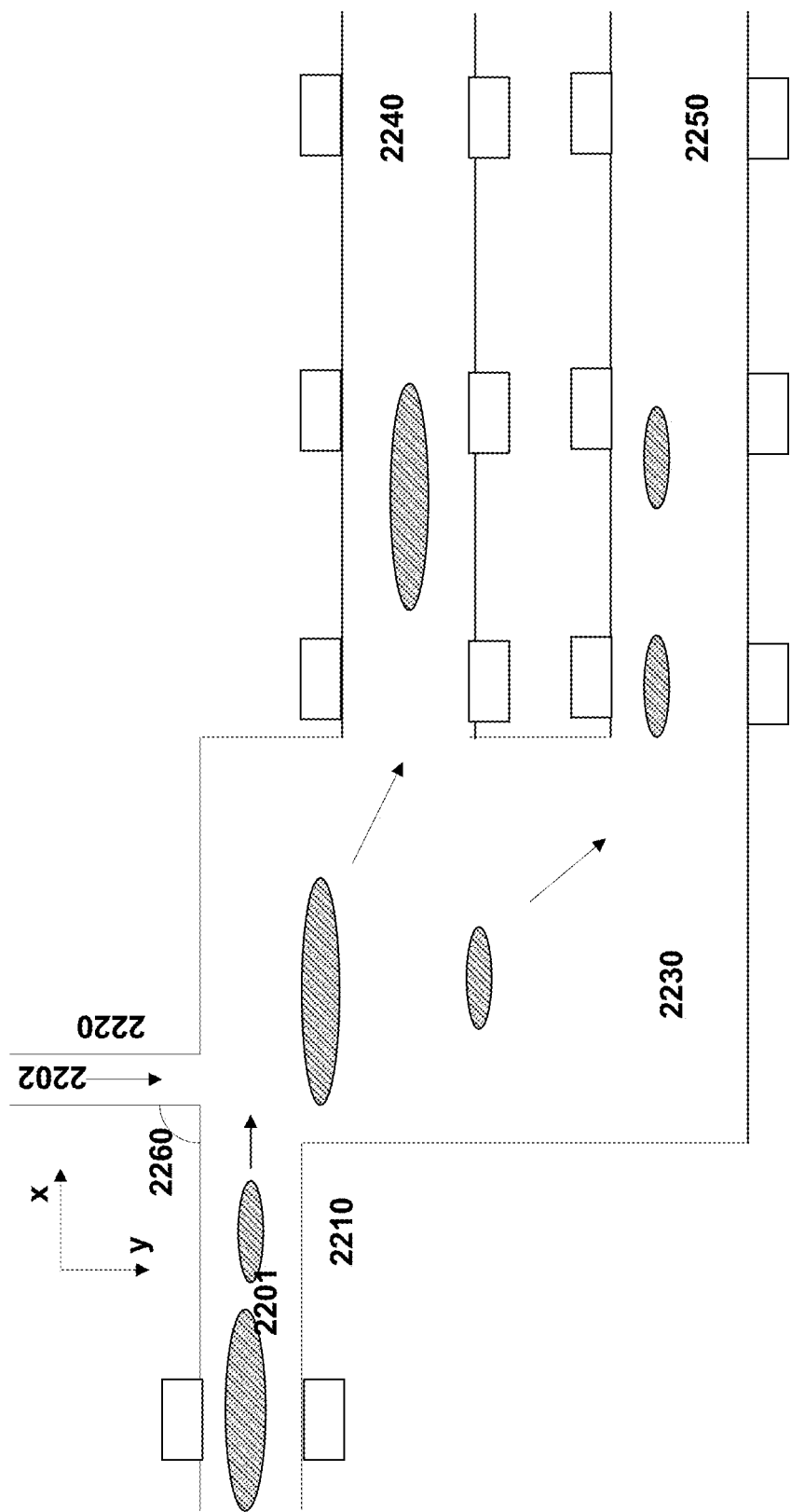

FIG. 22 illustrates another apparatus of this invention that can separate biological subjects of different geometric size and detect their properties respectively.

Figure 23:
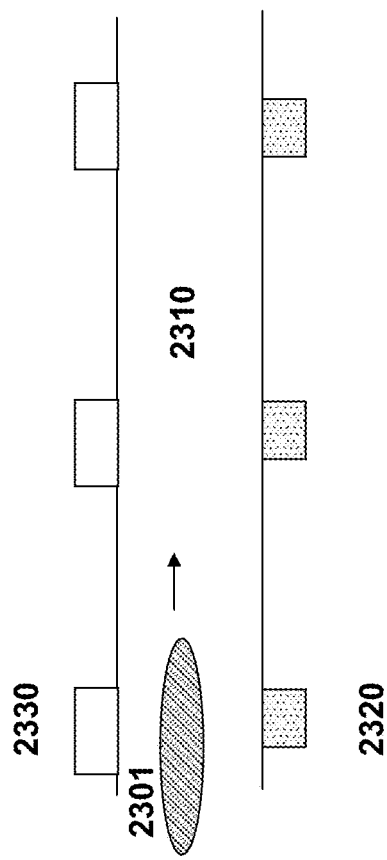

FIG. 23 illustrates an apparatus of this invention that can measure the acoustic property of a biological subject.

Figure 24:
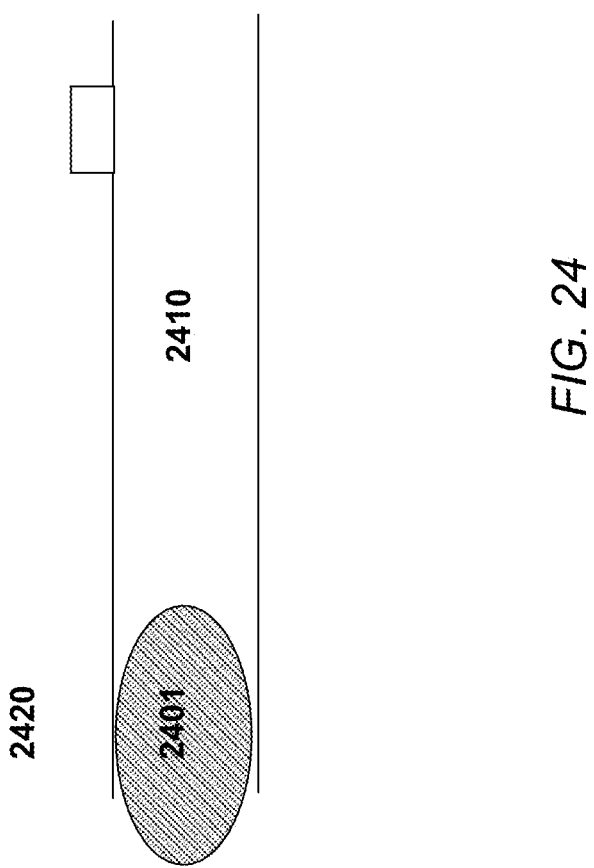

FIG. 24 illustrates an apparatus of this invention that can measure the internal pressure of a biological subject.

Figure 25:
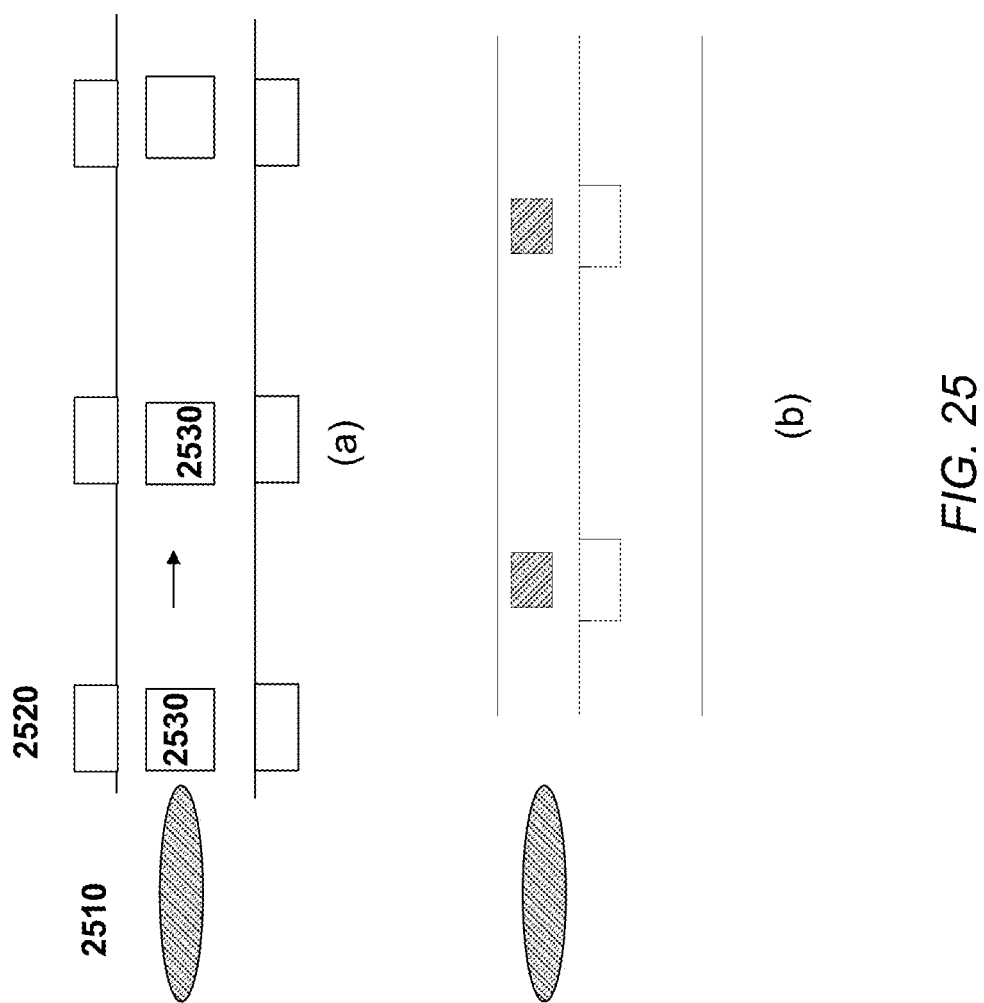
Figure 25:
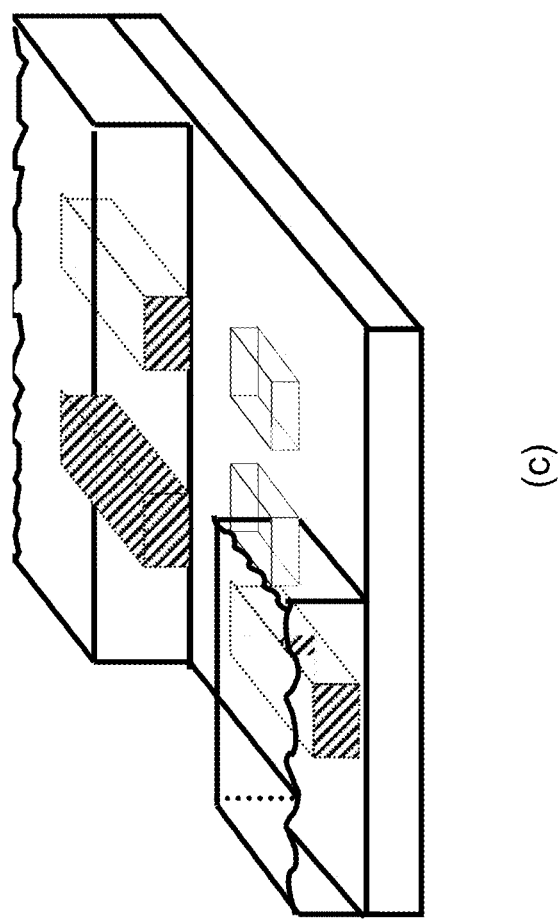

FIG. 25 illustrates an apparatus of this invention that has concaves between the probe couples, in the bottom or ceiling of the channel.

Figure 26:
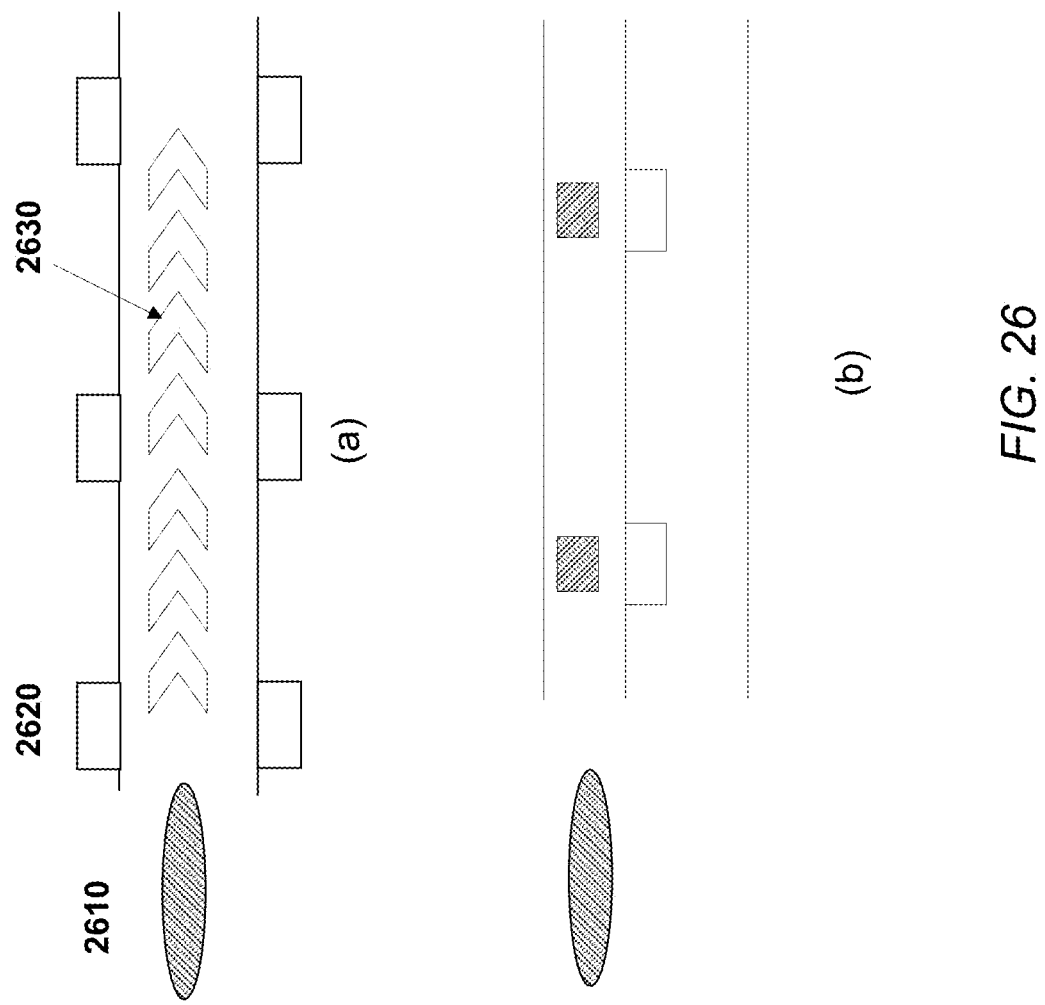

FIG. 26 illustrates another apparatus of this invention that has concaves of a different shape from those illustrated in FIG. 25.

Figure 27:

FIG. 27 illustrates an apparatus of this invention that has a stepped channel.

Figure 28:
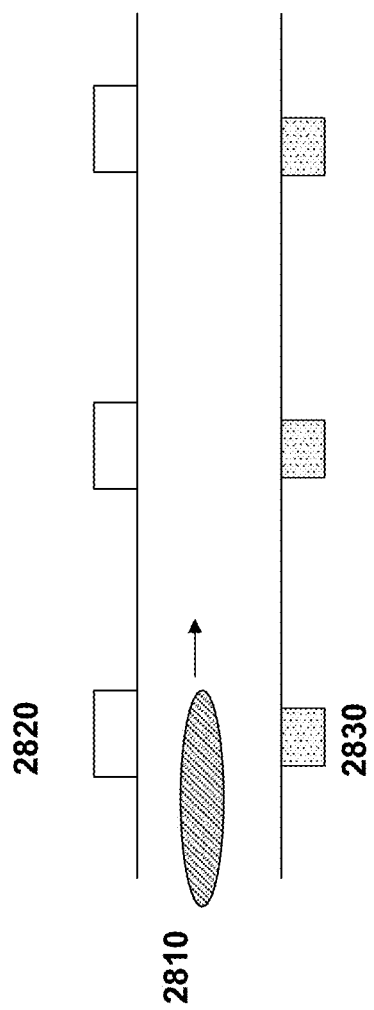

FIG. 28 illustrates an apparatus of this invention that has a set of thermal meters.

Figure 29:
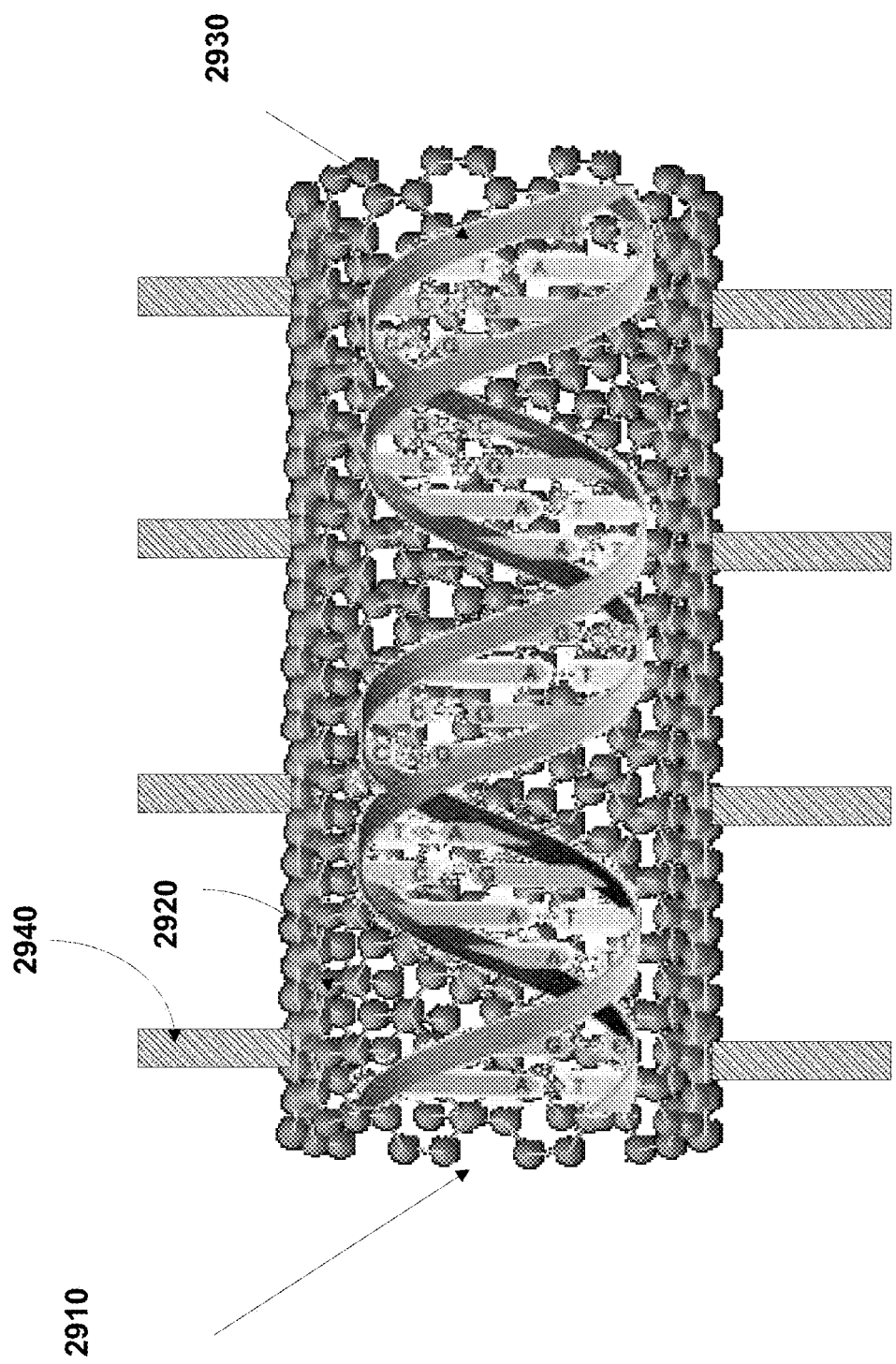

FIG. 29 illustrates an apparatus of this invention that includes a carbon nano-tube as the channel with DNA contained therein.

Figure 30:
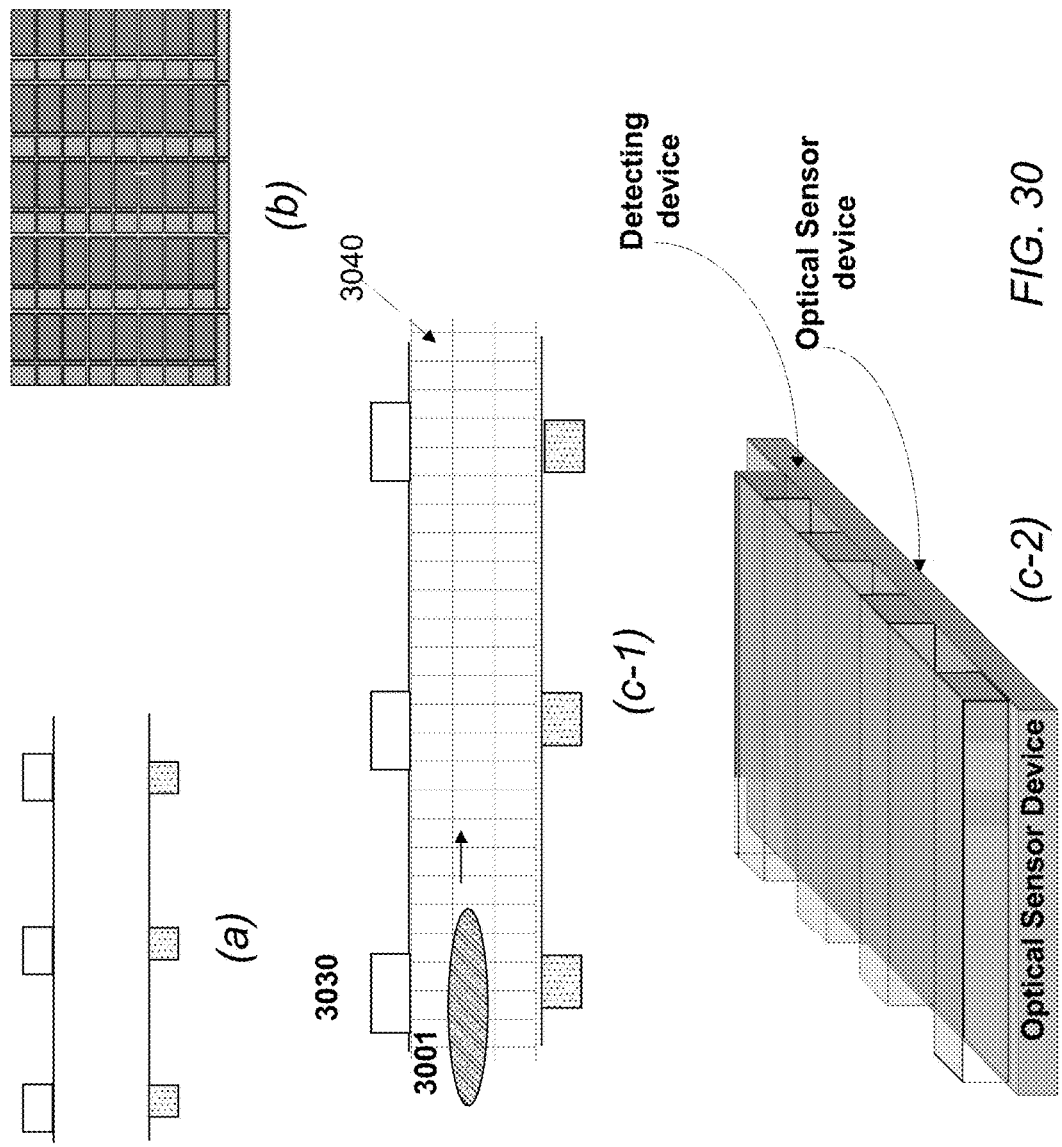
Figure 30:
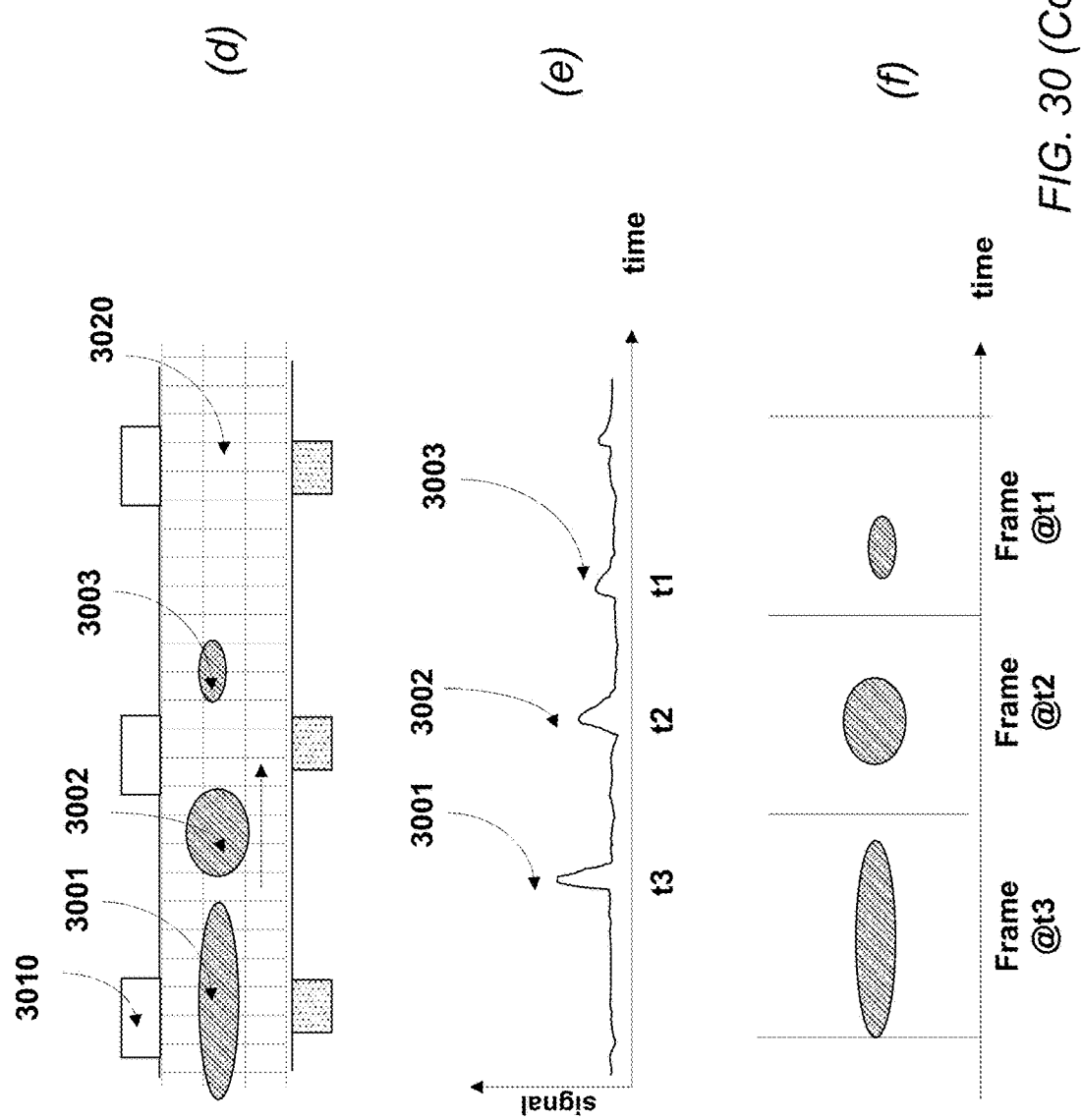

FIG. 30 illustrated an integrated apparatus of this invention that includes a detecting device and an optical sensor.

Figure 31:
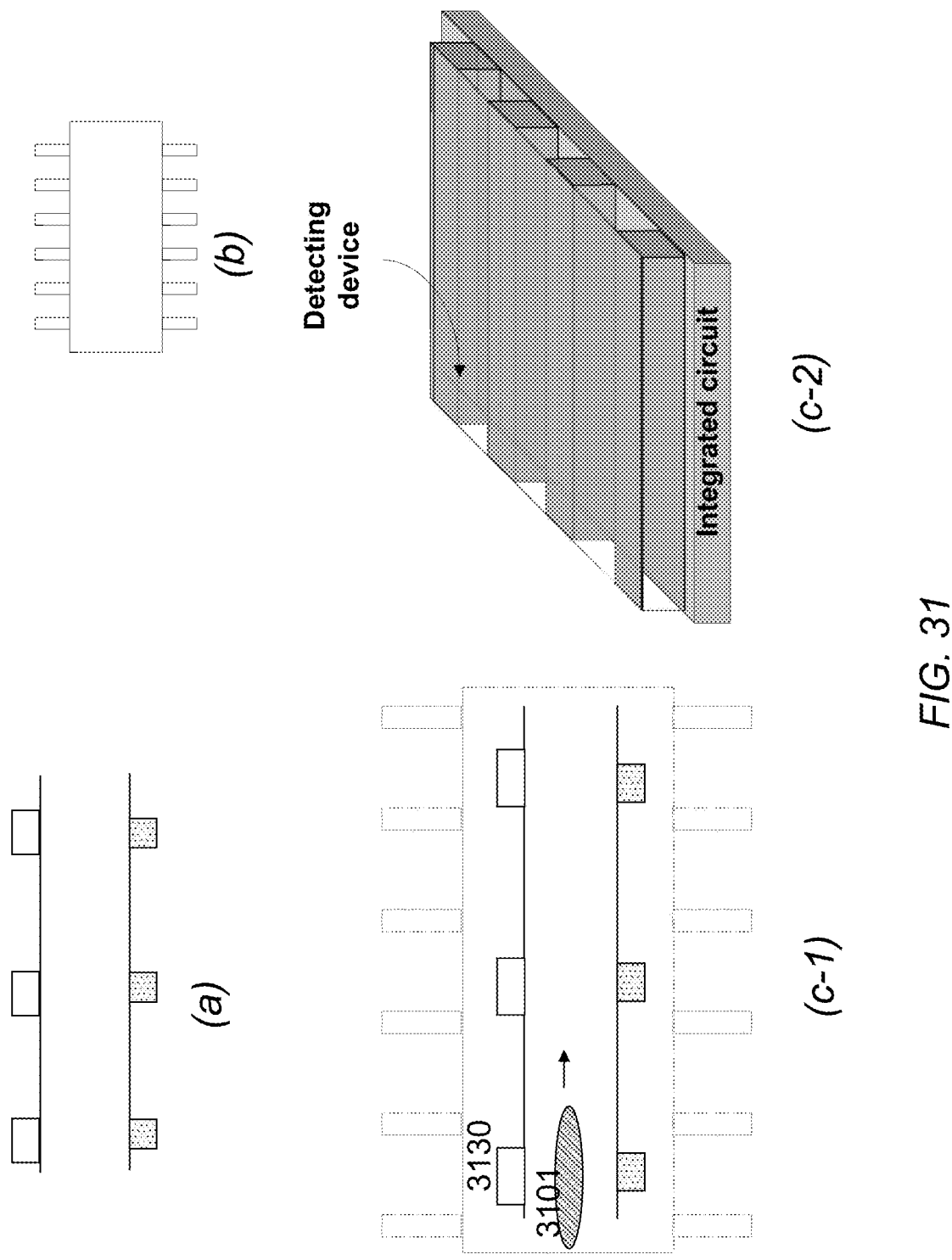

FIG. 31 illustrated an integrated apparatus of this invention that includes a detecting device and a logic circuitry.

Figure 32:
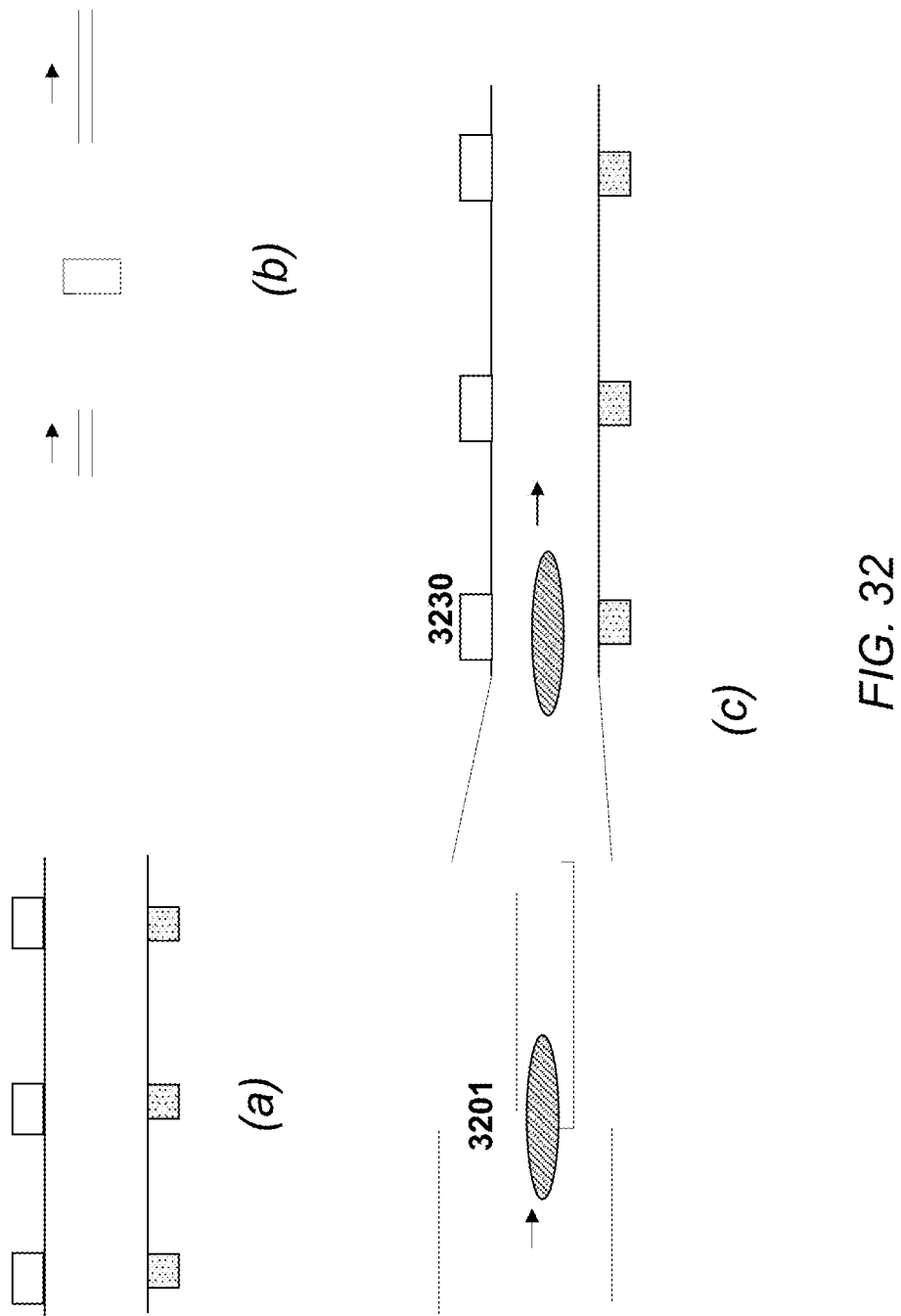

FIG. 32 illustrates an apparatus of this invention that includes a detecting device and a filter.

Figure 33:
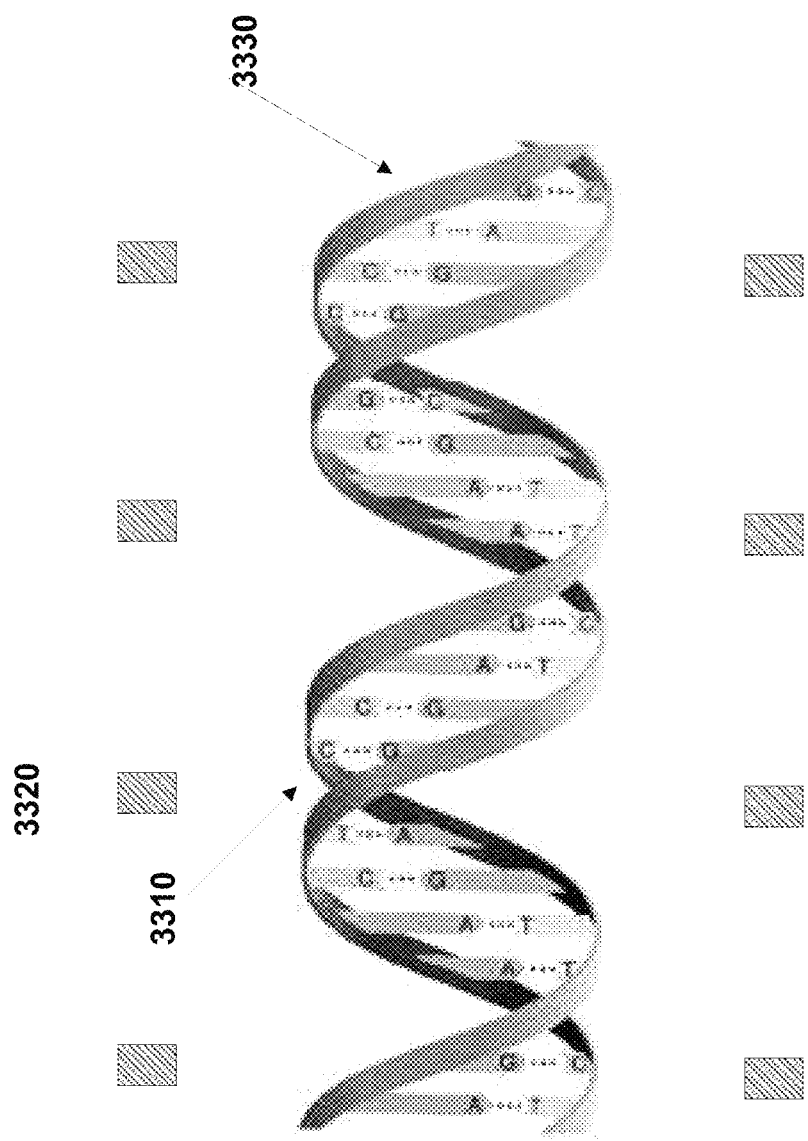

FIG. 33 illustrates how micro-devices of this invention can be used to measure a DNA' geometric factors.

Figure 34:
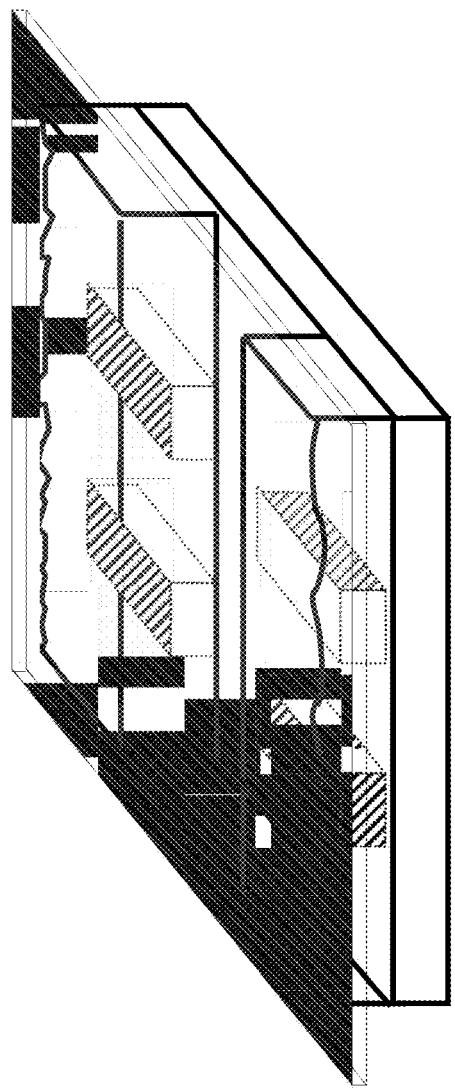

FIG. 34 illustrates a process for fabricating a micro-device of this invention with a cover atop the trench to form a channel.

Figure 35:
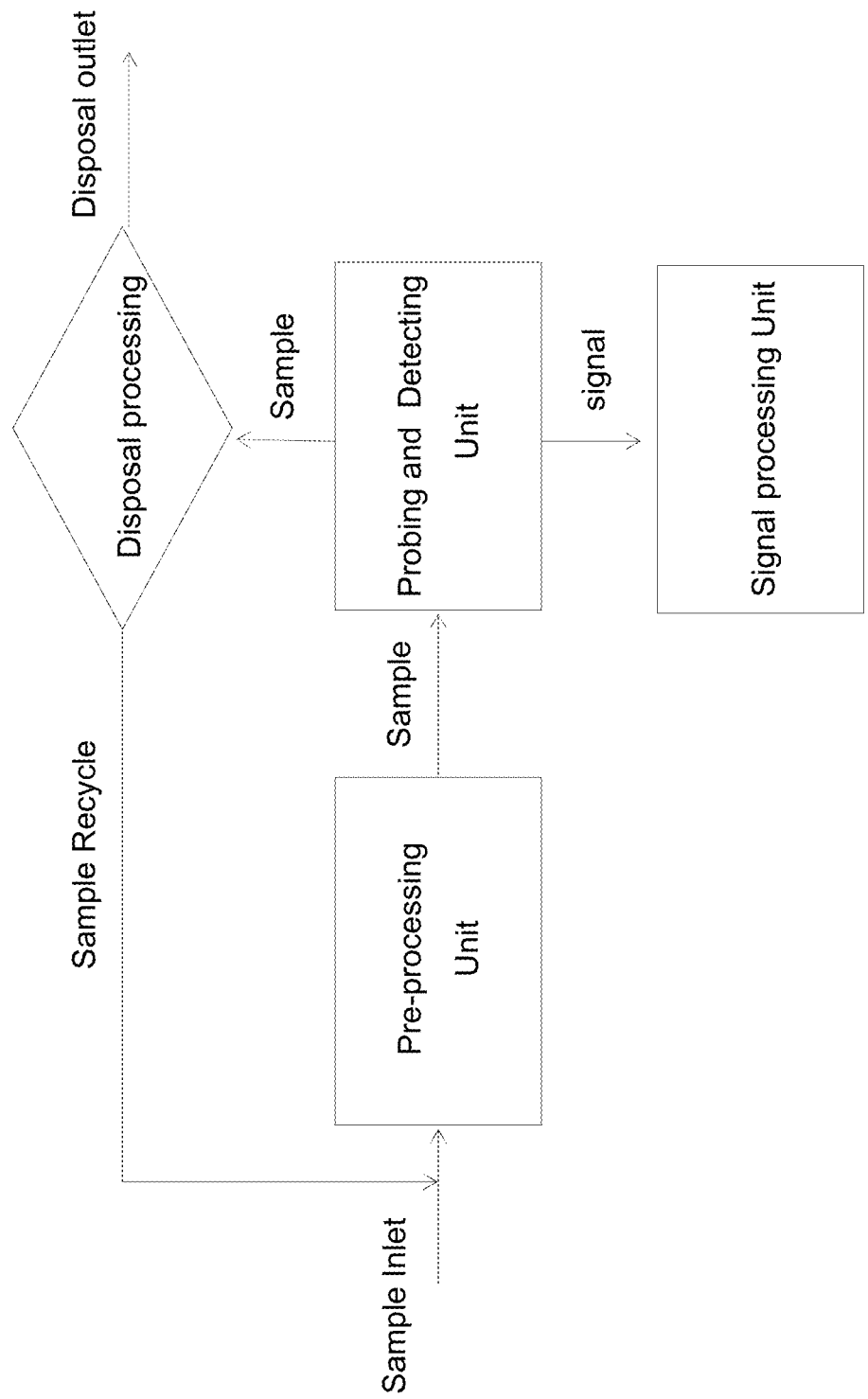

FIG. 35 is a diagram of an apparatus of this invention for detecting a disease in a biological subject.

Figure 36:
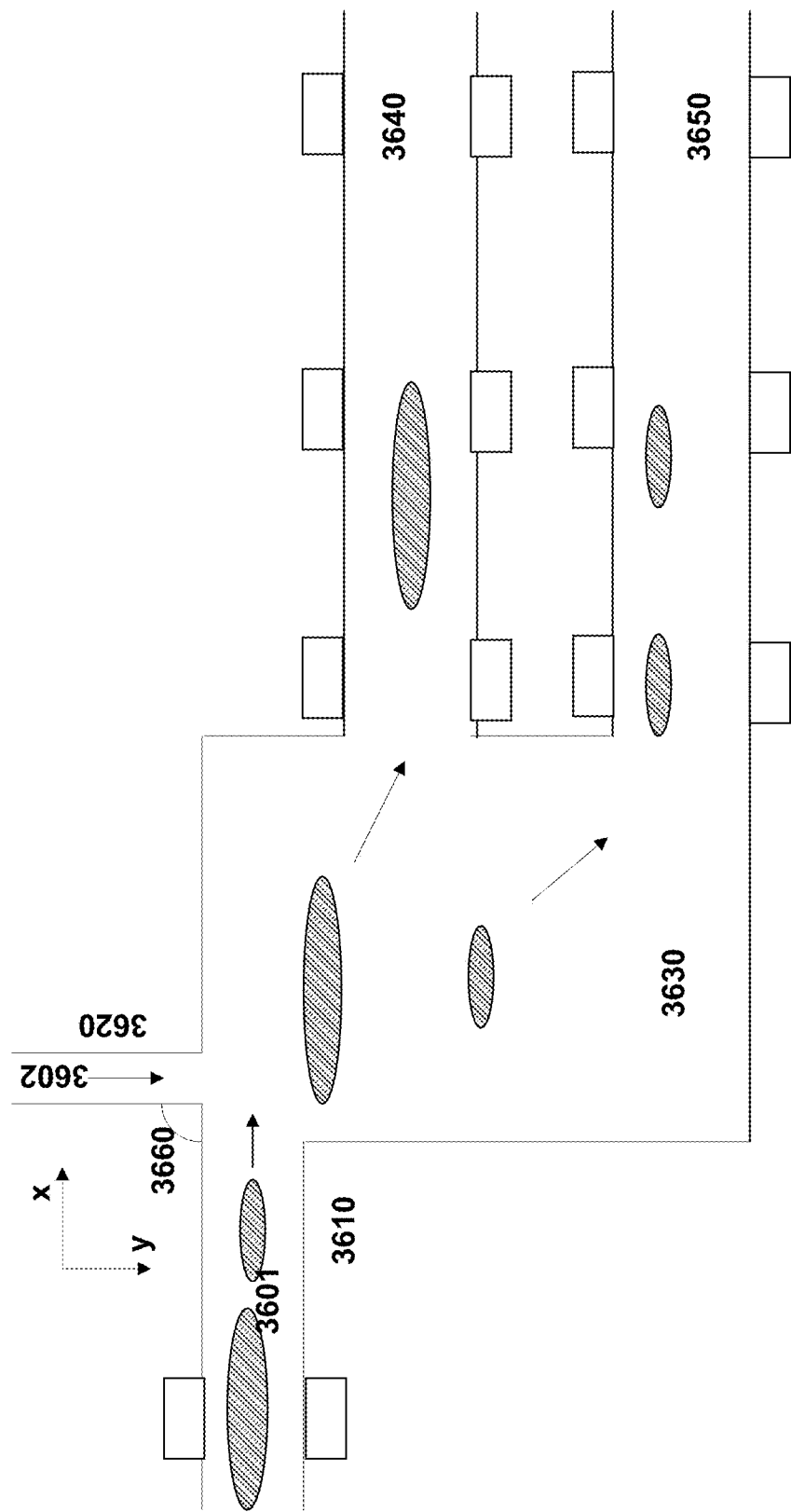

FIG. 36 shows an example of a sample filtration unit.

Figure 37:
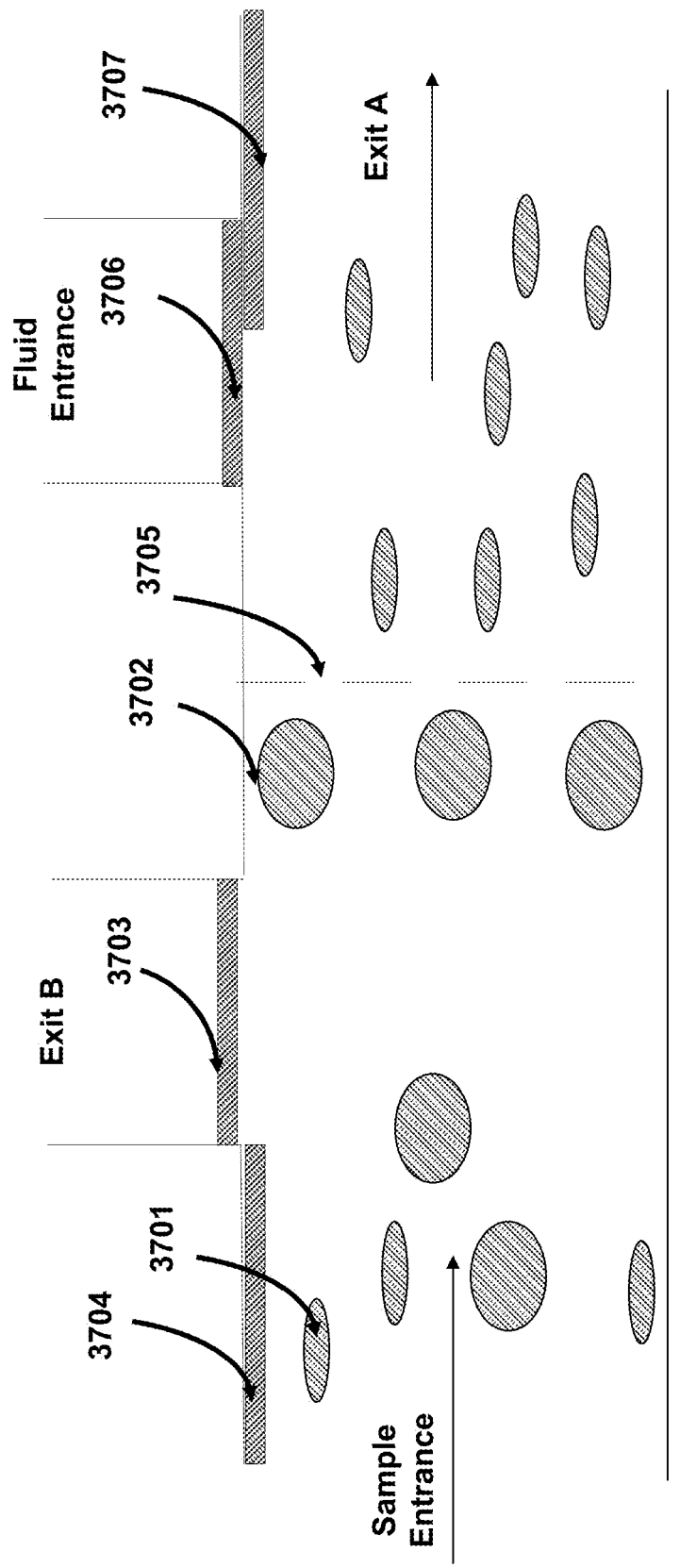
Figure 37:
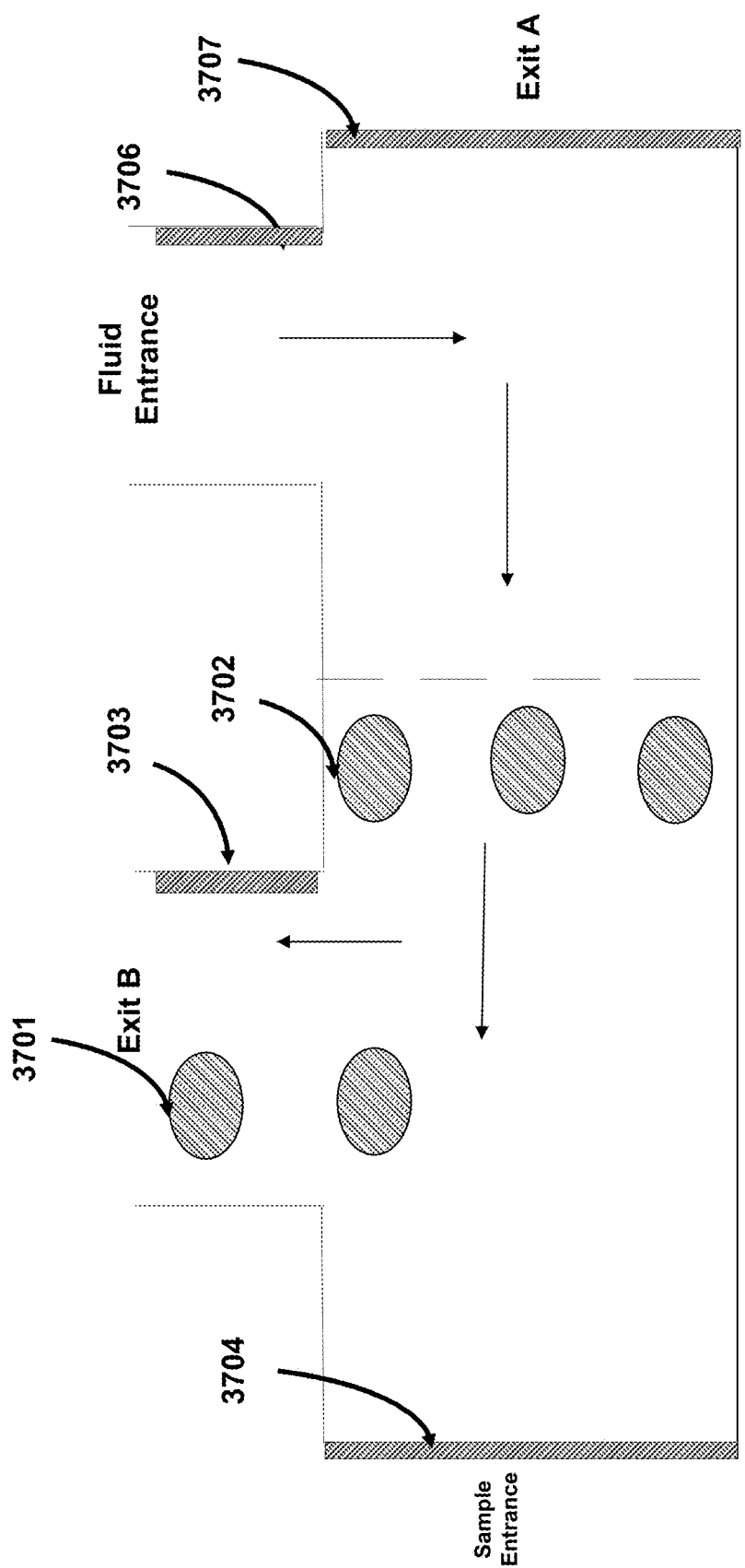

FIG. 37 shows another example of a sample filtration unit.

Figure 38:
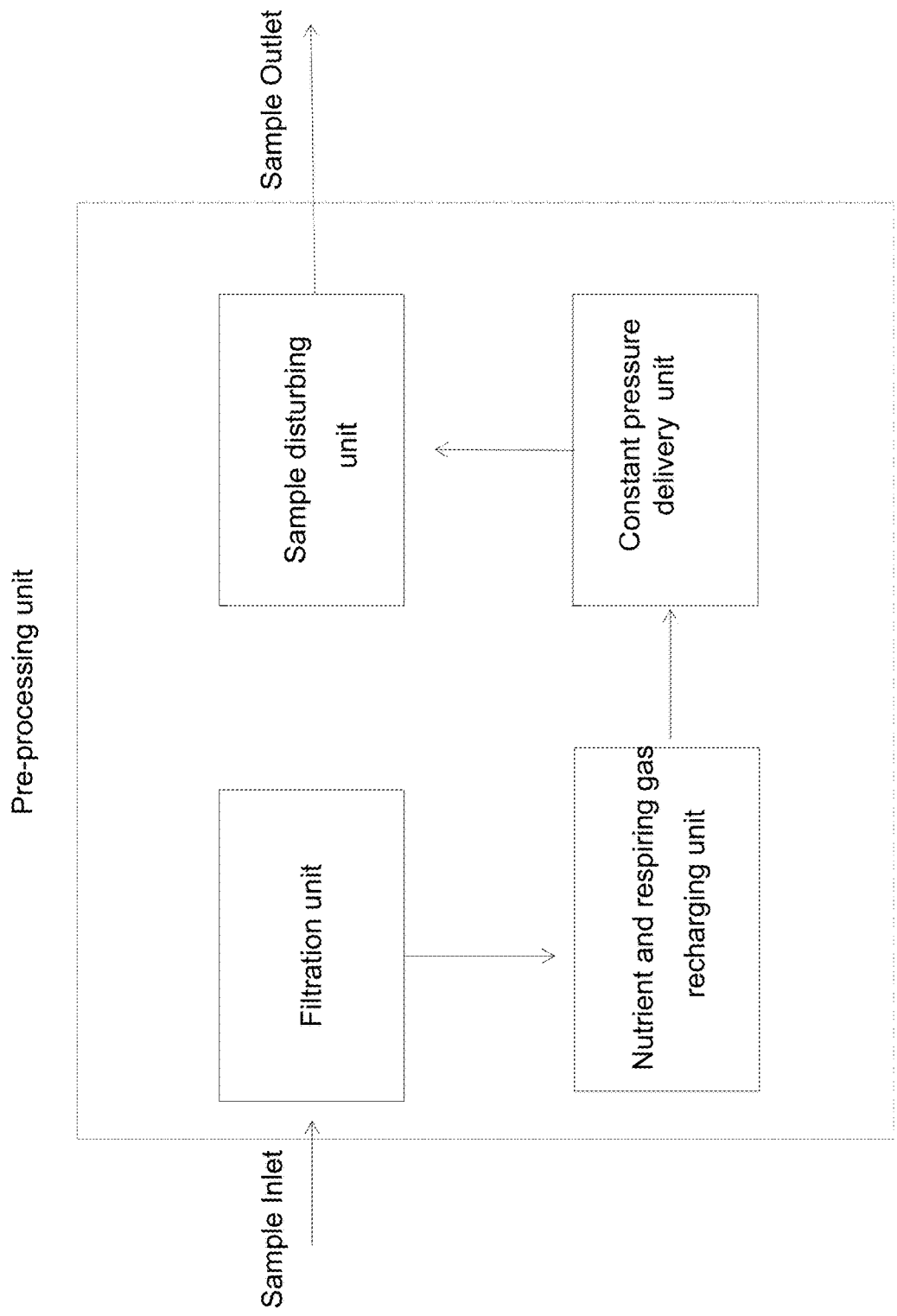

FIG. 38 is a diagram of a pre-processing unit of an apparatus of this invention.

Figure 39:
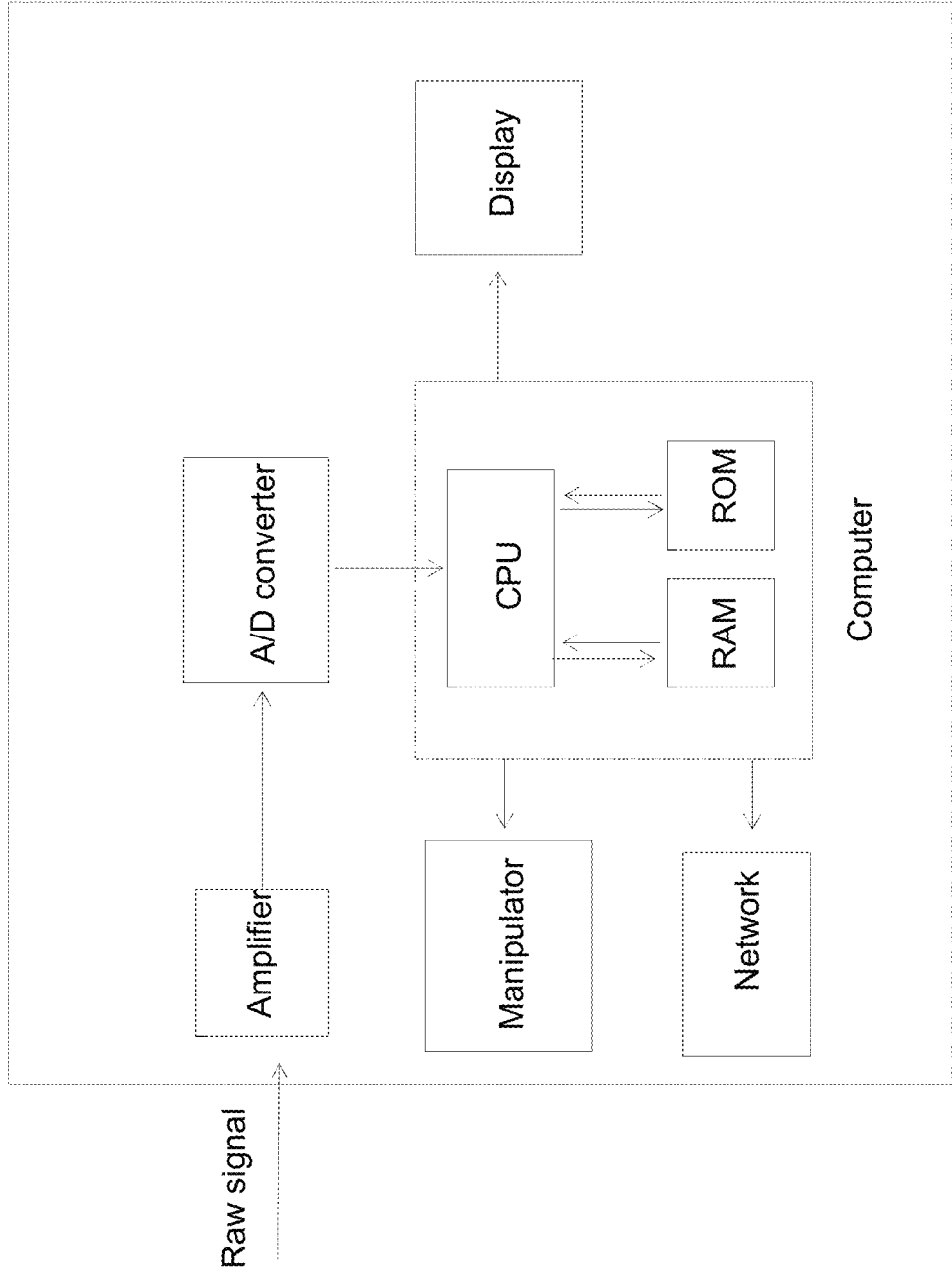

FIG. 39 is a diagram of an information processing unit of an apparatus of this invention.

Figure 40:
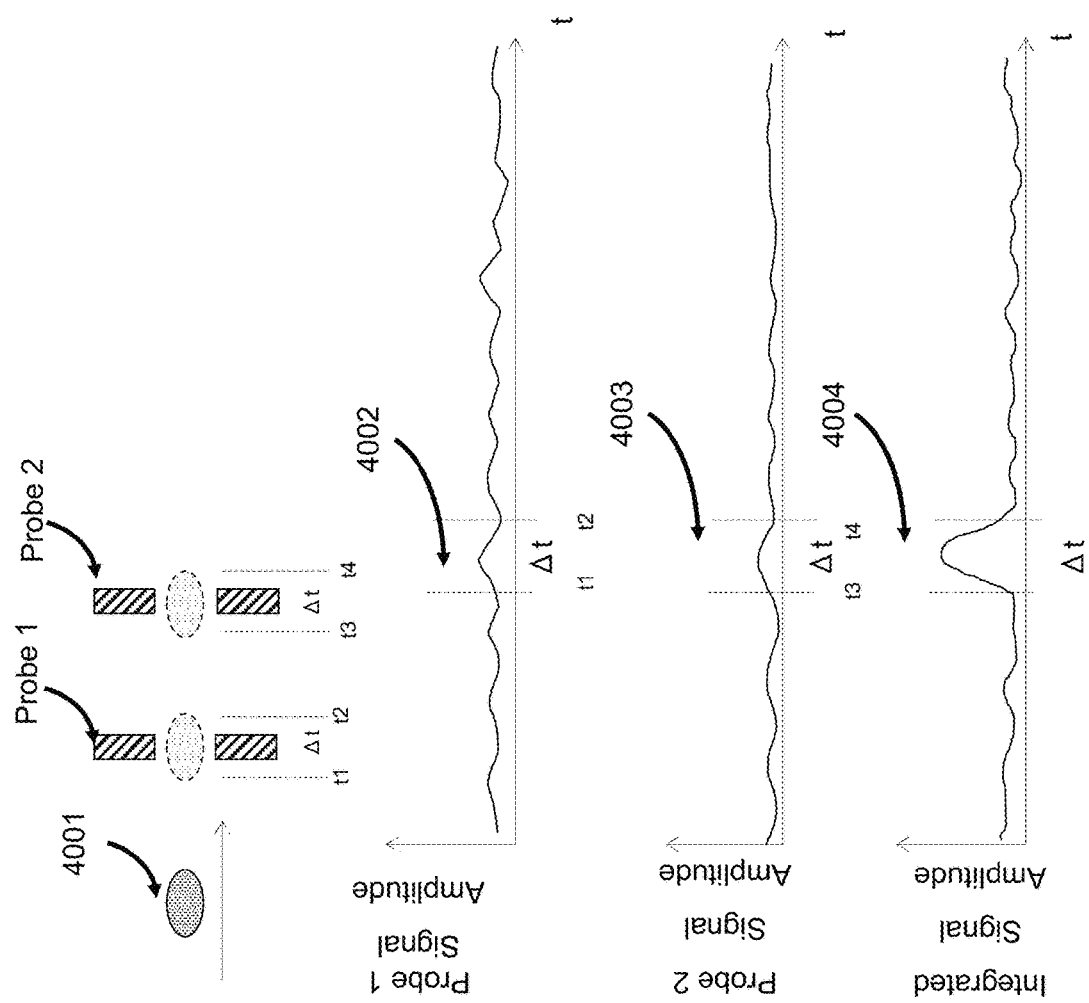

FIG. 40 shows the integration of multiple signals which results in cancellation of noise and enhancement of signal to noise ratio.

DETAILED DESCRIPTION OF THE INVENTION

One aspect of the present invention relates to apparatus for detecting CTCs in a biological entity in vivo or in vitro (e.g., human being, an organ, a tissue, or cells in a culture). Each apparatus comprises a biological fluid delivering system, a pre-processing unit, a re-charging unit, a probing and detecting device, and a discharging unit. The apparatus is capable of measuring microscopic properties of a biological sample. By the constant pressure fluid delivery system, microscopic biological subjects can be delivered onto or into the pre-processing or diagnostic micro-device of the apparatus. Compared to traditional detection apparatus or technologies, the apparatus provided by this invention are advantageous in providing enhanced detection sensitivity, specificity, functionalities, and speed, with reduced costs and size. The apparatus can further include a biological interface, a probing controlling and data analysis circuitry, or a system reclaiming or treating medical waste. Additional micro-devices, e.g., a second detection device, can also be included or integrated into the apparatus for enhanced detection capabilities.

As a key component of the apparatus, the micro-device should include means to perform at least the function of addressing, controlling, forcing, receiving, amplifying, analyzing, modifying, correcting, making decisions, or storing information from each probing address. As an example, such means can be a central control unit that includes a controlling circuitry, an addressing unit, an amplifier circuitry (such as a lock-in amplifier), a logic processing circuitry, a memory unit, an application specific chip, a signal transmitter, a signal receiver, a sensor, a unit for recycling and reclaiming the biological subject, a micro-electro-mechanical device, a multi-functional device, or a micro-instrument to perform surgery, drug delivery, cleaning, or medical function.

In some embodiments, the fluid delivering system comprises a pressure generator, a pressure regulator, a throttle valve, a pressure gauge, and distributing kits. As examples of these embodiments, the pressure generator can include a motor piston system and a bin containing compressed gas; the pressure regulator (which can consist of multiple regulators) can down-regulate or up-regulate the pressure to a desired value; the pressure gauge feeds back the measured value to the throttle valve which then regulates the pressure to approach the target value.

The biological fluid to be delivered can be a sample of a biological entity to be detected for disease or something not necessarily to be detected for disease. In some embodiments, the fluid to be delivered is liquid (e.g., a blood sample, a urine sample, a saliva sample, a tear sample, a sweat sample, or a lymph sample). The pressure regulator can be a single pressure regulator or multiple pressure regulators which are placed in succession to either down-regulate or up-regulate the pressure to a desired level, particularly when the initial pressure is either too high or too low for a single regulator to adjust to the desired level or a level that is acceptable for an end device or target.

In some other embodiments, the system controller includes a pre-amplifier, a lock-in amplifier, an electrical meter, a thermal meter, a switching matrix, a system bus, a nonvolatile storage device, a random access memory, a processor, or a user interface. The interface can include a sensor which can be an optical sensor, a voltage meter, a current meter, an electrical sensor, a pH meter, a hardness measurement sensor, a thermal sensor, a flow meter, a piezo-meter, or another type of sensor.

In still some other embodiments, apparatus of this invention further include a biological interface, a system controller, a system for reclaiming or treatment medical waste. The reclaiming and treatment of medical waste can be performed by the same system or two different systems.

Another aspect of this invention provides apparatus for interacting with a cell, which include a device for sending a signal to the cell and optionally receiving a response to the signal from the cell.

In some embodiments, the interaction with the cell can be probing, detecting, sorting, communicating with, treating, or modifying with a coded signal that can be an electric, magnetic, electro-magnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical signal, or a combination thereof.

In some other embodiments, the device contained in the apparatus can include multiple surfaces coated with one or more elements or combinations of elements, and a control system for releasing the elements. In some instances, the control system can cause release of the elements from the device surface via an energy including but not limited to thermal energy, optical energy, acoustic energy, electrical energy, electro-magnetic energy, magnetic energy, radiation energy, chemical energy, or mechanical energy in a controlled manner. The energy can be in the pulsed form at desired frequencies.

In some other embodiments, the device contained in the apparatus includes a first component for storing or releasing one element or a combination of elements onto the surface of the cell or into the cell; and a second component for controlling the release of the elements (e.g., a circuitry for controlling the release of the elements). The elements can be a biological component, a chemical compound, ions, catalysts, Ca, C, Cl, Co, Cu, H, I, Fe, Mg, Mn, N, O, P, F, K, Na, S, Zn, or a combination thereof. The signal, pulsed or constant, can be in the form of a released element or combination of elements, and it can be carried in a liquid solution, gas, or a combination thereof. In some instances, the signal can be at a frequency ranging from about $1\times10^{-4}$ Hz to about 100 MHz or ranging from about $1\times10^{-4}$ Hz to about 10 Hz, or at an oscillation concentration ranging from about 1.0 nmol/L to about 10.0 mmol/L. Also, the signal comprises the oscillation of a biological component, a chemical compound, Ca, C, Cl, Co, Cu, H, I, Fe, Mg, Mn, N, O, P, F, K, Na, S, Zn, or a combination thereof, e.g., at desired oscillating frequencies.

In some embodiments, the signal to be sent to the cell can be in the form of oscillating element, compound, or an oscillating density of a biological component, and a response to the signal from the cell is in the form of oscillating element, compound, or an oscillating density of a biological component.

In some embodiments, the device can be coated with a biological film, e.g., to enhance compatibility between the device and the cell.

In some other embodiments, the device can include components for generating a signal to be sent to the cell, receiving a response to the signal from the cell, analyzing the response, processing the response, and interfacing between the device and the cell (including communications between the device and the cell), and modifying or correcting certain aspects of the cell.

Still another aspect of this invention provides devices each including a micro-filter, a shutter, a cell counter, a selector, a micro-surgical kit, a timer, and a data processing circuitry. The micro-filter can discriminate abnormal cells by a physical property (e.g., dimension, shape, or velocity), mechanical property, electric property, magnetic property, electro-magnetic, thermal property (e.g., temperature), optical property, radiation property, acoustical property, biological property, chemical property, electro-chemical property, bio-chemical property, bio-physical property, fluid property, bio-electro-chemical property, bio-electro-mechanical property, or electro-mechanical property. In addition, information (such as pressure on the filer, flow rate through the filter, viscosity, temperature change, and adhesion with the filter), which can be in the form of static and dynamic information, can be obtained from interactions between the biological entity to be probed and the filter. The devices each can also include one or more micro-filters. Each of these micro-filters can be integrated with two cell counters, one of which is installed at the entrance of each filter well, while the other is installed at the exit of each filter well. The shape of the micro-filter's well is rectangle, ellipse, circular, or polygon; and the micro-filter's dimension ranges from about 0.1 μm to about 500 μm or from about 5 um to about 200 um. As used herein, the term "dimension" means the physical or feature size of the filter opening, e.g., diameter, length, width, or height. The filter can be coated with a biological or bio-compatible film, e.g., to enhance compatibility between the device and the cell.

In addition to separation of biological entity by its size and other physical features, the filter can also contain additional features and functions to perform biological entity separation via other properties, which comprise of mechanical property, electric property, magnetic property, electro-magnetic, thermal property (e.g., temperature), optical property, radiation property, acoustical property, biological property, chemical property, electro-chemical property, bio-chemical property, bio-electro-chemical property, bio-electro-mechanical property, and electro-mechanical property.

In some embodiments of these devices, the shutter sandwiched by two filter membranes can be controlled by a timer (thus time shutter). The timer can be triggered by the cell counter. For instance, when a cell passes through the cell counter of the filter entrance, the clock is triggered to reset the shutter to default position, and moves at a preset speed towards the cell pathway, and the timer records the time as the cell passes through the cell counter at the exit.

Still a further aspect of this invention provides methods for fabricating a micro-device with micro-trench and probe embedded in the micro-trench's sidewalls. A micro-trench is an unclosed tunnel (see, e.g., FIG. 2(i), 2030), which can be coupled with another upended symmetric trench (see, e.g., FIG. 2(k), 2031) to form a closed channel (see, e.g., FIG. 2(l), 2020). The invention can have an array of trenches. The method may include chemical vapor deposition, physical vapor deposition, or atomic layer deposition to deposit various materials on a substrate; patterning the deposited layer(s) utilizing methods comprising of lithography, etch, and chemical mechanical polishing to form desired features (such as a trench); chemical mechanical planarization for surface planarization; chemical cleaning for particle removal; diffusion or ion implantation for doping elements into specific layers; or thermal anneal to reduce the crystal defects and activate diffused ions. An example of such method includes: depositing a first material onto a substrate; depositing a second material onto the first material and patterning the second material by a microelectronic process (e.g., lithography, etch) to form a detecting tip; depositing a third material on the second material and then planarize the third material by a polishing process; depositing a fourth material on the third material and patterning the fourth material first by a microelectronic process (e.g., lithography, etch) and then by a microelectronic process (e.g., another etch) to remove a portion of the third material and optionally a portion of the first material while this etch is typically selective to the second material (lower etch rate for the second material), in which the fourth material serves as a hardmask. A hardmask generally refers to a material (e.g., inorganic dielectric or metallic compound) used in semiconductor processing as an etch mask in lieu of polymer or other organic "soft" materials. The probe can have a tip along side the trench. The tip matches spatially with either a major groove or a minor groove of DNA. For example, the tip matches spatially with interlaced grooves of DNA and the groove interval can be variable. The tip of the probe at the end of trench can also match the end of each strand of the DNA helix. The tip's diameter ranges from about 1 angstrom to about 10 μm.

In some embodiments, the method further includes coupling two devices that are thus fabricated and symmetric (i.e., a flipped mirror) to form a detecting device with channels. The entrance of each channel can be optionally bell-mouthed, e.g., such that the size of channel's opening end (the entrance) is larger than the channel's body, thereby making it easier for a cell to enter the channel. The shape of each channel's cross-section can be rectangle, ellipse, circle, or polygon. The micro-trenches of the coupled two micro-devices can be aligned by the module of alignment marks designed on the layout of the micro-device. The dimension of the micro-trench can range from about 0.1 um to about 500 um. The width of the micro-trench ranges from about 0.5 nm to about 200 μm (e.g., from about 0.5 nm to about 50 μm), the depth of the micro-trench ranges from about 0.5 nm to about 200 μm (e.g., from about 0.5 nm to about 50 μm), and the length of the micro-trench ranges from about 1 nm to about 10 mm. The shapes and sizes of different sections of the channel can be the same or different.

Alternatively, the method can also include covering the micro-trench of the micro-device with a flat panel. Such a panel can comprise or be made with silicon, SiGe, $SiO_2$, $Al_2O_3$, quartz, low optical loss glasses, or other optical materials. Examples of other potentially suitable optical materials include acrylate polymer, AgInSbTe, synthetic alexandrite, arsenic triselenide, arsenic trisulfide, barium fluoride, CR-39, cadmium selenide, caesium cadmium chloride, calcite, calcium fluoride, chalcogenide glass, gallium phosphide, GeSbTe, germanium, germanium dioxide, glass code, hydrogen silsesquioxane, Iceland spar, liquid crystal, lithium fluoride, lumicera, METATOY, magnesium fluoride, magnesium oxide, negative index metamaterials, neutron supermirror, phosphor, picarin, poly(methyl methacrylate), polycarbonate, potassium bromide, sapphire, scotophor, spectralon, speculum metal, split-ring resonator, strontium fluoride, yttrium aluminium garnet, yttrium lithium fluoride, yttrium orthovanadate, ZBLAN, zinc selenide, and zinc sulfide.

In other embodiments, the method can further include integrating three or more micro-devices thus fabricated to yield an enhanced device with an array of the channels.

Another aspect of this invention relates to a set of novel process flows for fabricating micro-devices (including micro-probes and micro-indentation probes) for their applications in CTC detection by measuring microscopic properties of a biological sample. The micro-devices can be integrated into a CTC detection apparatus of this invention to measure one or more properties at microscopic levels. For example, a cancerous cell may have a different hardness (harder), density (denser), and elasticity than a normal cell.

Another aspect of this invention is to involve in cellular communications and regulate cellular decision or response (such as differentiation, dedifferentiation, cell division and cell death) with fabricated signals generated by the micro-devices disclosed herein. This could be further employed to detect and treat diseases.

To further enhance measurement capabilities, multiple micro-devices can be implemented into a piece of detection apparatus employing the time of flight technique, in which at least one probing micro-device and one sensing micro-device placed at a preset, known distance. The probing micro-device can apply a signal (e.g., a voltage, a charge, an electrical field, a laser beam, a thermal pulse, a train of ions, or an acoustic wave) to the biological sample to be measured, and the detection (sensing) micro-device can measure response from or of the biological sample after the sample has traveled a known distance and a desired period of time. For instance, a probing micro-device can apply an electrical charge to a cell first, and then a detection (sensing) micro-device subsequently measures the surface charge after a desired period of time (T) has lapsed and the cell has traveled a certain distance (L).

The micro-devices contained in the apparatus of this invention can have a wide range of designs, structures, functionalities, flexibilities, and applications due to their diverse properties, high degree of flexibilities, and ability of integration, miniaturization, and manufacturing scalability. They include, e.g., a voltage comparator, a four point probe, a calculator, a logic circuitry, a memory unit, a micro cutter, a micro hammer, a micro shield, a micro dye, a micro pin, a micro knife, a micro needle, a micro thread holder, micro tweezers, a micro laser, a micro optical absorber, a micro mirror, a micro wheeler, a micro filter, a micro chopper, a micro shredder, micro pumps, a micro absorber, a micro signal detector, a micro driller, a micro sucker, a micro tester, a micro container, a signal transmitter, a signal generator, a friction sensor, an electrical charge sensor, a temperature sensor, a hardness detector, an acoustic wave generator, an optical wave generator, a heat generator, a micro refrigerator and a charge generator.

Further, it should be noted that advancements in manufacturing technologies have now made fabrications of a wide range of micro-devices and integration of various functions onto the same device highly feasible and cost effective. The typical human cell size is about 10 microns. Using state-of-the-art integrated circuit fabrication techniques, the minimum feature size defined on a micro-device can be as small as 0.1 micron or below. Thus, it is ideal to utilize the disclosed micro-devices for biological applications.

In terms of materials for the micro-devices, the general principle or consideration is the material's compatibility with a biological entity. Since the time in which a micro-device is in contact with a biological sample (e.g., a cell) may vary, depending on its intended application, a different material or a different combination of materials may be used to make the micro-device. In some special cases, the materials may dissolve in a given pH in a controlled manner and thus may be selected as an appropriate material. Other considerations include cost, simplicity, ease of use and practicality. With the significant advancements in micro fabrication technologies such as integrated circuit manufacturing technology, highly integrated devices with minimum feature size as small as 0.1 micron can now be made cost-effectively and commercially. One good example is the design and fabrication of micro electro mechanical devices (MEMS), which now are being used in a wide variety of applications in the electronics industry and beyond.

Set forth below are several illustrations or examples of apparatus of this invention containing a class of innovative micro-devices that are integrated into the disease detection apparatus of this invention, and of their fabrication process.

Figure 1:
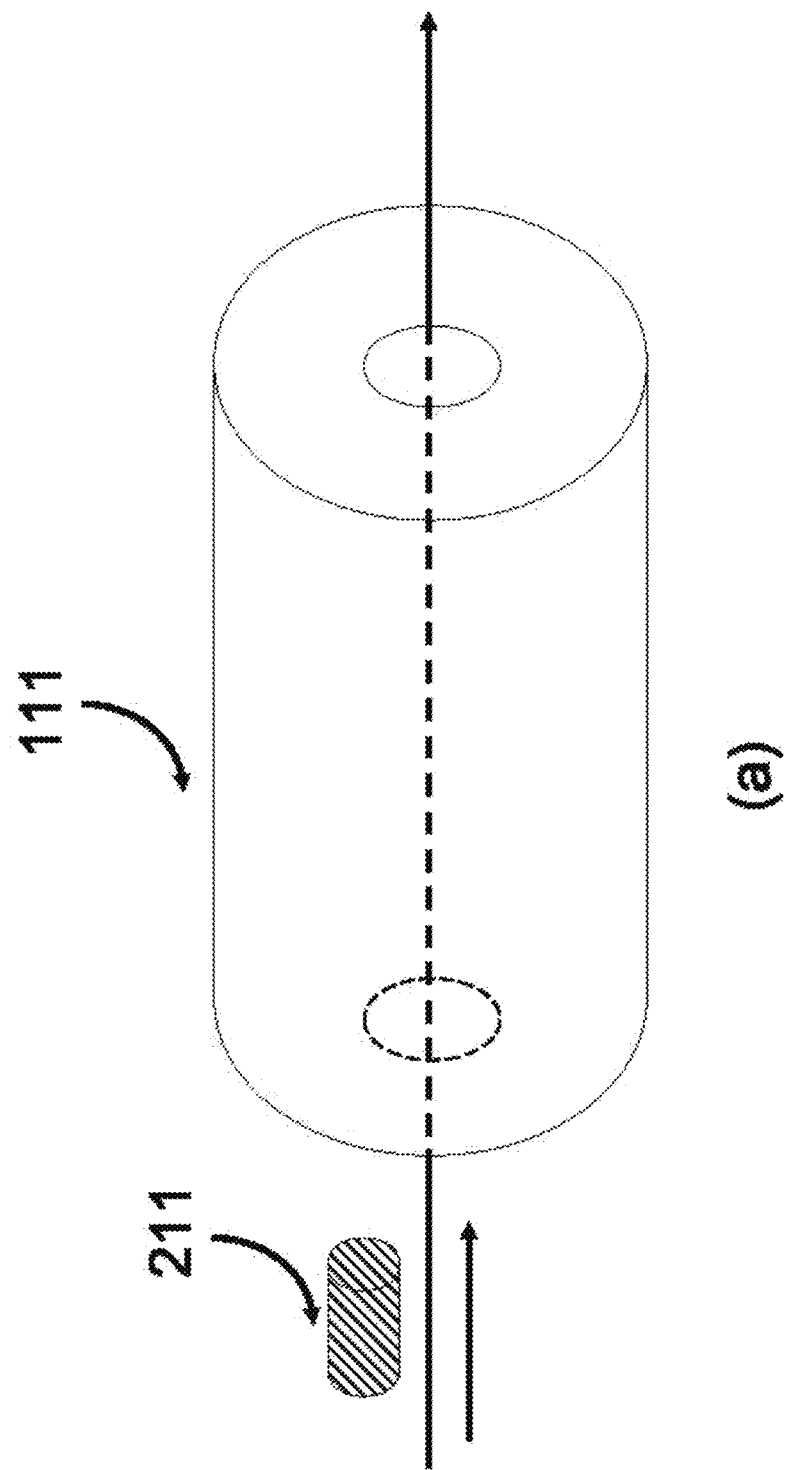
Figure 1:
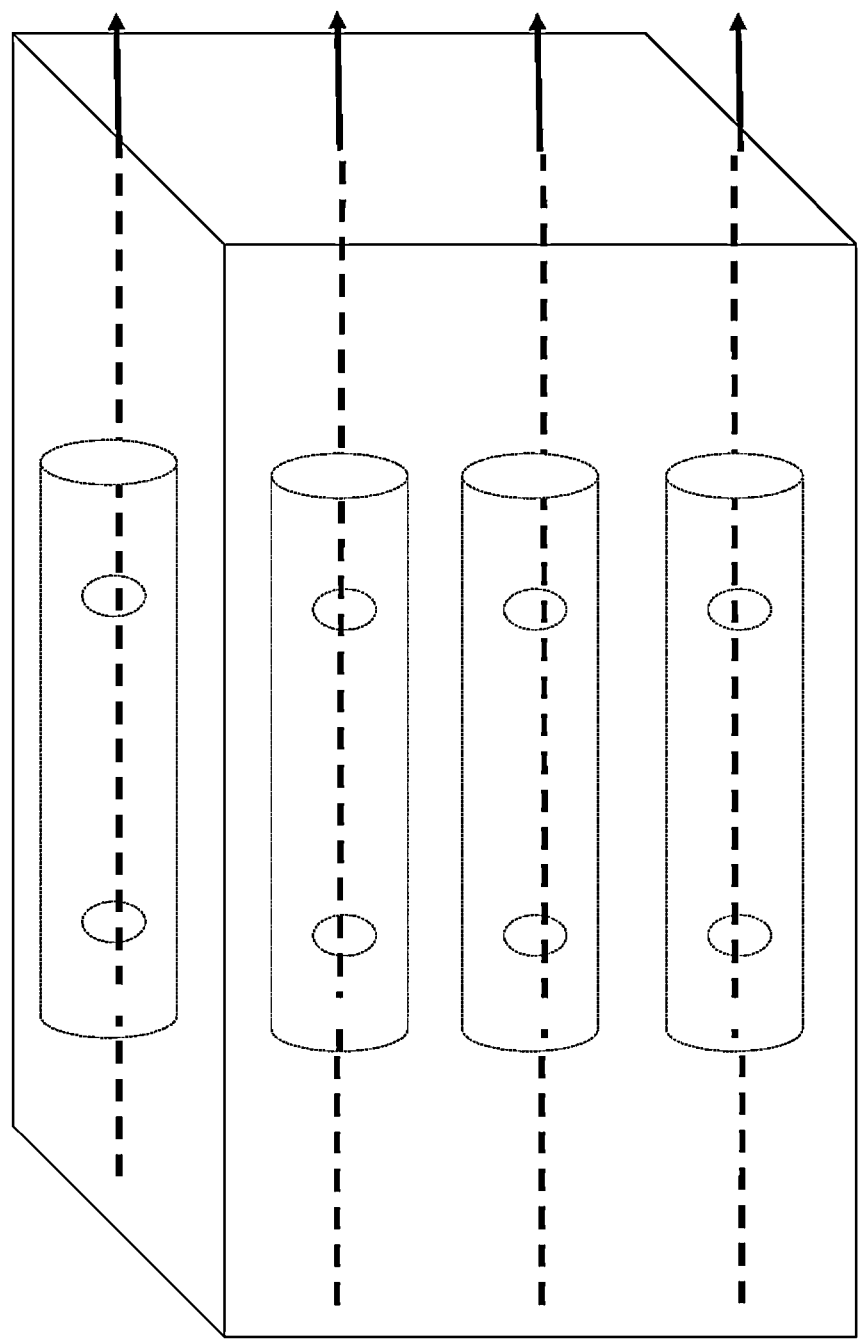
Figure 1:
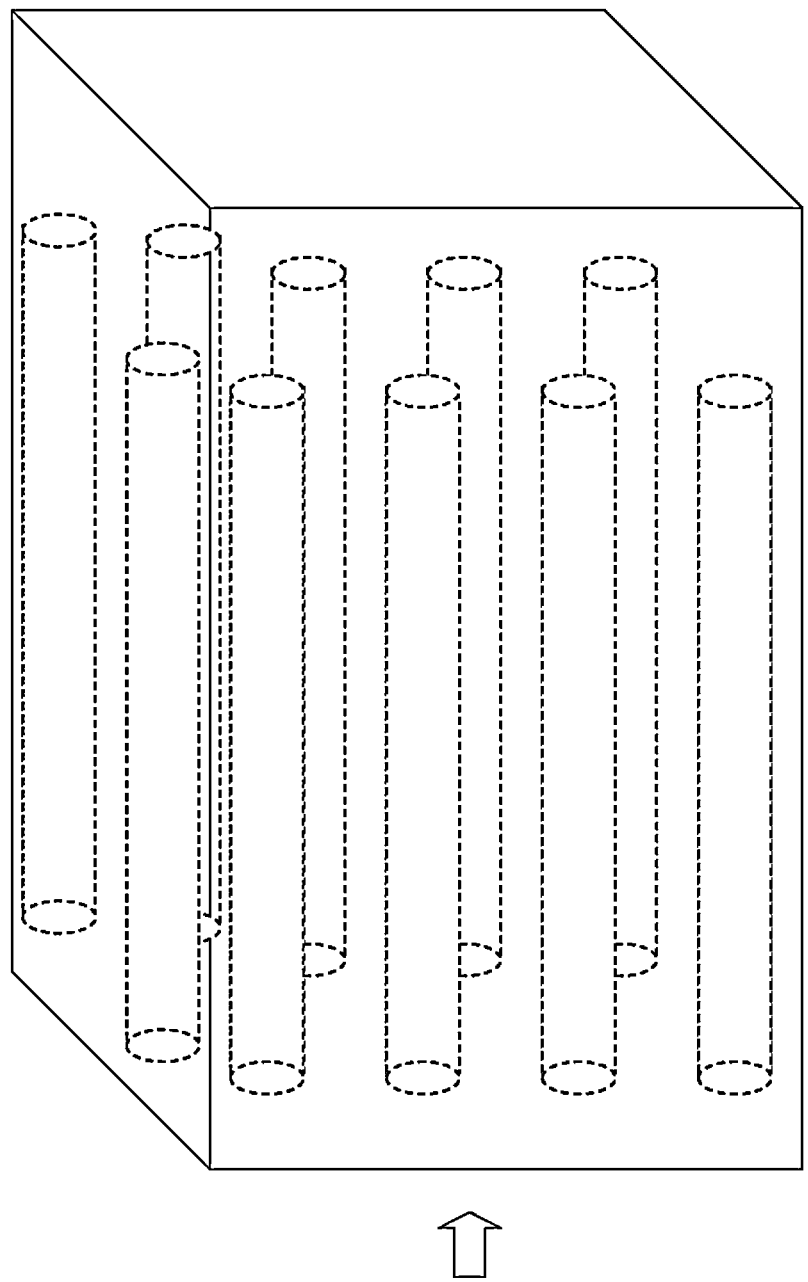

FIG. 1 is a perspective illustration of a CTC detection apparatus of this invention 111 in which a biological sample 211 such as a blood sample placed in it or moving through it is tested. In this figure, an example of disease detection apparatus 111 is in the form of a cylinder, in which a biological sample 211 flowing through it (from the left side to the right side in the figure) can be tested for one or more properties at the microscopic levels.

To enhance detection speed and sensitivity, a large number of micro-devices can be integrated into a single CTC detection apparatus of this invention, such as the apparatus illustrated in FIG. 1(b) and FIG. 1(c) with the micro-devices spaced to measure a large number of desired entities (such as cells.) in the biological sample. To achieve the above requirements, the detection apparatus should be optimized with its surface area maximized to contact the biological sample and with large number of micro-devices integrated on the maximized surface.

Figure 2:
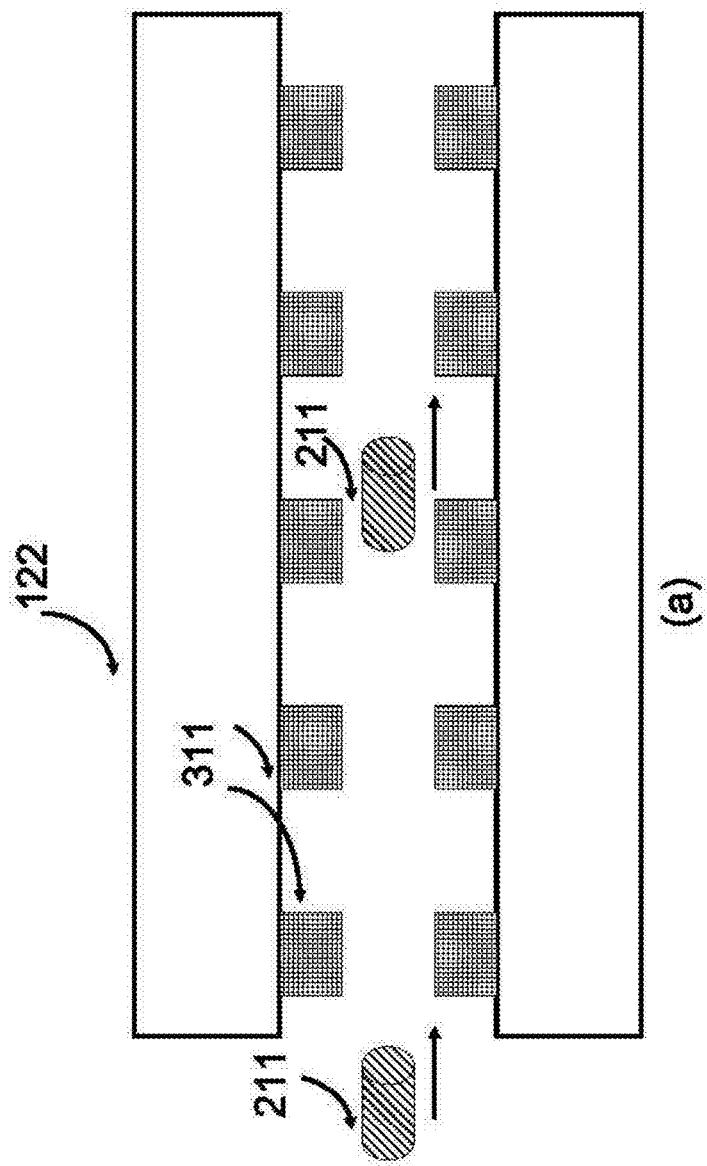
Figure 2:
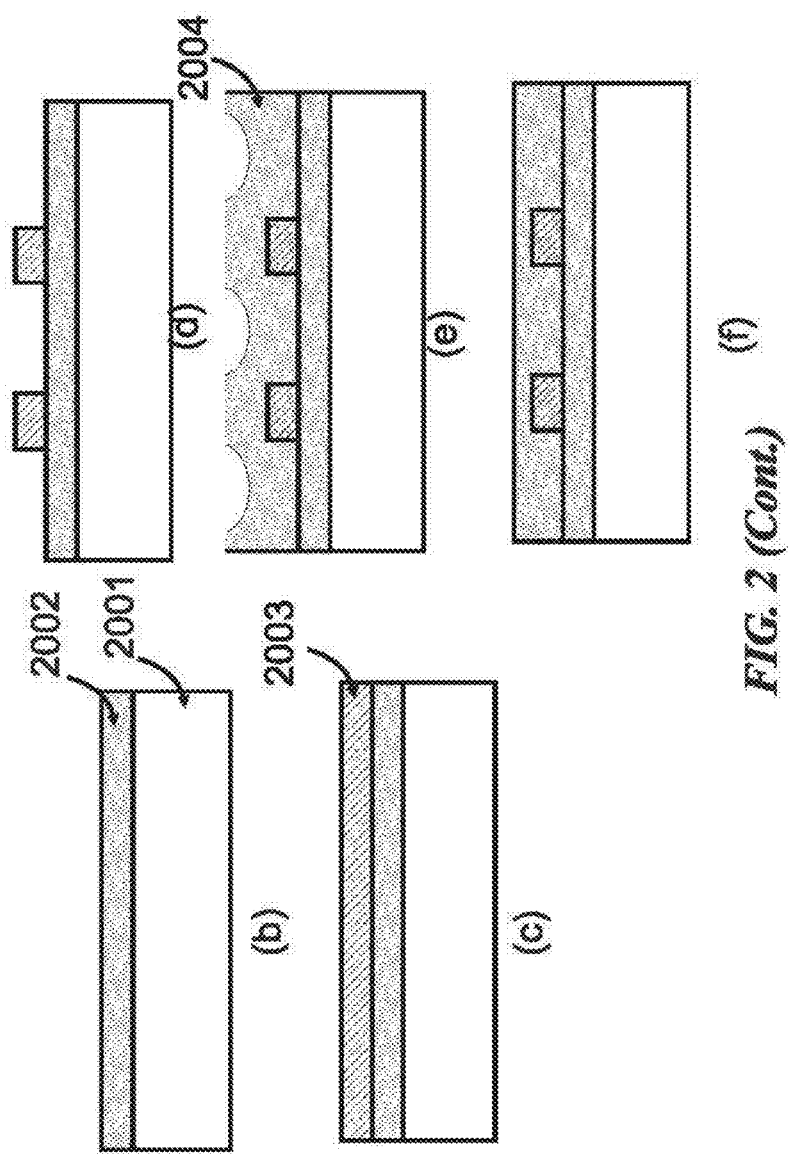
Figure 2:
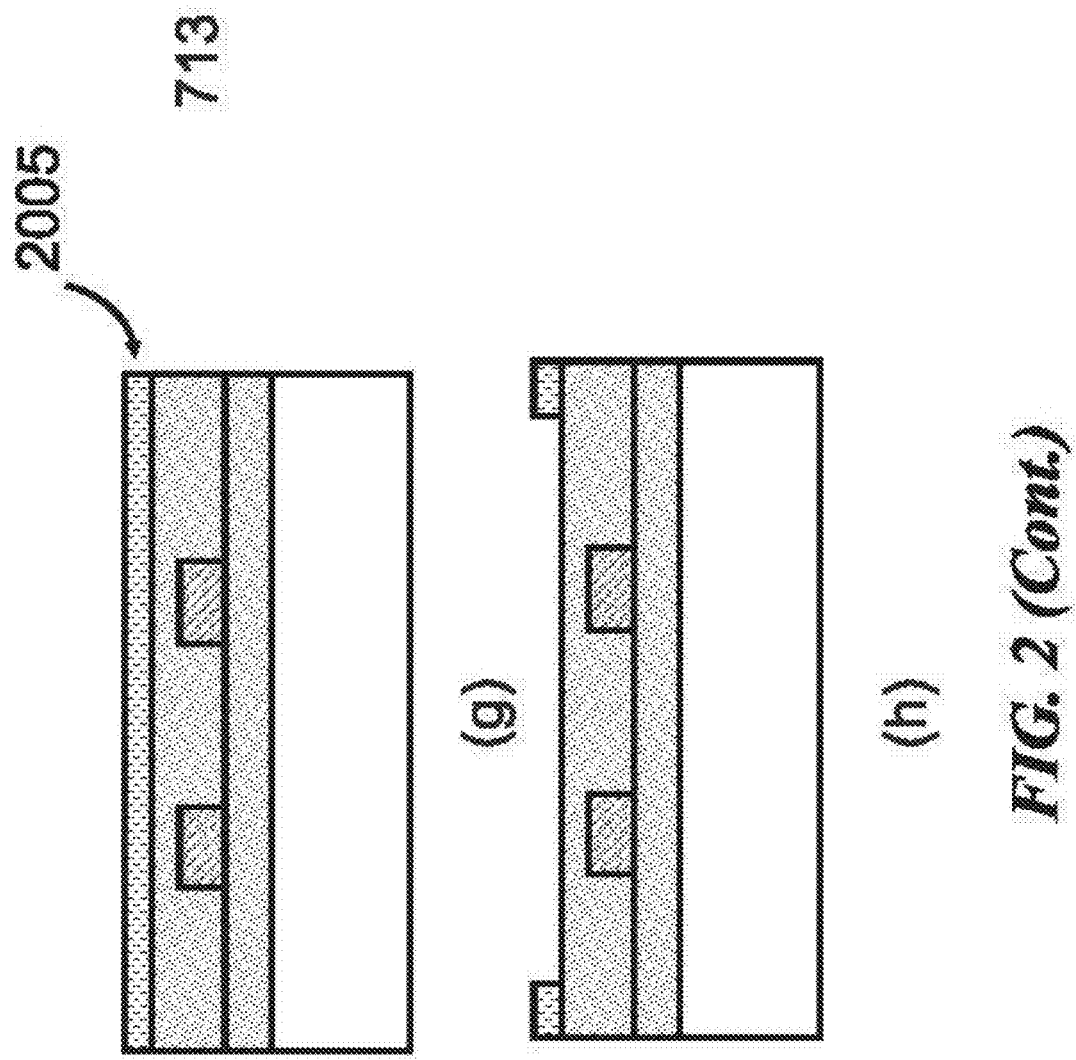
Figure 2:
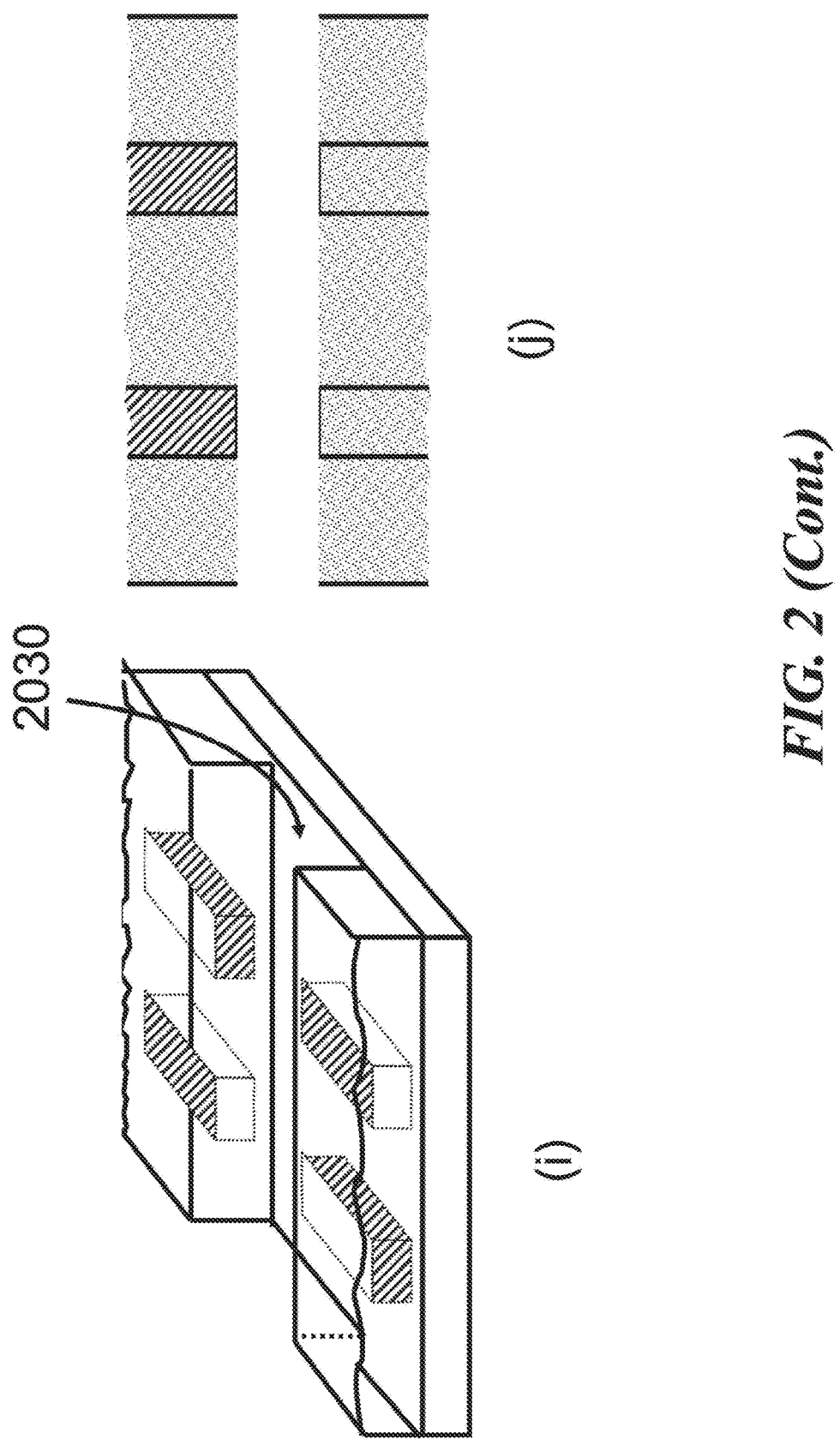
Figure 2:
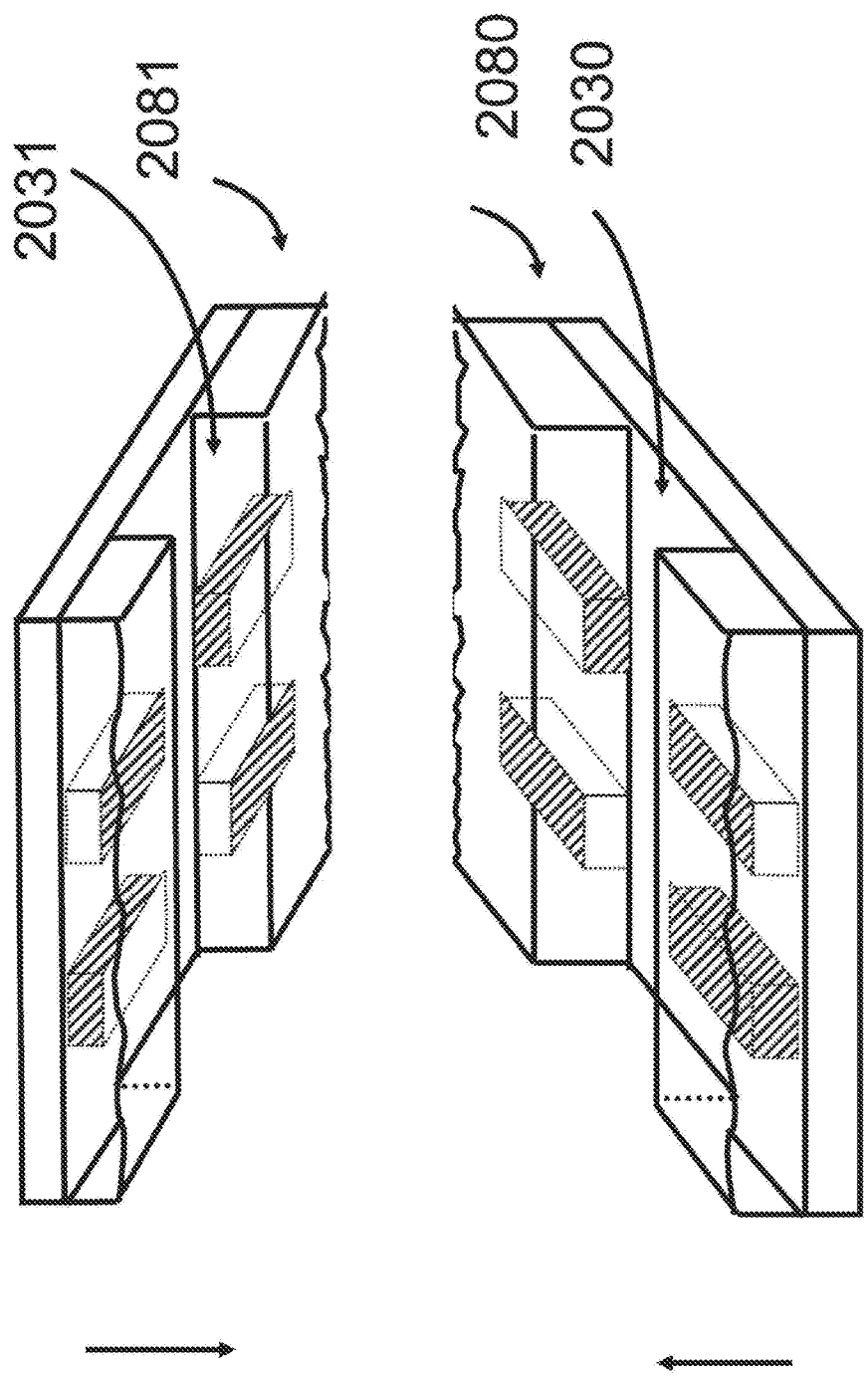
Figure 2:
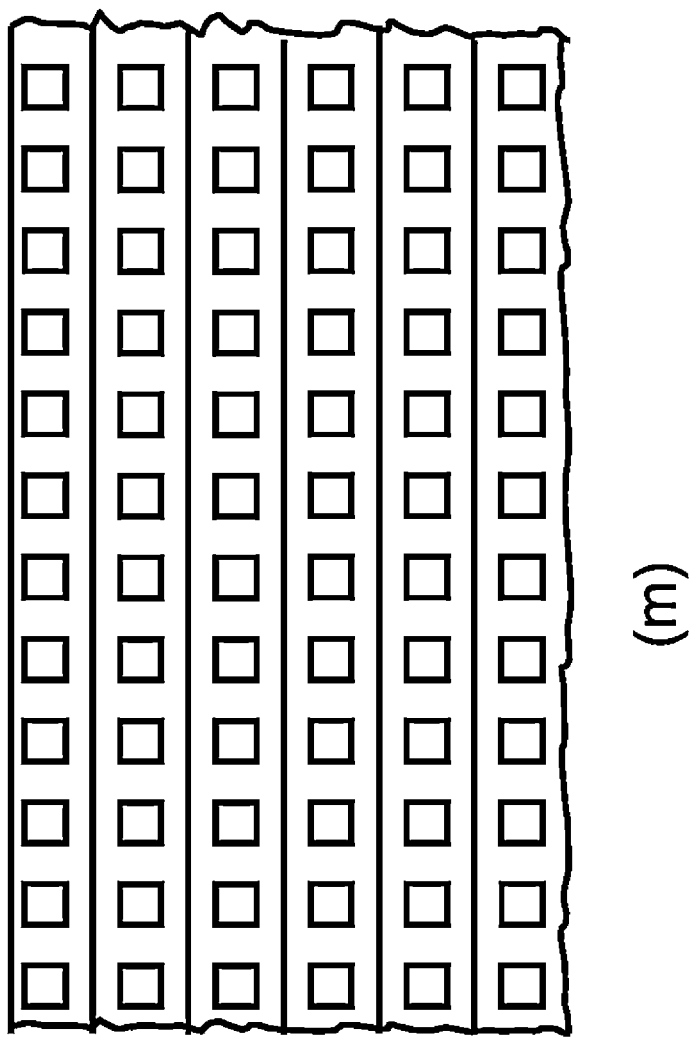
Figure 2:
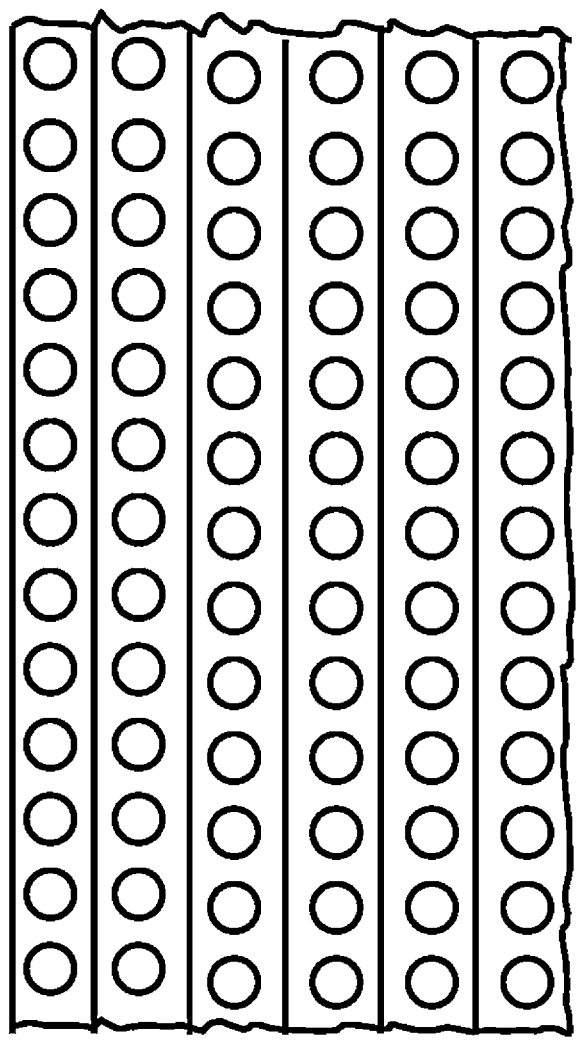

FIG. 2 (a) is a perspective, cross-sectional illustration of a CTC detection apparatus of this invention 122 with multiple identical micro-devices 311. A biological sample such as a blood sample 211 placed in it or moving through it can be tested for one or more properties at the microscopic levels including, e.g., electrical properties (such as surface charge, surface potential, current, impedance, other electrical properties), magnetic properties, electromagnetic properties, mechanical properties (such as density, hardness, shear strength, elongation strength, fracture tress, and adhesion), biological features, chemical properties (e.g., pH or ionic strength), biochemical properties, thermal properties (e.g., temperature), optical properties, and radiation properties.

Figure 3:
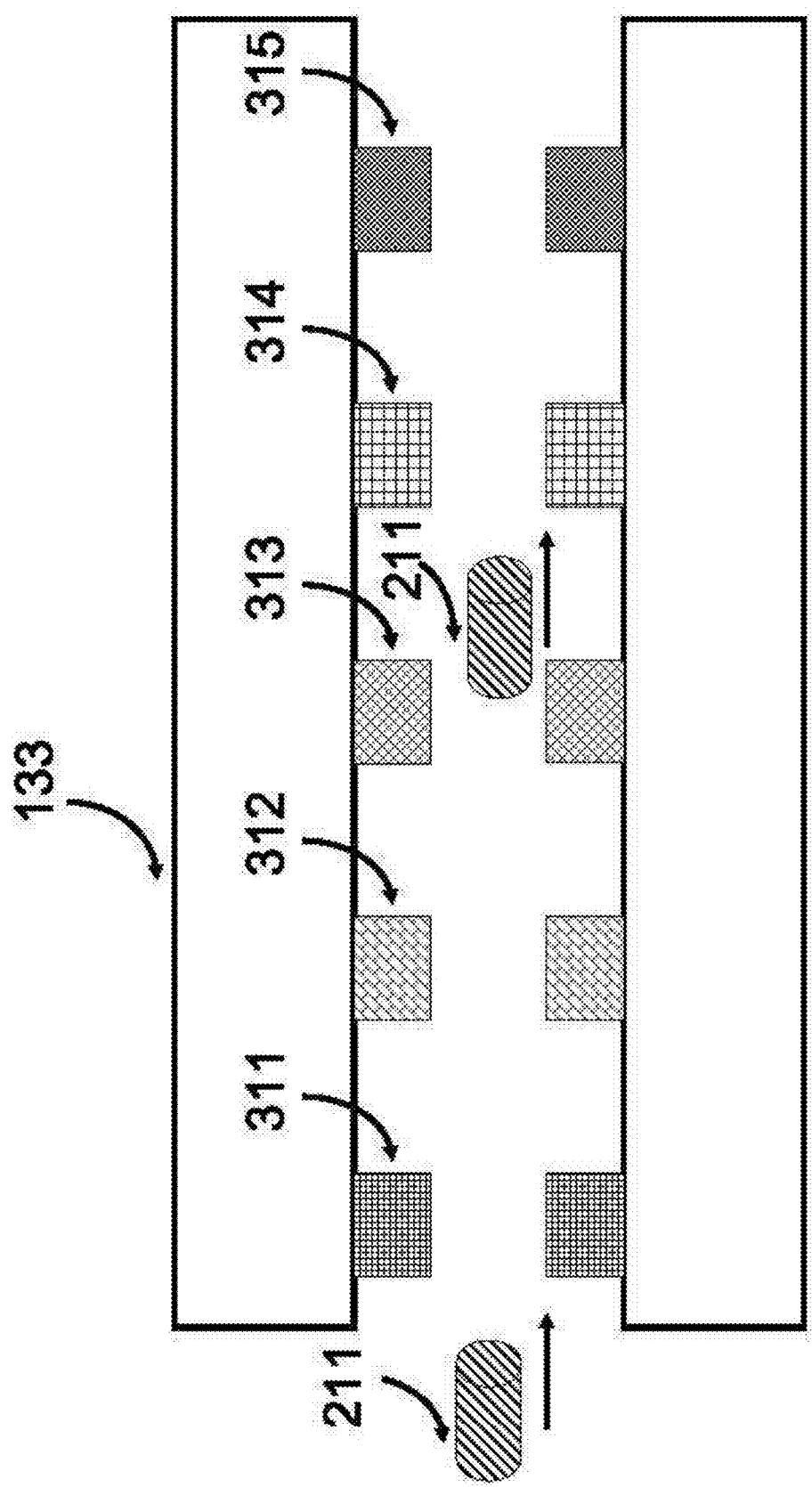
FIG. 3 is a perspective, cross-sectional illustration of a CTC detection apparatus of this invention with multiple micro-devices of different detection probes. A biological sample is placed in the apparatus or moving through it and one or more microscopic properties of this sample are measured with the multiple micro-device.

Instead of measuring a single property of a biological entity for CTC diagnosis, various micro-devices can be integrated into a detection apparatus to detect multiple properties. FIG. 3 is a perspective, cross-sectional illustration of a CTC detection apparatus of this invention 133 with multiple micro-devices 311, 312, 313, 314, and 315, of different detection probes in which a sample 211 such as a blood sample placed in it or moving through it can be tested for multiple properties including but not limited to electrical properties (e.g., surface charge, surface potential, and impedance), magnetic properties, electromagnetic properties, mechanical properties (e.g., density, hardness and adhesion), thermal properties (e.g., temperature), biological properties, chemical properties (e.g., pH), physical properties, acoustical properties, optical properties, and radiation properties.

FIGS. 2(b)-2(n) illustrate a process flow of this invention for fabricating micro-devices for trapping, sorting, probing, measuring, and modifying biological entities (e.g., a single cell). First, a material 2002 (e.g., a non-conducting material) and another material 2003 (e.g., a conducting material) are sequentially deposited on a substrate 2001 (see FIG. 2(b) and FIG. 2(c)). The first material 2003 is then subsequently patterned by the lithography and etch processes (see FIG. 2(d)). Another material 2004 is then deposited (as shown in FIG. 2(e)) and planarized (as shown in FIG. 2(f)). Another layer of material 2005 is deposited (as shown in FIG. 2(g)) and patterned as a hard mask (as shown in FIG. 2(h)), then followed by etch (as shown in FIG. 2(j)), which is stopped on the substrate 2001. FIG. 2(i) is a perspective illustration of the device, while FIG. 2(j) is a vertical illustration of the device.

As shown in FIG. 2(k), the device 2080 and a mirrored or symmetric device 2081 can be coupled together (as shown in FIG. 2. (l)). As such, the apparatus having the pathway with probe embedded in the sidewall is fabricated.

As illustrated in FIG. 2(m) and FIG. 2(n), a large number of detection micro-devices can be integrated together to enhance the detection efficiency.

Figure 4:
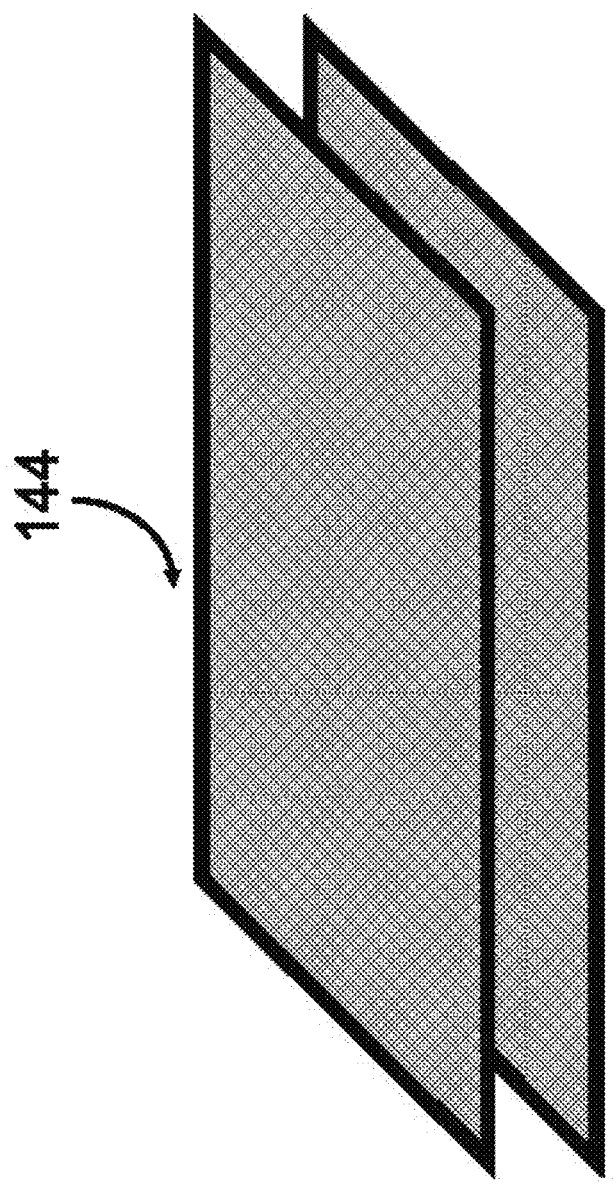
FIG. 4 is a perspective illustration of a CTC detection apparatus of this invention. It includes two slabs separated by a narrow spacing with a biological sample to be analyzed placed between the slabs, with multiple micro-devices placed at the inner surfaces of the slabs to measure one or more desired parameters of the sample at microscopic levels.

As illustrated herein, it is desirable to optimize the detection apparatus design to maximize measurement surface area, since the greater the surface area, the greater number of micro-devices that can be placed on the detection apparatus to simultaneously measure the sample, thereby increasing detection speed and also minimizing the amount of sample needed for the test. FIG. 4 is a perspective illustration of a disease detection apparatus of this invention 144. It includes two slabs separated by a narrow spacing with a sample such as a blood sample to be measured placed between the slabs, with multiple micro-devices placed at the inner surfaces of the slabs to measure one or more properties of the sample at microscopic levels.

Figure 5:
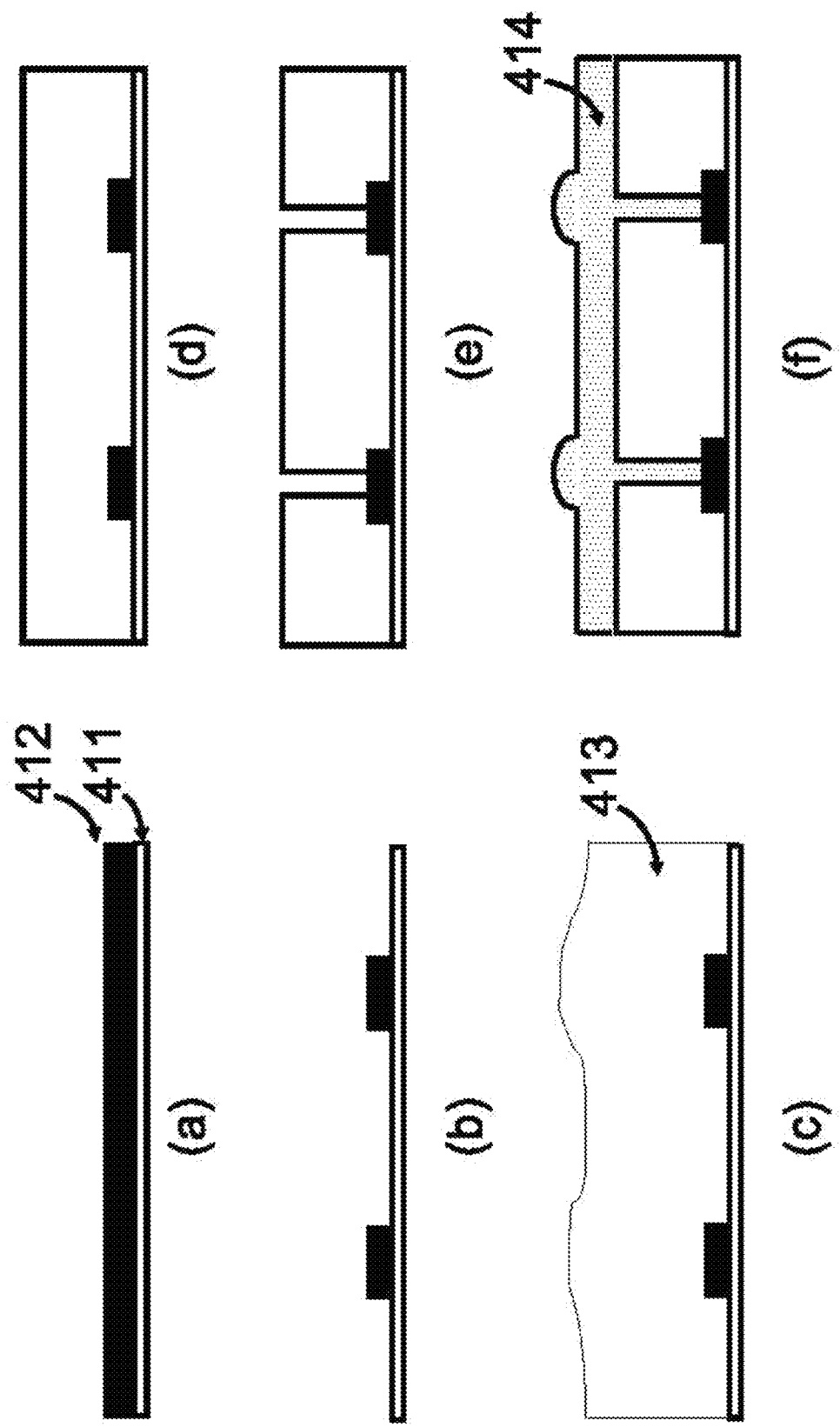
FIG. 5 illustrates a novel process flow for fabricating a CTC detection apparatus of this invention utilizing microelectronics technologies.
Figure 5:
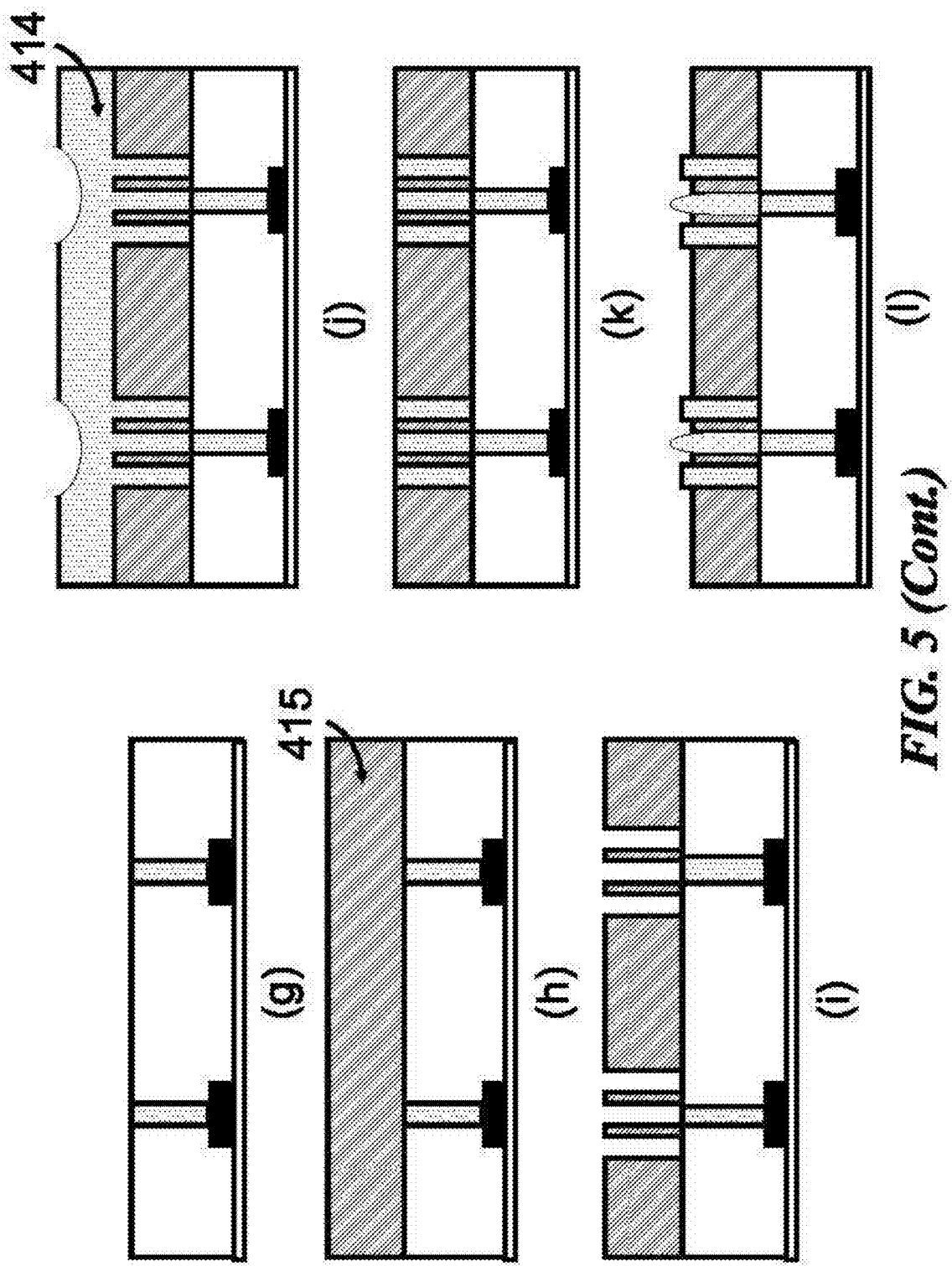

Yet another aspect of this invention relates to a set of novel fabrication process flows for making micro-devices for CTC detection purposes. FIG. 5 illustrates a novel process flow for fabricating a CTC detection apparatus utilizing microelectronics technologies and processes. First, a material 412 is deposited on a substrate 411 (FIG. 5(a)). It is then patterned by photolithography and etching processes (FIG. 5(b)). Following the deposition, material 413 is planarized using chemical mechanical polishing as shown in FIG. 5(d). Recessed areas, in the form of hole pattern, are next formed in material 413 using photolithography and etch processes, as shown in FIG. 5(e), followed by the deposition of material 414 (FIG. 5(f)). Material 414 above the surface of material 413 is removed by chemical mechanical polishing (FIG. 5(g), followed by deposition of material 415. Material 415 is next patterned using photolithography and etching processes (FIG. 5(i)). Material 414 is next deposited and its excess material above its substrate 415 is removed by chemical mechanical polishing (FIGS. 5(j) and (k)). Finally, a light etch or short chemical mechanical polishing to material 415 is carried out to recess material 415, selective to material 414 (FIG. 5(l)), resulting in slight protruding of material 414. Material 412 can be a piezoelectric material. When a voltage is applied to it in the right direction, it will expand and push up, resulting in upward motion in middle tip in material 414. Thus, a micro-device with two probes capable of measuring a range of properties (including mechanical and electrical properties) of biological samples is fabricated, using the above novel fabrication process flow.

Figure 6:
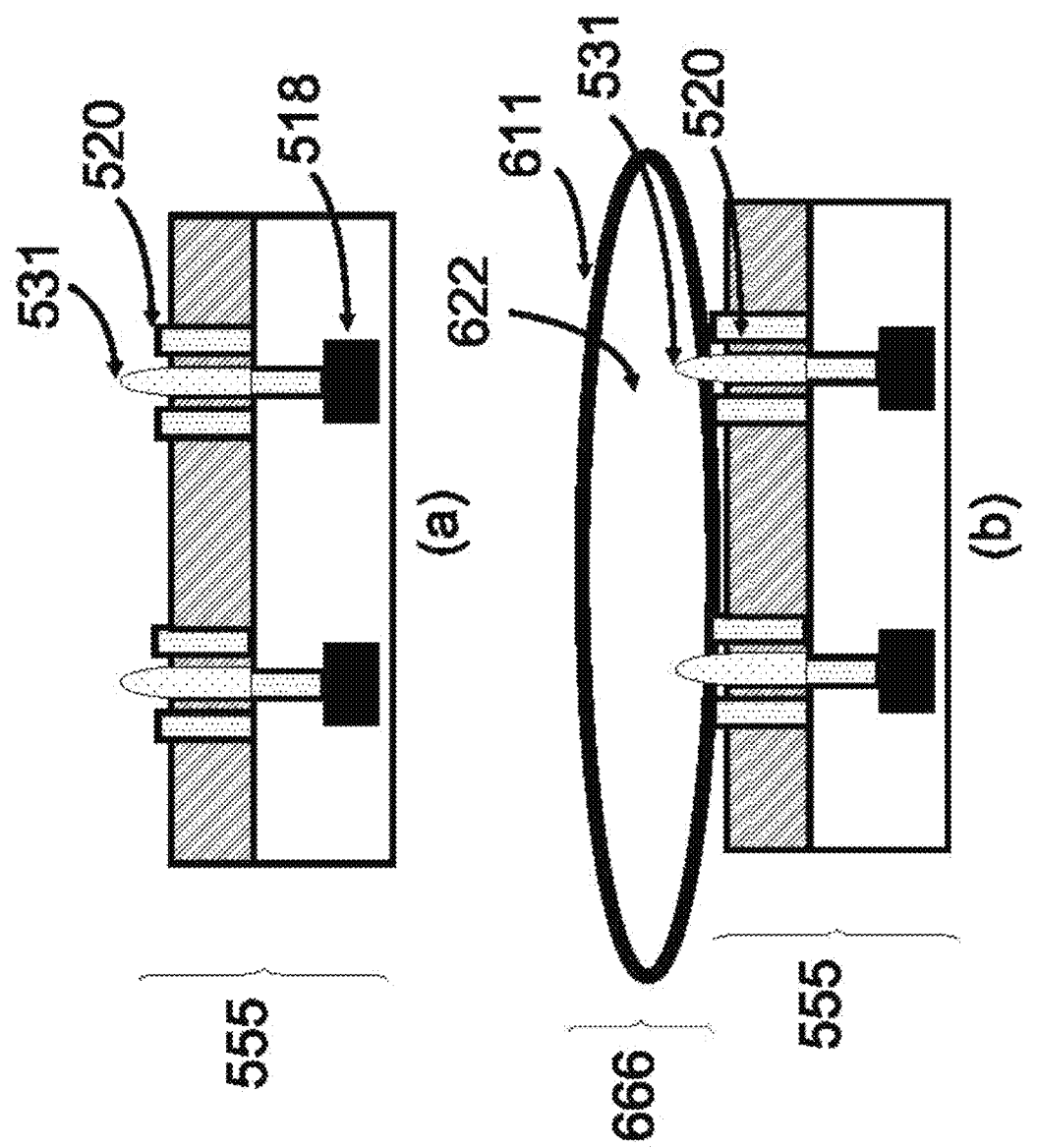
FIG. 6 is a perspective illustration of a CTC detection apparatus fabricated by a method of this invention. The apparatus is capable of probing a single cell and measuring its microscopic properties.

Detection apparatus integrated with micro-devices disclosed in this application is fully capable of detecting pre-chosen properties on a single cell. FIG. 6 is a perspective illustration of a micro-device 555 fabricated by a novel process flow disclosed in this patent application (e.g., novel process flow illustrated in FIG. 5 above) and how such a device is capable of probing a single cell 666 and measuring the cell for collecting intended parameters. FIG. 6(a) illustrated a perspective, cross-section of a micro-device 555 with a pair of micro probes 531 and 520, where micro probe 531 is in the form of a tip and micro probe 520 is in the form of a ring. Both of micro probes 531 and 520 can be conductive and they can serve as a pair of probes to measure electrical properties of a biological sample. Micro probe 531 is in contact with a base 518 which can be a piezoelectric material. When a voltage is applied to the base 518 made of a piezoelectric material, the base 518 can expand and push micro probe tip 531 upward, which can be useful in measuring various properties of a biological sample such as a single cell. In FIG. 6(b), micro-device 555 is shown to measure a single cell 666, using probe tip 531 penetrating through cell membrane 611 and into the cell's inner space 622, while probe ring 520 making contact with cell membrane 611 at the outside surface of the membrane. This way, the micro-device 555 can make various measurements on the cell, including its electrical properties (e.g., electrical potential, current across the cell membrane, surface charge on the membrane, and impedance), mechanical properties (e.g., hardness when probe tip 531 is designed as a micro-indentation probe), thermal properties (e.g., temperature), physical properties, and chemical properties (e.g., pH).

In another further aspect, the invention provides the design, integration, and fabrication process flow of micro-devices capable of making highly sensitive and advanced measurements on very weak signals in biological systems for CTC detection under complicated environment with very weak signal and relatively high noise background. Those novel capabilities using the class of micro-devices disclosed in this invention for CTC detection include but not limited to making dynamic measurements, real time measurements (such as time of flight measurements, and combination of using probe signal and detecting response signal), phase lock-in technique to reduce background noise, and 4-point probe techniques to measure very weak signals, and unique and novel probes to measure various electronic, electromagnetic and magnetic properties of biological samples at the single cell (e.g., a telomere of DNA or chromosome).

For example, in a time of flight approach to obtain dynamic information on the biological sample (e.g., a cell), a first micro-device is first used to send a signal to perturb the biological entity to be diagnosed, and then a second micro-device is employed to accurately measure the response from the biological entity. In one embodiment, the first micro-device and the second micro-device are positioned with a desired or pre-determined distance L apart, with a biological entity to be measured flowing from the first micro-device towards the second micro-device. When the biological entity passes the first micro-device, the first micro-device sends a signal to the passing biological entity, and then the second micro-device detects the response or retention of the perturbation signal on the biological entity. From the distance between the two micro-devices, time interval, the nature of perturbation by the first micro-device, and measured changes on the biological entity during the time of flight, microscopic and dynamic properties of the biological entity can be obtained. In another embodiment, a first micro-device is used to probe the biological entity by applying a signal (e.g., an electronic charge) and the response from the biological entity is detected by a second micro-device as a function of time. The voltage applied to the biological entity by the micro-device ranges from about 0.1 mV to about 10 V, or from about 1 mV to about 1.0 V.

Figure 7:
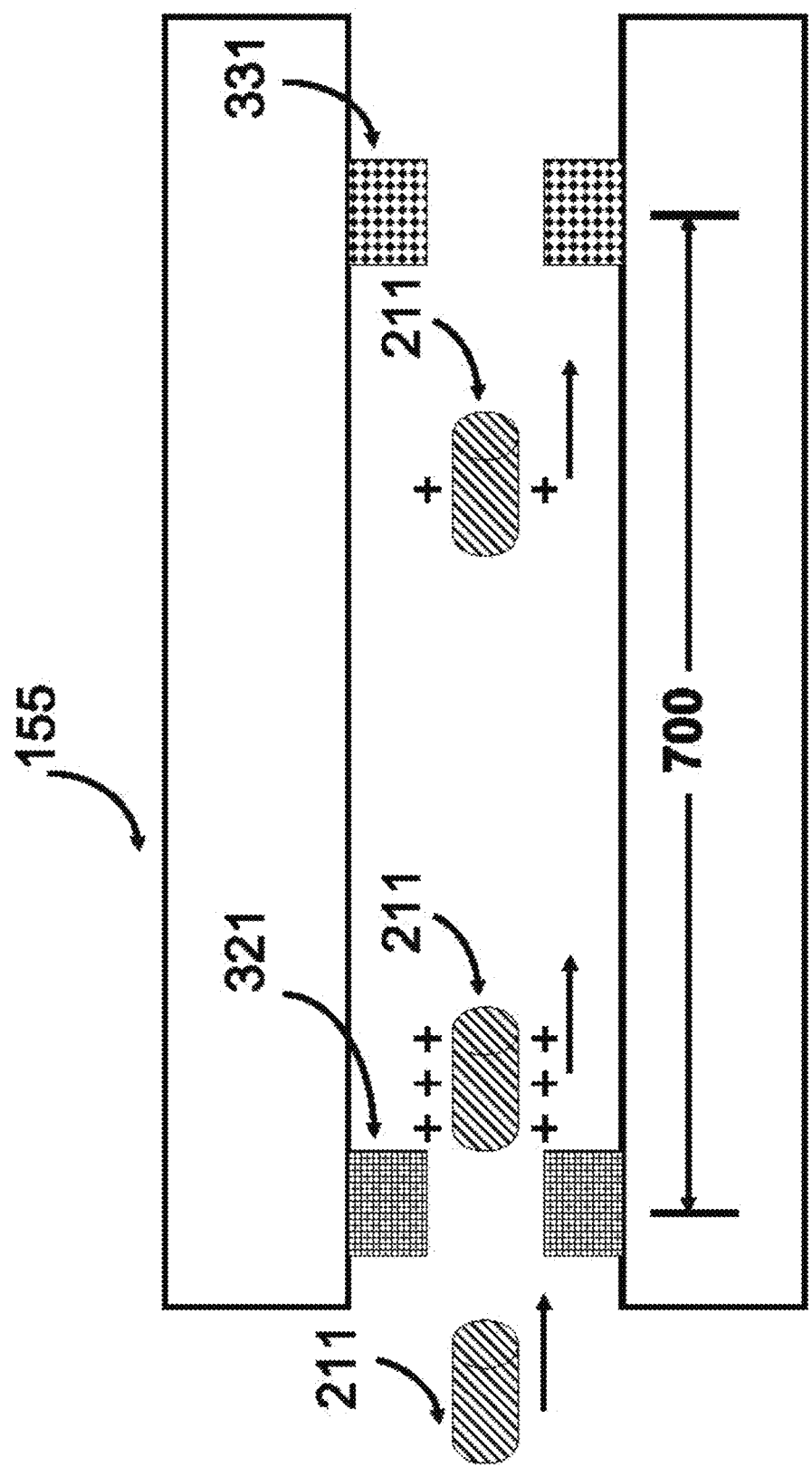
FIG. 7 is a perspective, cross-sectional illustration of a CTC detection apparatus of this invention with multiple micro-devices placed at a desired distance for time of flight measurements with enhanced sensitivity, specificity, and speed, including time dependent or dynamic information.

To further increase detection sensitivity, a novel detection process for disease detection is used, in which time of flight technique is employed. FIG. 7 is a perspective, cross-sectional illustration of detection apparatus 155 with multiple micro-devices 321 and 331 placed at a desired distance 700 for time of flight measurements to attain dynamic information on biological sample 211 (e.g., a cell) with enhanced measurement sensitivity, specificity, and speed. In this time of flight measurement, one or more properties of the biological sample 211 are first measured when the sample 211 passes the first micro-device 321. The same properties are then measured again when the sample 211 passes the second micro-device 331 after it has travelled the distance 700. The change in properties of sample 211 from at micro-device 321 to at micro-device 331 indicates how it reacts with its surrounding environment (e.g., a particular biological environment) during that period. It may also reveal information and provide insight on how its properties evolve with time. Alternatively, in the arrangement shown in FIG. 7, micro-device 321 could be used first as a probe to apply a probe signal (e.g., an electrical charge) to sample 211 as the sample passes the micro-device 321. Subsequently, the response of the sample to the probe signal can be detected by micro-device 331 as the sample passes it (e.g., change in the electrical charge on the sample during the flight). Measurements on biological sample 211 can be done via contact or non-contact measurements. In one embodiment, an array of micro-devices can be deployed at a desired spacing to measure properties of the biological entity over time.

The utilization of micro-devices (e.g., made by using the fabrication process flows of this invention) as discussed above and illustrated in FIG. 7 can be helpful for detecting a set of new, microscopic properties of a biological sample (e.g., a cell) that have not been considered in existing detection technologies. Such microscopic properties can be electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical properties of a biological sample that is a single biological entity (such as a cell). It is known that biological matters includes from basic bonding such as OH, CO, and CH bonding, to complex, three dimensional structures. Some of them have a unique signature in terms of its electronic configuration. Some of them may have unique electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical properties and configurations. Normal biological entity and diseased biological entity may carry different signatures with respective to the above said properties. However, none of the above stated parameters or properties have been routinely used as a CTC detection property. Using a CTC detection apparatus including one or more micro-devices of this invention, those properties can be detected, measured, and utilized as useful signals for CTC detection, particularly for early stage detection of cancer.

Figure 8:
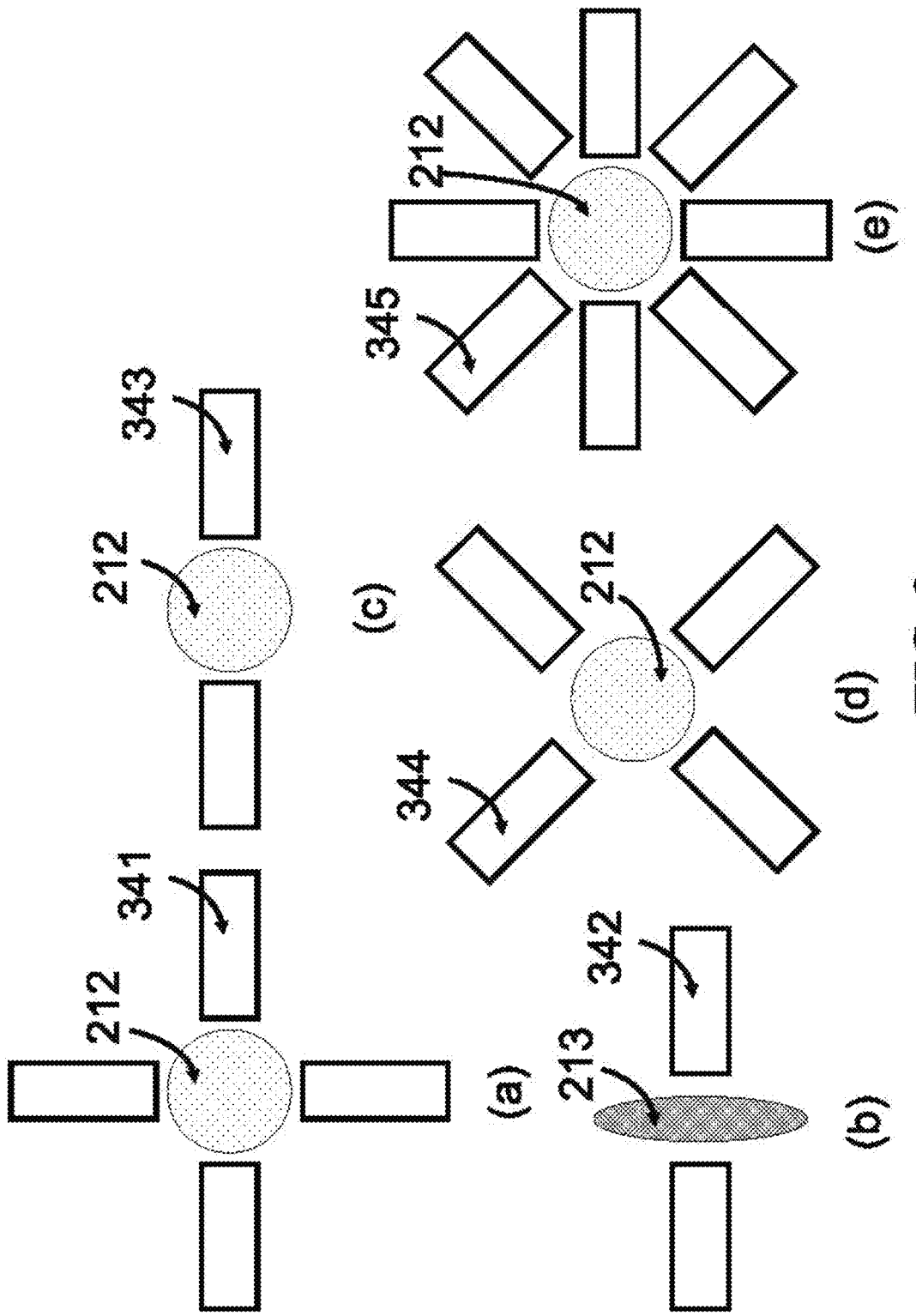
FIG. 8 is a perspective illustration of a novel set of microscopic probes, included in a CTC detection apparatus of this invention, for detecting various electronic or magnetic states, configurations, or other properties of a biological sample (e.g., a cell).

FIG. 8 is a perspective illustration of a novel set of microscopic probes 341, 342, 343, 344, 345, 346, and 347 designed and configured to detect various electronic, magnetic, or electromagnetic states, configurations, or other properties at microscopic level on biological samples 212, 213, 214, and 215, which is a single cell. As an example, in terms of measuring electronic properties, the shapes of biological samples 212, 213, 214, and 215 in FIG. 8 may represent electronic monopole (sample 212), dipole (samples 213 and 214), and quadruple (sample 215). The micro-devices 341, 342, 343, 344, 345, 346, and 347 are optimized to maximize measurement sensitivity of those said parameters including but not limited to electronic states, electronic charge, electronic cloud distribution, electrical field, and magnetic and electromagnetic properties, and the micro-devices can be designed and arranged in three dimensional configurations. For cancer disease, it is likely that electronic states and corresponding electronic properties differ between normal and cancerous cells. Therefore, by measuring electronic, magnetic and electromagnetic properties at microscopic levels including at cell level, CTC detection sensitivity and specificity can be improved.

In addition to the above examples in measuring electrical properties (e.g., charge, electronic states, electronic charge, electronic cloud distribution, electrical field, current, and electrical potential, and impedance), mechanical properties (e.g., hardness, density, shear strength, and fracture strength) and chemical properties (e.g., pH) in a single cell, and in FIG. 8 for measuring electrical, magnetic or electromagnetic states or configurations of biological samples at level, other micro-devices are disclosed in this application for sensitive electrical measurements.

Figure 9:
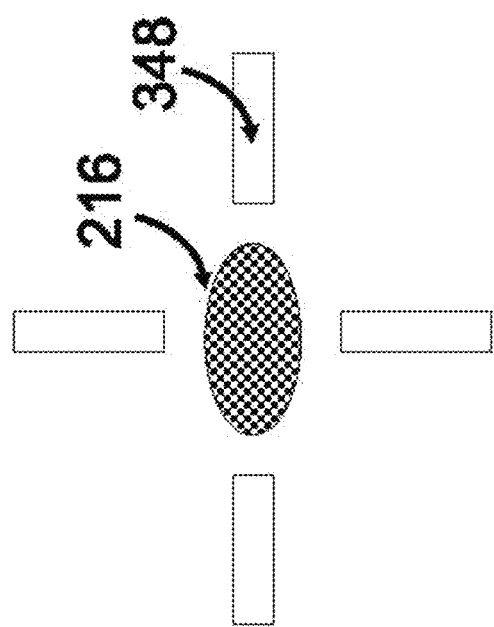
FIG. 9 is a perspective illustration of a novel four-point probe, included in a CTC detection apparatus of this invention, for detecting weak electronic signal in a biological sample (e.g., a cell).

FIG. 9 is a perspective illustration of a four-point probe for detecting weak electronic signal in a biological sample such as a cell, where a four point probe 348 is designed to measure electrical properties (impedance, capacitance, and weak electrical current) of a biological sample 216.

One of the key aspects of this invention is the design and fabrication process flows of micro-devices and methods of use the micro-devices for catching or measuring biological entities (e.g., cells) at microscopic levels and in three dimensional space, in which the micro-devices have microprobes arranged in three dimensional manner with feature sizes as small as a cell and capable of trapping, sorting, probing, measuring, detecting, counting, communicating, or modifying biological entities. Such micro-devices can be fabricated using state-of-the-art microelectronics processing techniques such as those used in fabricating integrated circuits. Using thin film deposition technologies such as molecular epitaxy beam (MEB) and atomic layer deposition (ALD), film thickness as thin as a few monolayers can be achieved (e.g., 4 A to 10 A). Further, using electron beam or x-ray lithography, device feature size on the order of nanometers can be obtained, making micro-device capable of trapping, probing, measuring, and modifying a biological entity (e.g., a single cell) possible.

Figure 10:
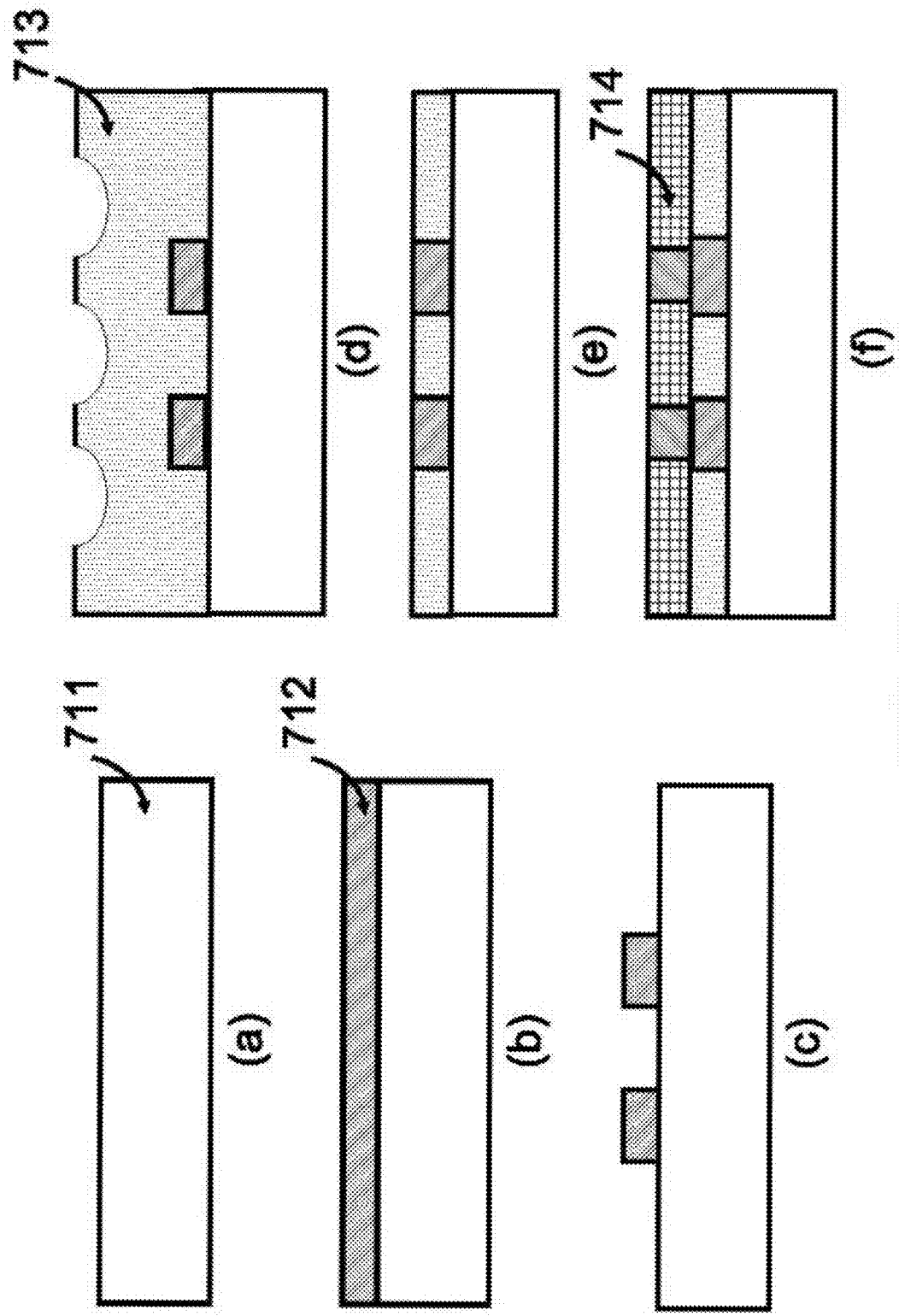
FIG. 10 illustrates a process flow for fabricating some apparatus of this invention.
Figure 10:
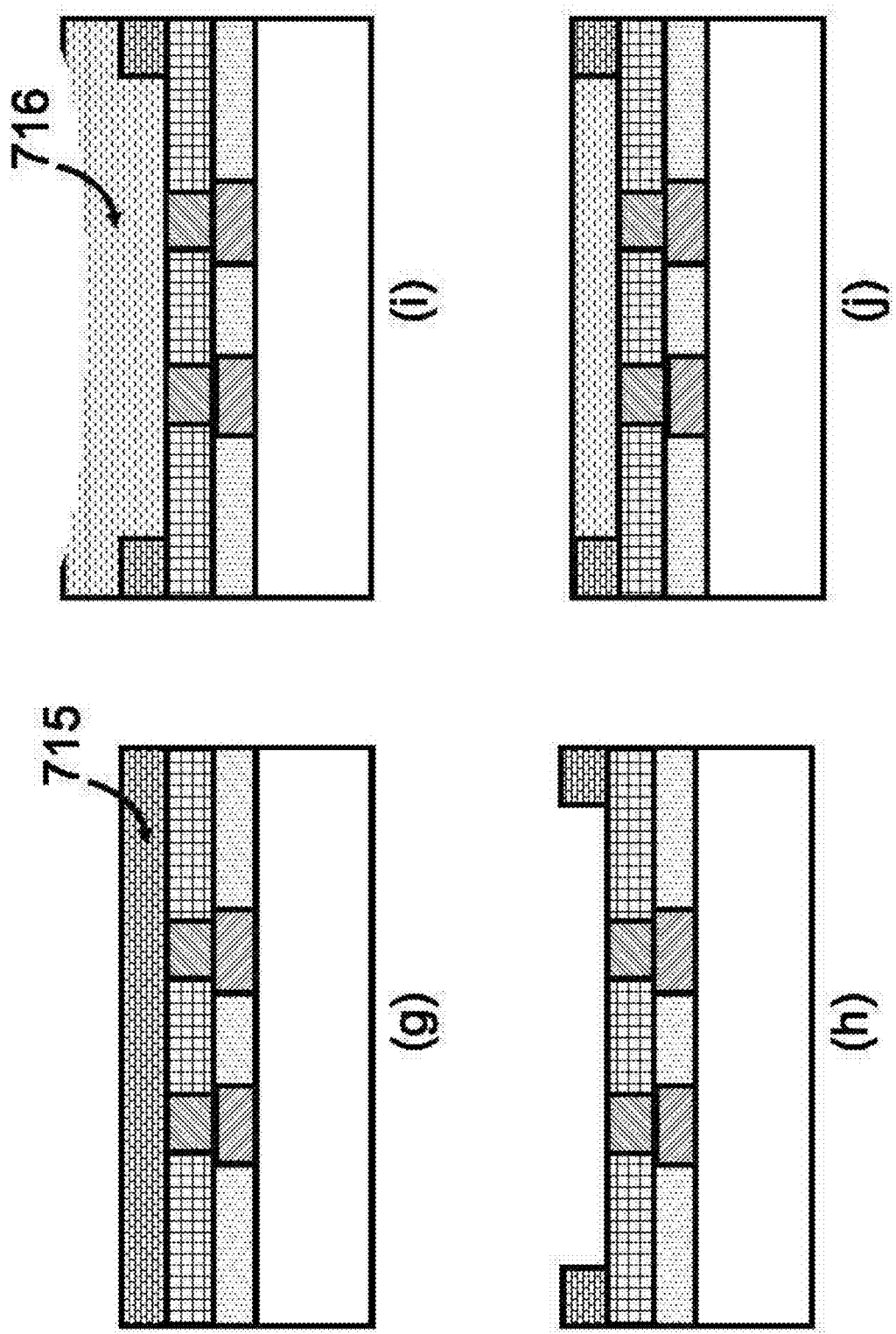
Figure 10:
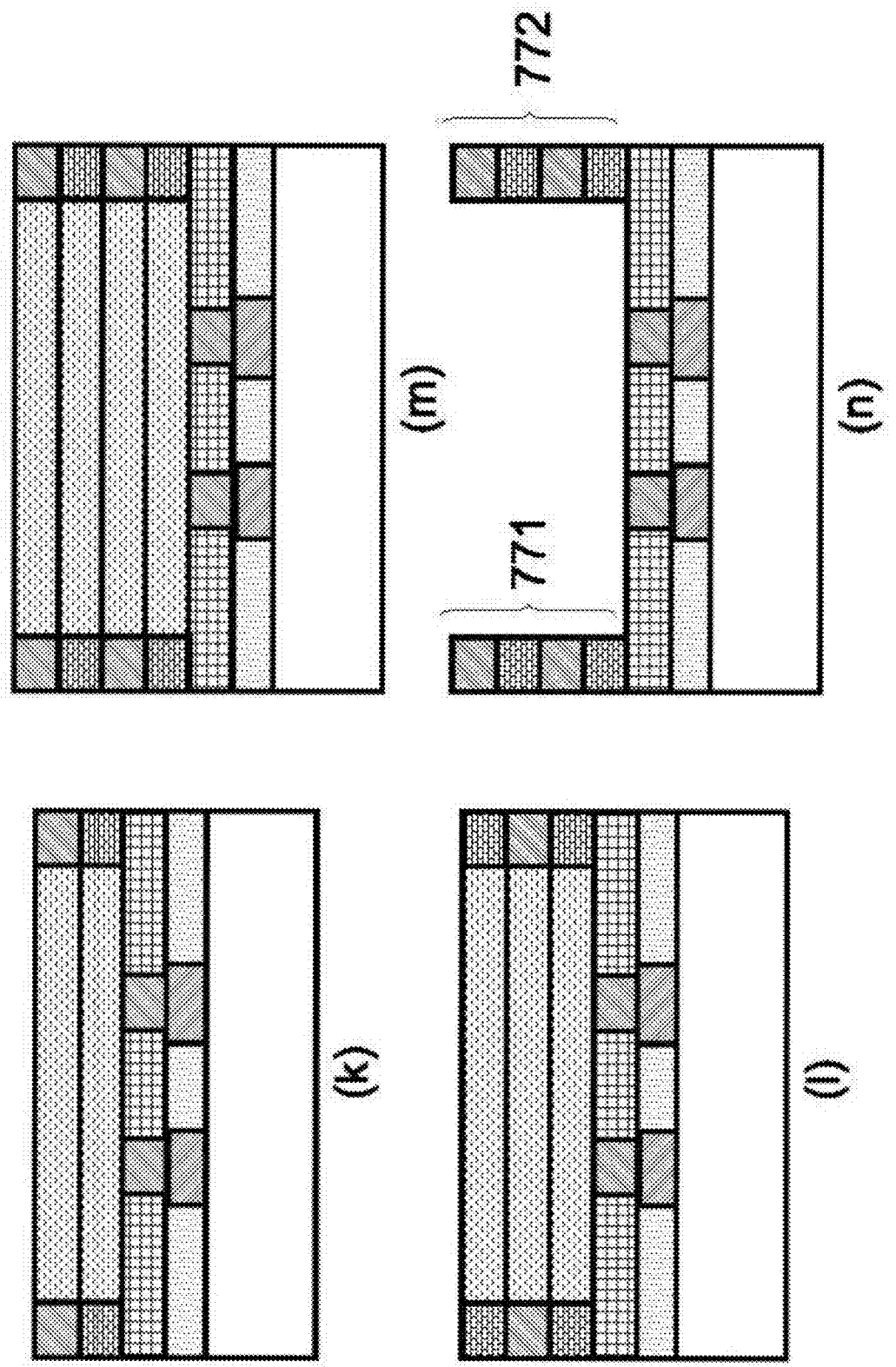
Figure 10:
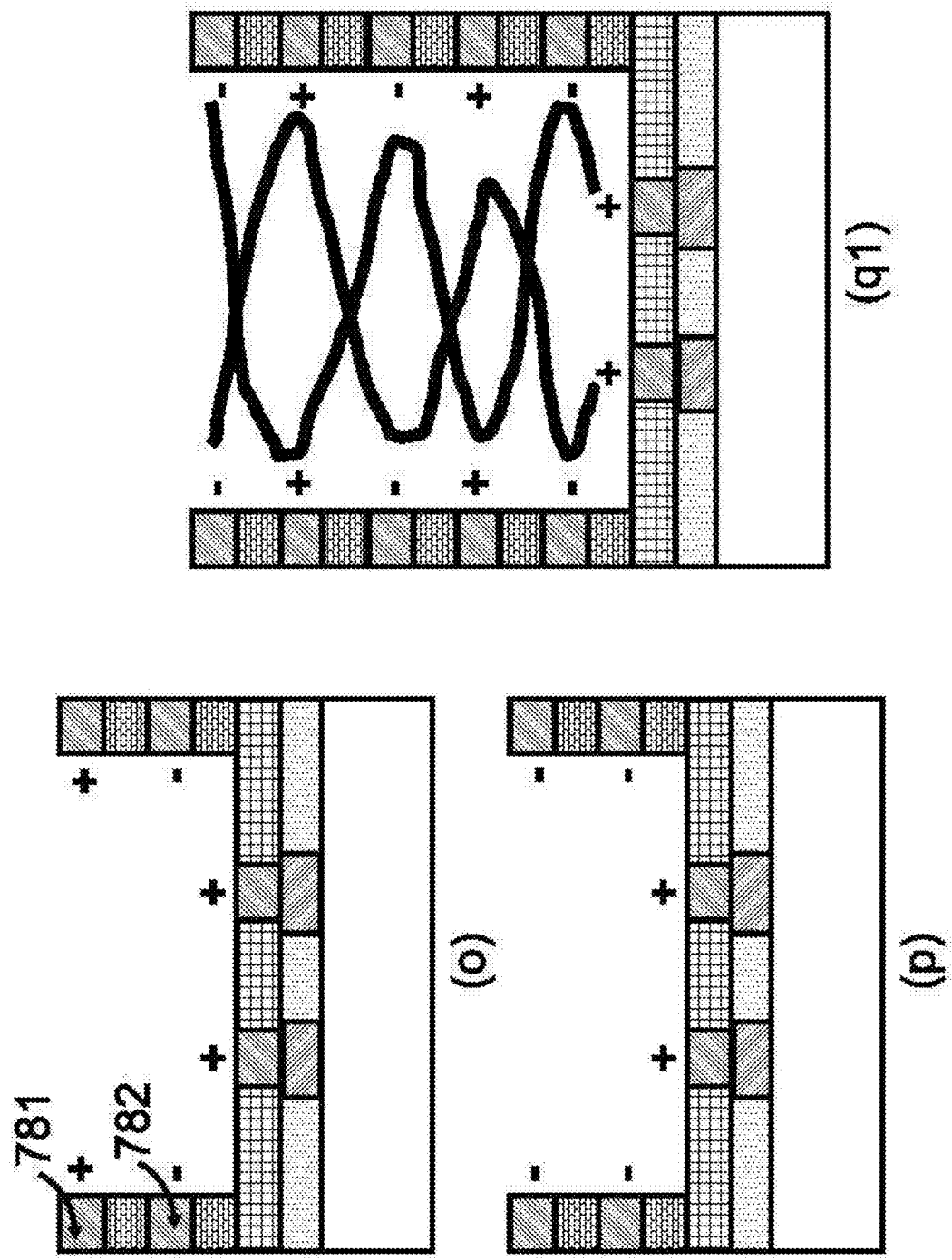
Figure 10:
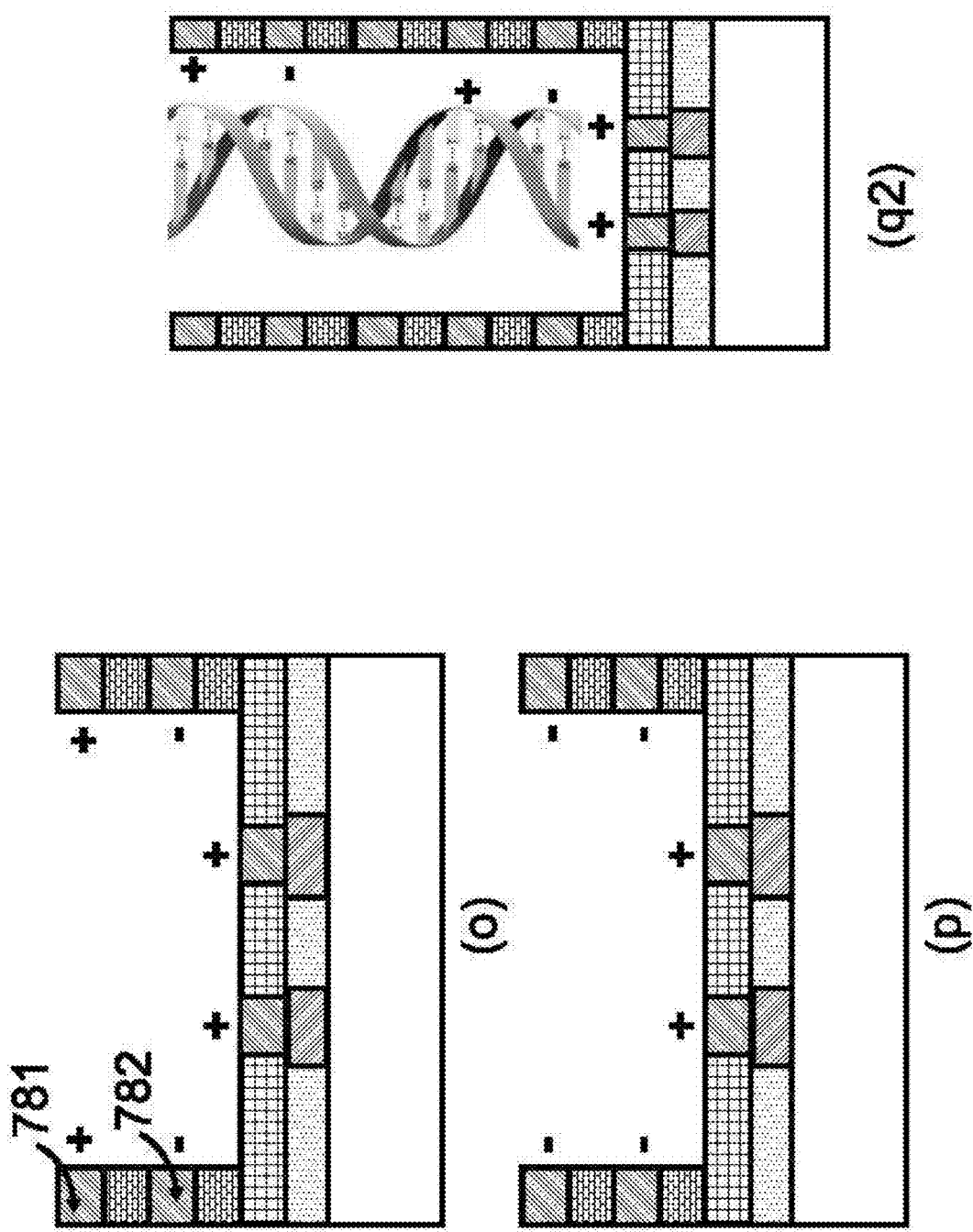
Figure 10:
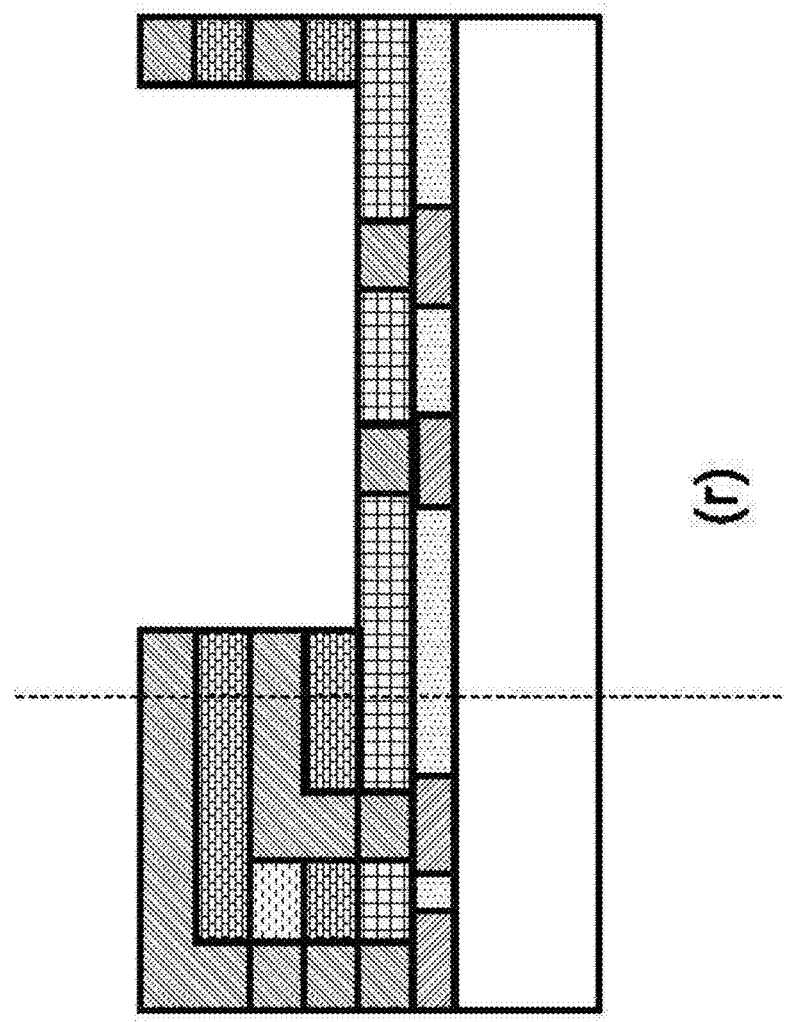

FIG. 10 illustrates a process flow for fabricating apparatus or micro-devices of this invention for trapping, sorting, probing, measuring, and modifying biological subjects (e.g., a single cell, a DNA or RNA molecule). In this process flow, microelectronics processes are utilized to fabricate micro-devices designed to achieve the above stated unique functions. Specifically, a first material 712 (typically a conducting material) is first deposited on a substrate 711 (FIG. 10(a) and FIG. 10(b)). The first material 712 is subsequently patterned by using lithography and etch processes (FIG. 10(c)). A second material 713 is then deposited and planarized using chemical mechanical polishing process to remove overburden of the second material 713 above the first material 712 (as shown in FIG. 10(e)). Another layer of material 714 is deposited and patterned, followed by deposition and planarization by chemical mechanical polishing of another layer of 712 (FIG. 10(f)). Next, a third material 715 is deposited and patterned, using lithography and etch processes (FIG. 10(g) and FIG. 10(h)), followed by deposition and planarization of a fourth material 716, typically a sacrificial material (FIG. 10(i) and FIG. 10(j)). Repeating the process flow of deposition of patterning material 712 or material 715 alternatively, and deposition of material 716 and planarization by chemical mechanical polishing (FIGS. 10(k)-(m)), a film stack featuring multiple layers with alternating material 712 (e.g., a conducting material) and material 715 (e.g., an insulating material) in at least portions of the device is formed. Finally, material 716 between film stacks 771 and 772 is removed by wet etch, dry etch (which may require lithography process), or vapor etch, selective to all other materials (FIG. 10(n)). As illustrated in FIG. 10(o), in the case of 712 being a conductive material connected to an electrical circuit or an electrical source (e.g., a charge source), each probe tip formed by 712 on the stack (e.g., 781 and 782) can have a charge or an electrical field at the surface (e.g., 781 and 782), which (each probe tip) can be selected to have a positive charge or a negative charge, or a positive electrical field or negative electrical field. Conversely, such probe tip can also sense various properties of biological subject being measured (e.g., electronic cloud, field, charge, or temperature when the probe tip is a thermal detector, or light emission when the probe tip is an optical sensor). Using electrical circuit or electrical source, various combinations of electrical charge distribution or electrical field can be placed on the micro-device, as shown in FIG. 10(o) and FIG. 10(p), which can be used to sort and trap various biological subjects such as a cell and a DNA molecule. For instance, a biological subject with a charge distribution inverse of that in FIG. 10(p) can be trapped by the micro-device shown in FIG. 10(p). An array of micro-devices with various charge distributions or electrical field distributions can trap their respective biological subjects in a high speed, which can serve as a sorting device. FIGS. 10(q1) and 10(q2) illustrate the use of a micro-device capable of trapping a DNA or measuring various properties (e.g., electrical, thermal, or optical properties) of a DNA, with each probe tip matched up spatially with either a major groove or minor groove of a double helix DNA. FIG. 10(r) illustrates how the probe tips are connected to electrical circuit, where only electrical wiring is shown. It should be noted that the micro-device shown in this example can be integrated onto a single chip with one billion or more such micro-devices to trap and/or sort cells, DNAs, RNAs, proteins, and other biological subject in a high speed.

Another aspect of this invention relates to micro-indentation probes and micro-probes for measuring a range of physical properties (such as mechanical properties) of biological entities. Examples of the mechanical properties include hardness, shear strength, elongation strength, fracture stress, and other properties related to cell membrane which is believed to be a critical component in disease diagnosis.

Figure 11:
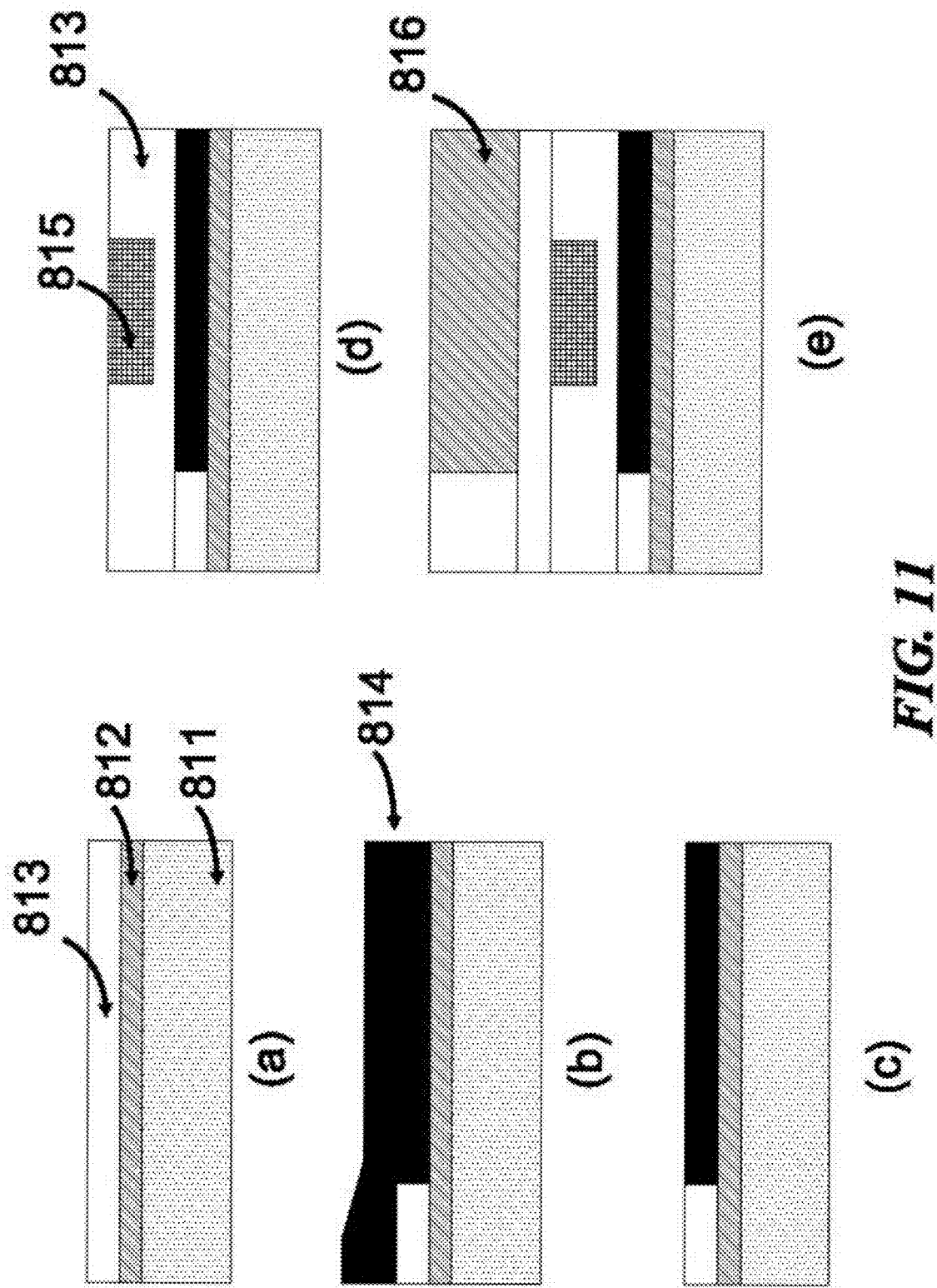
FIG. 11 illustrates a novel process flow for fabricating a class of micro-devices capable of measuring physical properties of a biological entity (e.g., a cell) such as mechanical properties (e.g., hardness, shear strength, elongation strength, fracture stress) and other properties related to cell membrane.
Figure 11:
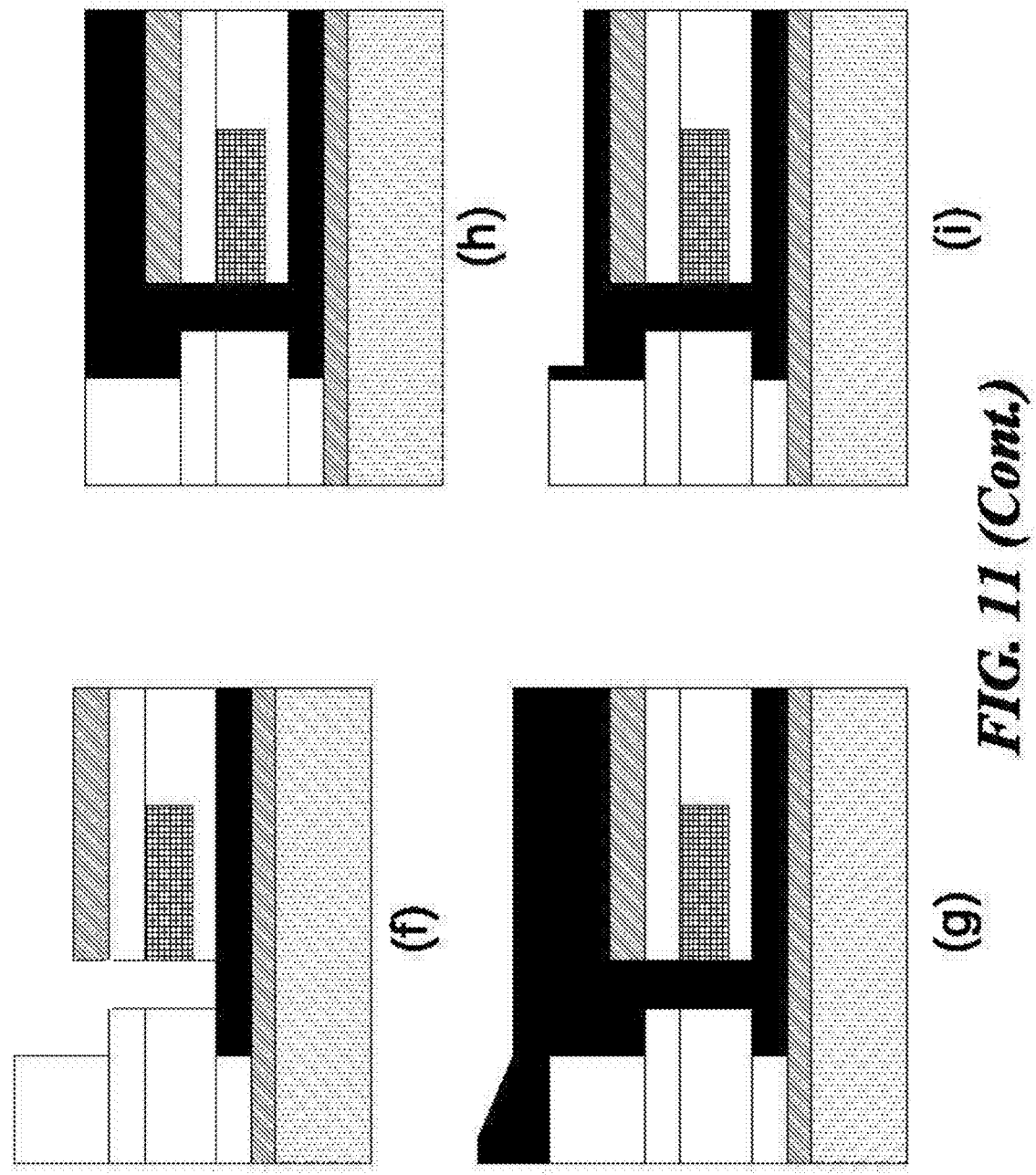
Figure 11:
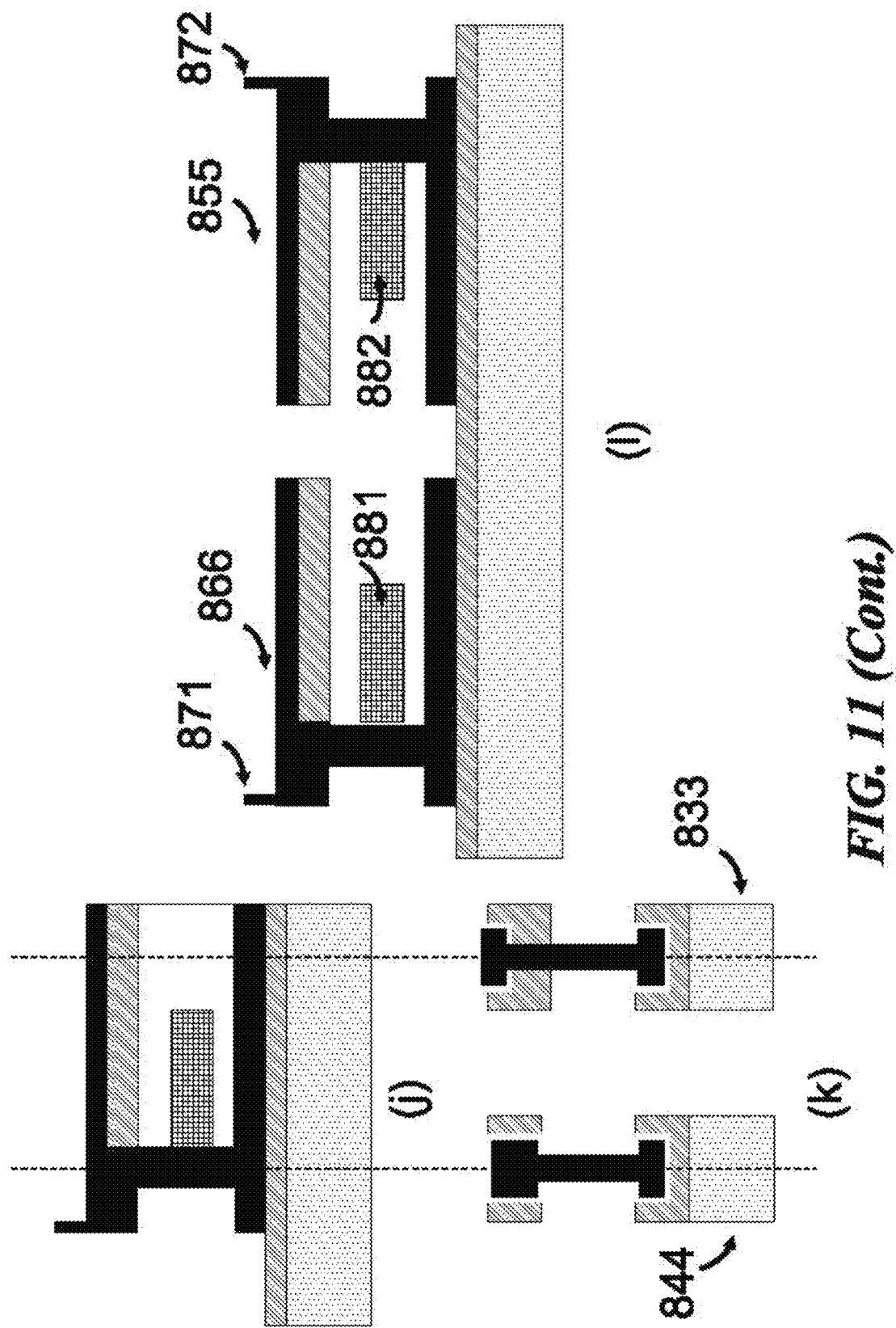

FIG. 11 illustrates a novel fabrication process flow for micro-devices capable of probing a range of properties of biological entities, such as mechanical properties of cell membrane (e.g., mechanical strength of a cell membrane). In this process flow, a material 812 is first deposited onto a substrate 811, followed by the deposition of another material 813 (FIG. 11(a)). Following patterning of material 813 using lithography and etch processes, a material 814 is deposited (FIG. 11(b)) and planarized (FIG. 11(c)). Another layer of material 813 is next deposited and patterned using lithography and etch processes to remove portions of the material 813, followed by the deposition and planarization of a material 815 (which can be a piezoelectric material and can serve as a driver) (FIG. 11(d)). A layer of material 813 is next deposited, followed by deposition and patterning of yet another layer of 813, and deposition and planarization of material 816 (FIG. 11(e)). Next, material 816 is etched back to a reduced thickness, and patterned, followed by patterning of triple-layer of material 813 (FIG. 11(f)). Another layer of 814 is deposited (FIG. 11(g)) and planarized by chemical mechanical polishing (FIG. 11(h)), and patterned (FIG. 11(i)). Finally, multiple layers of 813 are removed by wet etch or vapor etch (FIG. 11(j)). FIG. 11(k) is a perspective, cross-sectional illustration of the micro-device in a plane perpendicular to that in FIG. 11(j) (90-degree rotation from FIG. 11(*j*)). FIG. 11(*l*) illustrates a micro-device with two micro-tips 871 and 872 which can move in opposite directions when a voltage is applied to piezoelectric drivers 881 and 882, which can be used to probe biological entities such as cells.

Figure 12:
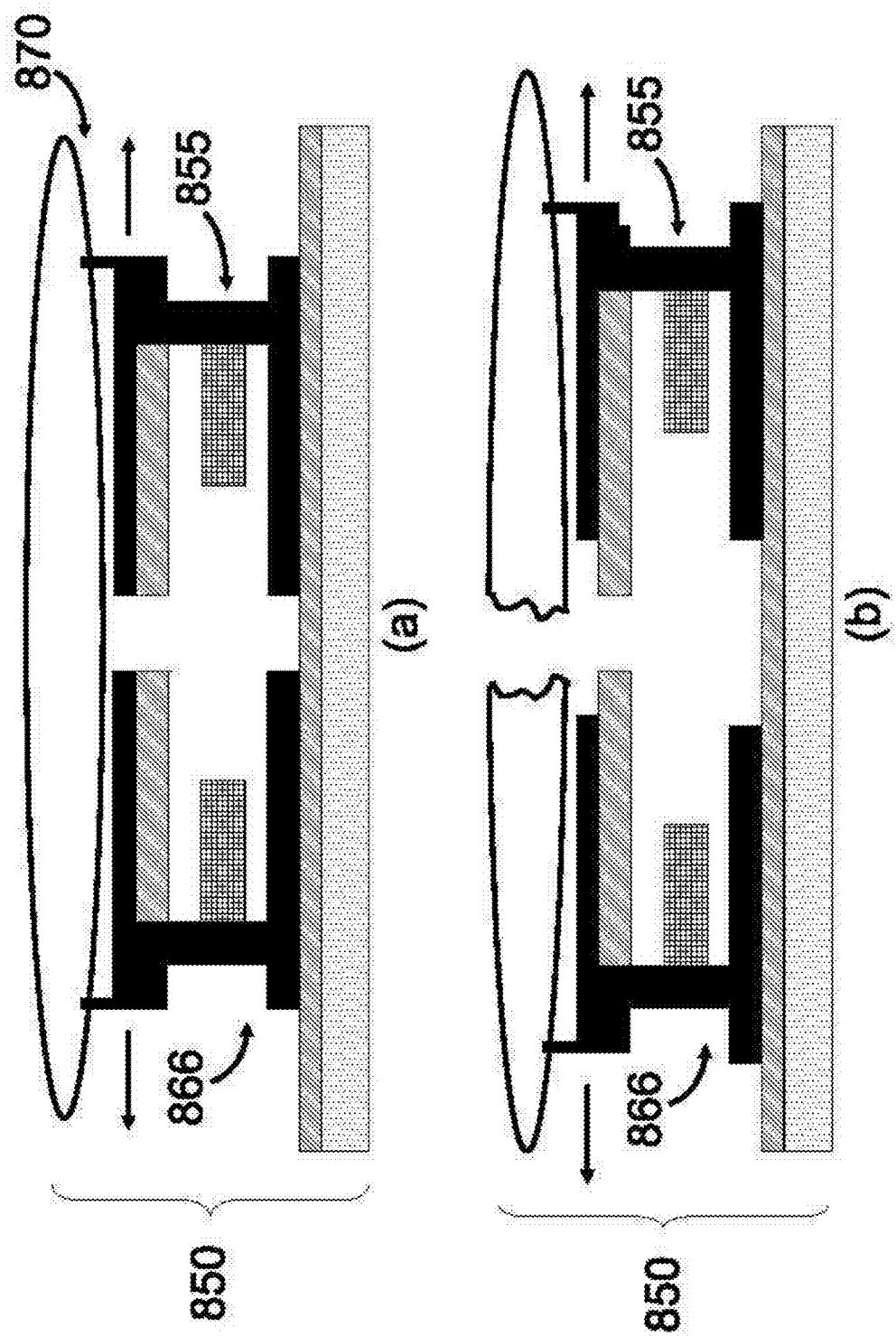
FIG. 12 illustrates how a micro-device with two microprobes capable of moving in opposite directions when a force is applied can be utilized to probe properties of a biological entity (e.g., mechanical properties of a cell membrane).

FIG. 12 is an illustration of how micro-devices fabricated using the novel manufacturing process shown in FIG. 11 work. In FIG. 12, a micro-device 850 with two micro-probes 866 and 855 can move in opposite directions upon a force being applied (FIG. 12(*a*)). When the tips of the two probes are penetrated into a cell 870, as the distance between the two micro-probes is increased with the increasing applied force, the cell is stretched. Finally, as the applied force is reached a critical value, the cell is broken into two pieces (FIG. 12(*b*)). The dynamic response of the cell to the applied force provides information on the cell, particularly on the mechanical properties (e.g., elasticity) of cell membrane. The force at the point in which the cell is torn apart reflects the strength of the cell and it may be called a breaking point: the greater the mechanical strength of the cell membrane is, the greater the force is at the breaking point.

Another novel approach provided by this invention is the use of phase lock-in measurement for CTC detection, which reduces background noise and effectively enhances signal to noise ratio. Generally, in this measurement approach, a periodic signal is used to probe the biological sample and response coherent to the frequency of this periodic probe signal is detected and amplified, while other signals not coherent to the frequency of the probe signal is filtered out, which thereby effectively reduces background noise. In one of the embodiments in this invention, a probing micro-device can send a periodic probe signal (e.g., a pulsed laser team, a pulsed thermal wave, or an alternating electrical field) to a biological entity, response to the probe signal by the biological entity can be detected by a detecting micro-device. The phase lock-in technique can be used to filter out unwanted noise and enhance the response signal which is synchronized to the frequency of the probe signal. The following two examples illustrate the novel features of time of flight detection arrangement in combination with phase lock-in detection technique to enhance weak signal and therefore detection sensitivity in CTC detection measurements.

FIG. 13 is an illustration of a novel time of flight detection arrangement for CTC detection applications. Specifically, FIG. 13(*a*) shows a set-up for measuring biological entity 911 using detection probe 933 and clock generator 922, and FIG. 13(*b*) contains recorded signal 921 due to structure 922, signal 931 recorded by signal probe 933, and processed signal 941 using a phase lock-in technique to filter out noise in recorded signal 931, where only response synchronized to clock signal 921 is retained. In the setup shown in FIG. 13(*a*), when a biological entity such as a cell 911 passes a structure 922, it triggers a clear signal (e.g., a light scattering signal if 922 is a light source, or a sharp increase in voltage if 922 is an orifice structure in a resistor). Therefore, 922 can be used to register the arrival of the biological subject, and as a clock when multiple structures of 922 are placed at a periodic distance as shown in recorded signal trace 921 in FIG. 13(*b*). In addition, when 922 is placed at a known distance in front of a probe 933, it marks the arrival of a biological entity coming towards 933 and signal response recorded at 933 is delayed by a time t from the signal triggered by 922 where t equals distance between 922 and 933 divided by traveling speed of the biological entity. As illustrated in FIG. 13(*b*), signal 921 due to structure 922 is clear and periodic with periodicity proportional to distance between structure 922s, while signal measured by probe 933 has a high noise level and relatively weak signal related to the biological entity. With the utilization of phase lock-in technique to filter out noise in recorded signal 931 by the detection probe 933 un-synchronized to clock signal 921, signal to noise ratio can be greatly enhanced as shown in processed signal 941 in FIG. 13(*b*).

FIG. 14 illustrates yet another time of flight CTC detection arrangement in which a clock signal generator 922, a probe signal generator 944, and a signal detection probe 955 are used, along with schematically recorded clock signal 921, total recorded response signal 951 (except clock signal), and processed signal 952 using phase lock-in technique. In this arrangement, a probe signal generator 944 is used to perturb the biological entity 911 (e.g., heating 911 up using an optical beam, or adding an electrical charge to 911), and response to the probe signal is subsequently measured as a function of time using an array of detection probes 955. The filtered signal in 952 shows dynamic response to probe signal by 944 as it decays over time. Since normal cell and abnormal cell may respond differently to the probe signal, this arrangement with proper micro-probes can be utilized to detect cancer. In another embodiment utilizing this set-up (shown in FIG. 14), the probe signal generator 944 can send a periodic signal to the biological entity 911, detected response signal from the biological entity by the detection probe 955 can be processed using the phase lock-in technique, with noise un-synchronized to the frequency of the probe signal filtered out and signal synchronized to the probe signal frequency amplified.

FIG. 15 is a perspective illustration of the novel multi-property micro-filter. A timed shutter 1502 is sandwiched between 2 pieces of filter membrane 1501 with wells. When a biological subject 1511 moves through the pathway of the well, it is first detected by the counter 1512, which triggers the clock of the barrier panel 1502. Then the larger cells will be filtered out, or blocked, by the filter's holes (not in the figure), while only the specific subjects with enough speed are able to get through the pathway 1503 before the timed shutter 1502 closes the filter pathway (see FIG. 15(*b*)). Otherwise it will be held back as the timed shutter 1502 moves to block the pathway as shown in FIG. 15(*c*).

FIG. 16 illustrates a fluid delivery system that includes a pressure generator, a pressure regulator, a throttle valve, a pressure gauge, and distributing kits. The pressure generator 1605 sustains fluid with desired pressure, and the pressure is further regulated by the regulator 1601 and then accurately manipulated by the throttle valve 1602. Meanwhile, the pressure is monitored at real time and fed back to the throttle valve 1602 by the pressure gauge 1603. The regulated fluid is then in parallel conducted into the multiple devices where a constant pressure is needed to drive the fluid sample.

FIG. 17 illustrates how a micro-device in a CTC detection apparatus of this invention can communicate, probe, detect, and optionally treat and modify biological entities at a microscopic level. FIG. 17(*a*) illustrates the sequence of cellular events from signal recognition to cell fates determination. First, as the signals 1701 are detected by receptors 1702 on the cell surface, the cell will integrate and encode the signals into a biologically comprehensible message, such as calcium oscillation 1703. Consequently, corresponding proteins 1704 in the cell will interact with the message, then be modified and transform into ion-interacted proteins 1705 accordingly. Through the translocation, these modified proteins 1705 will pass the carried message to the nuclear proteins, and the controlled modification on nuclear proteins will modulate the expression of gene 1707 which includes transcription, translation, epigenetic processes, and chromatin modifications. Through messenger RNA 1709, the message is in turn passed to specific proteins 1710, thereby changing their Concentration—which then determines or regulates a cell's decision or activities, such as differentiation, division, or even death.

FIG. 17(*b*) illustrates an apparatus of this invention which is capable of detecting, communicating with, treating, modifying, or probing a single cell, by a contact or non-contact means. The apparatus is equipped with micro-probes and micro-injectors which are addressed and modulated by the controlling circuitry 1720. Each individual micro-injector is supplied with a separate micro-cartridge, which carries designed chemicals or compounds.

To illustrate how an apparatus of this invention can be used to simulate an intracellular signal, calcium oscillation is taken as an example mechanism. First, a $Ca^{2+}$-release-activated channel (CRAC) has to be opened to its maximal extent, which could be achieved by various approaches. In an example of the applicable approaches, a biochemical material (e.g., thapsigargin) stored in the cartridge 1724 is released by an injector 1725 to the cell, and the CRAC will open at the stimulus of the biological entity. In another example of the applicable approaches, the injector 1724 forces a specific voltage on cell membrane, which causes the CRAC to open as well.

The $Ca^{2+}$ concentration of a solution in the injector 1728 can be regulated as it is a desirable combination of a $Ca^{2+}$-containing solution 1726, and a $Ca^{2+}$ free solution 1727. While the injector 1730 contains a $Ca^{2+}$ free solution, then injectors 1728 and 1730 are alternately switched on and off at a desired frequency. As such, the $Ca^{2+}$ oscillation is achieved and the content inside the cell membrane are then exposed to a $Ca^{2+}$ oscillation. Consequently, the cell's activities or fate is being manipulated by the regulated signal generated by the apparatus.

Meanwhile, the cell's response (e.g., in the form of an electric, magnetic, electromagnetic, thermal, optical, acoustical, or mechanical property) can be monitored and recorded by the probes integrated in this apparatus.

FIG. 17(*c*) illustrates another design of apparatus which is able to setup communication with a single cell. The apparatus is equipped with micro-probes which are coated with biologically compatible compounds or elements, e.g., Ca, C, Cl, Co, Cu, H, I, Fe, Mg, Mn, N, O, P, F, K, Na, S, or Zn. These probes can generate oscillating chemical signals with such an element or compound to interact with the cell, and results into a response that affects the cell's activities or eventual fate as described above. Likewise, this apparatus can probe and record the cell's response (e.g., in the form of an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical property) as well.

FIG. 18 illustrates the system block diagram of a CTC detection apparatus of this invention. This example includes a fluid delivering system 1801, biological interface 1802, a probing and detecting device 1803, a system controller 1805, a medical waste reclaiming and treating system 1804. A biological sample or material is transported to the interface 1802 by the fluid delivery system 1801, meanwhile the fluid parameters (or properties) are reported to the system controller 1805 which comprises a logic processing unit, a memory unit, an application specific chip, a sensor, a signal transmitter, and a signal receiver; and then the system controller 1805 can give further command to the system. The interface 1802 is an assembly which bridges a fluid sample and the detecting device, and further monitors the parameters or properties of the biological sample (e.g., pressure, temperature, stickiness, or flow rate) and then reports the date to the system controller 1805 while distributing the biological sample to the probing and detecting device 1803 with a specified speed or pressure (which can be commanded by the system controller 1805).

The system controller 1805 is the central commander and monitor of the entire system (or apparatus), where all the parameters and information from various modules is processed and exchanged and the instructions are given out, and where the command is dispatched. The system controller 1805 can include, e.g., a pre-amplifier, an electrical meter, a thermal meter, a switching matrix, a system bus, a nonvolatile storage device, a random access memory, a processor, and a user interface through which the user of the apparatus can manipulate, configure the apparatus, and read the operating parameters and final result. The pre-amplifier can process the raw signal to a recognizable signal for the meters. The meters can force and measure corresponding signals which can be, e.g., electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical signals, or combinations thereof. The switching matrix can switch the testing terminals of different arrays of the probe sub-apparatus. The user interface includes input and output assemblies and is an assembly which seals the fluid delivery system and the probing and detecting device together.

The probing and detecting device 1803 is the core functional module of the CTC detection apparatus of this invention as it is the unit that probes the biological sample and collects related cellular signals (or responses). The waste reclaiming and treating system 1804 reclaims the waste biological sample to protect the privacy of its biological host, and keeps it away from polluting the environment.

FIGS. 19(*b*)-(*n*) illustrate a process flow for fabricating a micro-device for trapping, sorting, probing, measuring, treating, or modifying a biological subject (e.g., a single cell, a DNA or RNA molecule). A first material 1902 (e.g., a piezoelectric conducting material) and a second material 1903 (e.g., a conducting material) are sequentially deposited on a substrate 1901 (see FIGS. 19(*b*) and 19(*c*)). The second material 1903 is subsequently patterned by lithography and etch processes (see FIG. 19(*d*)). A third material 1904 is next deposited (as shown in FIG. 19(*e*)) and planarized (see FIG. 19(*f*)). A layer of a fourth material 1905 is subsequently deposited (see FIG. 19(*g*)) and patterned as a hard mask (see FIG. 19(*h*)), followed by etch to remove the third and first materials from desired areas, which stops on the substrate 1901. FIG. 19(*i*) is a perspective illustration of the device, while FIG. 19(*j*) is a vertical illustration of the same device.

FIG. 19 (*k*) illustrates the use of a micro-device capable of trapping a DNA 1920 and measuring various properties (e.g., electrical, magnetic, physical, thermal, chemical, biological, bio-chemical, or optical properties) of a DNA. Each probe tip 1912 matches up spatially with either a major groove or minor groove of a double helix DNA. Meanwhile, two probes (1911 and 1910) configured at the end of the trench can force or measure signals to each strand end of the DNA's double helix. The probes can be made of a conducting material with optionally a piezoelectric support structure, which can stretch forward and backward at a desired distance. All the probes are numbered, addressed, and controlled by a controlling circuitry.

FIG. 19(*l*) shows a simplified form of the device illustrated in FIG. 19(*k*). In this device, probe tips match spatially with interlaced grooves of a double helix DNA. The number of groove intervals between the adjacent probes is variable. If required, either DNA can be moved (for example, by pulling by probes 1910 and 1911) or the probes can move along the trench direction, mapping out properties in a full or partial DNA.

FIG. 20 illustrates an apparatus of this invention that is capable of detecting or measuring the surface charge of a biological subject 2010. It includes a channel, a pair of plates 2022, and a slit 2030 which separates the channel into a top channel 2041 and a bottom channel 2051. When a biological subject 2010 carrying a surface charge (positive charge shown in FIG. 20(*a*)) passes through the channel, under the influence of the voltage applied on the plates 2022 (with positive voltage at the top plate and negative at the bottom plate), it will move towards the bottom plate as shown in FIG. 20(*b*). Thus, the biological subject 2010 will pass through the bottom channel 2051 when it reaches slit 2030. (If the biological subject 2010 carries a negative charge, it would pass through the top channel 2041.) This way, a biological subject with unknown charge type (negative or positive) can be determined by using this apparatus.

This device comprises at least 2 parts of channel, one of which is channel 2060 where the biological subject is charged or modified, and the other comprises at least one plate or slit to separate the biological subjects (e.g., where the biological subjects are separated).

As surface charge will affect the shape of a biological subject, by using novel and multiple plates, information on the shape and charge distribution of biological subjects can be obtained. The general principle and design of the micro-device can be extended to a broader scope, thereby making it possible to obtain other information on the biological subject via separation by applying other parameters such as ion gradient, thermal gradient, optical beam, or another form of energy.

FIG. 21 illustrates another apparatus of this invention for detecting or measuring microscopic properties of a biological subject 2110 by utilizing a micro-device that includes a channel, a set of probes 2120, and a set of optical sensors 2132 (see, FIG. 21(*a*)). The detected signals by probes 2120 can be correlated to information including images collected by the optical sensors 2132 to enhance detection sensitivity and specificity. The optical sensors can be, e.g., a CCD camera, a florescence light detector, a CMOS imaging sensor, or any combination.

Alternatively, a probe 2120 can be designed to trigger optical emission such as florescence light emission 2143 in the targeted biological subject such as tumor cells, which can then be detected by an optical probe 2132 as illustrated in FIG. 21(*c*). Specifically, biological subjects can be first treated with a tag solution which can selectively react to a tumor cell. Subsequently, upon reacting (contact or non-contact) with probe 2120, optical emissions from the tumor cell occur and can be detected by optical sensors 2132. This novel process using the micro-devices of this invention is more sensitive than such conventional methods as traditional florescence spectroscopy as the emission trigger point is directly next to the optical probe and the triggered signal 2143 can be recorded in real time and on-site, with minimum loss of signal.

FIG. 22 illustrates another embodiment of the apparatus of this invention, which can be used to separate biological subjects of different geometric size and detect their properties respectively. It includes at least an entrance channel 2210, a disturbing fluid channel 2220, an accelerating chamber 2230, and two selecting channels 2240 and 2250. The angle between 2220 and 2210 is between 0° and 180°. The biological subject 2201 flows in the x-direction from 2210 to 2230. The biocompatible distribution fluid 2202 flows from 2220 to 2230. Then the fluid 2202 will accelerate 2201 in y-direction. However, the acceleration correlates with the radius of the biological subjects and the larger ones are less accelerated than the small ones. Thus, the larger and smaller subjects are separated into different channels. Meanwhile, probes can be optionally assembled aside the sidewall of 2210, 2220, 2230, 2240, and 2250. They could detect electric, magnetic, electromagnetic, thermal, optical, acoustical, biological, chemical, physical, or mechanical properties at the microscopic level.

The channel included in the apparatus of this invention can have a width of, e.g., from 1 nm to 1 mm. The apparatus should have at least one inlet channel and at least two outlet channels.

FIG. 23 shows another apparatus of this invention with an acoustic detector 2320 for measuring the acoustic property of a biological subject 2301. This apparatus includes a channel 2310, and at least an ultrasonic emitter and an ultrasonic receiver installed along the sidewall of the channel. When the biological subject 2301 passes through the channel 2310, the ultrasonic signal emitted from 2320 will be received after carrying information on 2301 by the receiver 2330. The frequency of the ultrasonic signal can be, e.g., from 2 MHz to 10 GHz, and the trench width of the channel can be, e.g., from 1 nm to 1 mm. The acoustic transducer (i.e., the ultrasonic emitter) can be fabricated using a piezoelectric material (e.g., quartz, berlinite, gallium, orthophosphate, $GaPO_4$, tourmalines, ceramics, barium, titanate, $BatiO_3$, lead zirconate, titanate PZT, zinc oxide, aluminum nitride, and polyvinylidene fluorides).

FIG. 24 shows another apparatus of this invention that includes a pressure detector for biological subject 2401. It includes at least one channel 2410 and whereon at least one piezoelectric detector 2420. When the biologic subject 2401 passes through the channel, the piezoelectric detector 2420 will detect the pressure of 2401, transform the information into an electrical signal, and send it out to a signal reader. Likewise, the trench width in the apparatus can be, e.g., from 1 nm to 1 mm, and the piezoelectric material can be, e.g., quartz, berlinite, gallium, orthophosphate, $GaPO_4$, tourmalines, ceramics, barium, titanate, $BatiO_3$, lead zirconate, titanate PZT, zinc oxide, aluminum nitride, or polyvinylidene fluorides.

FIG. 25 shows another apparatus of this invention that include a concave groove 2530 between a probe couple, in the bottom or ceiling of the channel. When a biological subject 2510 passes through, the concave 2530 can selectively trap the biological subject with particular geometric characteristics and makes the probing more efficiently. The shape of concave's projection can be rectangle, polygon, ellipse, or circle. The probe could detect electric, magnetic, electromagnetic, thermal, optical, acoustical, biological, chemical, physical, or mechanical properties. Similarly, the trench width can be, e.g., from 1 nm to 1 mm. FIG. 25(*a*) is an up-down view of this apparatus, FIG. 25(*b*) is a side view, whereas FIG. 25(*c*) is a perspective view.

FIG. 26 is another apparatus of this invention that also includes concave grooves 2630 (of a different shape from those shown in FIG. 25) on the bottom or ceiling of the channel. When a biological subject 2610 passes through, the concave grooves 2630 will generate a turbulent fluidic flow, which can selectively trap the micro-biological objects with particular geometric characteristics. The probe could detect electric, magnetic, electromagnetic, thermal, optical, acoustical, biological, chemical, physical, or mechanical properties. The concave groove is a cubic space or an angled space. The depth of the concave groove can be, e.g., from 10 nm to 1 mm, and the channel width can be, e.g., from 1 nm to 1 mm.

FIG. 27 illustrated an apparatus of this invention with a stepped channel 2710. When a biological subject 2701 passes through the channel 2710, probe couples of different distances can be used to measure different microscopic properties, or even the same microscopic at different sensitivity at various steps (2720, 2730, 2740) with probe aside each step. This mechanism can be used in the phase lock-in application so that signal for the same microscopic property can be accumulated. The probes can detect or measure microscopic electric, magnetic, electromagnetic, thermal, optical, acoustical, biological, chemical, physical, or mechanical properties.

FIG. 28 illustrates another apparatus of this invention with thermal meters 2830. It includes a channel, a set of probes 2820, and a set of thermal meters 2830. The thermal meters 2830 can be an infrared sensor, a transistor sub-threshold leakage current tester, or thermister.

FIG. 29 illustrates a specific apparatus of this invention which includes carbon a nano-tube 2920 with a channel 2910 inside, probes 2940 which can detect microscopic electric, magnetic, electromagnetic, thermal, optical, acoustical, biological, chemical, physical, or mechanical properties. The carbon nano-tube 2920 as shown contains a double-helix DNA molecule 2930. The carbon nano-tube can force and sense electrical signals by the probes 2940 aside. The diameter of the carbon nano tube diameter can be, e.g., from 0.5 nm to 50 nm, and its length can range from, e.g., 5 nm to 10 mm FIG. 30 shows an integrated apparatus of this invention that includes a detecting device (shown in FIG. 30(a)) and an optical sensor (shown in FIG. 30(b)) which can be, e.g., a CMOS image sensor (CIS), a Charge-Coupled Device (CCD), a florescence light detector, or another image sensor. The detecting device comprises at least a probe and a channel, and the image device comprises at least 1 pixel. FIG. 30(c-1) and FIG. 30(c-2) illustrate the device with the detecting device and optical sensor integrated. As illustrated in FIG. 30(d), when biological subjects 3001, 3002, 3003 pass through, the probe 3010 in the channel 3020, its electric, magnetic, electromagnetic, thermal, optical, acoustical, biological, chemical, physical, or mechanical property could be detected by the probe 3010 (see FIG. 30(e)), meanwhile its image could be synchronously recorded by the optical sensor (FIG. 30(f)). Both the probed signal and image are combined together to provide a diagnosis and enhanced detection sensitivity and specificity. Such a detecting device and an optical sensing device can be designed in a system-on-chip or be packaged into one chip.

FIG. 31 shows an apparatus with a detecting micro-device (FIG. 31(a)) and a logic circuitry (FIG. 31(b)). The detecting device comprises at least a probe and a channel, and the logic circuitry comprises an addresser, an amplifier, and a RAM. When a biological subject 3101 passes through the channel, its property could be detected by the probe 3130, and the signal can be addressed, analyzed, stored, processed, and plotted in real time. FIG. 31(c-1) and FIG. 31(c-2) illustrate the device with detecting device and Circuitry integrated. Similarly, the detecting device and the integrated circuit can be designed in a System-on-Chip or be packaged into one chip.

FIG. 32 shows an apparatus of this invention that comprises a detecting device (FIG. 32(a)) and a filter (FIG. 32(b)). When a biological subject 3201 passes through the device, a filtration is performed in the filter, and irrelevant objects can be removed. The remaining subjects' property can then be detected by the probe device (FIG. 31(a)). The filtration before probing will enhance the precision of the device. The width of the channel can also range, e.g., from 1 nm to 1 mm.

FIG. 33 shows the geometric factors of DNA 3330 such as spacing in DNA's minor groove (3310) have an impact on spatial distribution of electrostatic properties in the region, which in turn may impact local biochemical or chemical reactions in the segment of this DNA. By probing, measuring, and modifying spatial properties of DNA (such as the spacing of minor groove) using the disclosed detector and probe 3320, one may detect properties such as defect of DNA, predict reaction/process at the segment of the DNA, and repair or manipulate geometric properties and therefore spatial distribution of electrostatic field/charge, impacting biochemical or chemical reaction at the segment of the DNA. For example, tip 3320 can be used to physically increase spacing of minor groove 3310.

FIG. 34 shows the fabrication process for a micro-device of this invention that has a flat cover atop of trench to form a channel. This will eliminate the need for couple two trenches to form a channel, which can be tedious for requiring perfect alignment.

The cover can be transparent and allow observation with a microscope. It can comprise or be made of silicon, SiGe, $SiO_2$, or $Al_2O_3$.

While for the purposes of demonstration and illustration, the above cited novel, detailed examples show how microelectronics or nano-fabrication techniques and associated process flows can be utilized to fabricate highly sensitive, multi-functional, powerful, and miniaturized detection devices, the principle and general approaches of employing microelectronics and nano-fabrication technologies in the design and fabrication of high performance detection devices have been contemplated and taught, which can and should be expanded to various combination of fabrication processes including but not limited to thin film deposition, patterning (lithography and etch), planarization (including chemical mechanical polishing), ion implantation, diffusion, cleaning, various materials, combination of processes and steps, and various process sequences and flows. For example, in alternative detection device design and fabrication process flows, the number of materials involved can be fewer than or exceed four materials (which have been utilized in the above example), and the number of process steps can be fewer or more than those demonstrated process sequences, depending on specific needs and performance targets. For example, in some CTC detection applications, a fifth material such as a biomaterial-based thin film can be used to coat a metal detection tip to enhance contact between the detection tip and a biological entity being measured, thereby improving measurement sensitivity.

Applications for the detection apparatus and methods of this invention include detection of cancers (e.g., in their early stage). Since cancer cell and normal cell differ in a number of ways including differences in possible microscopic properties such as electrical potential, surface charge, density, adhesion, and pH, novel micro-devices disclosed herein are capable of detecting these differences and therefore applicable for enhanced capability to detect cancer, particularly in their early stage. In addition micro-devices for measuring electrical potential and electrical charge parameters, micro-devices capable of carrying out mechanical property measurements (e.g., density) can also be fabricated and used as disclosed herein. In mechanical property measurement for early stage cancer detection, the focus will be on the mechanical properties that likely differentiate circulating tumor cells from normal cells. As an example, one can differentiate circulating tumor cells from normal cells by using a detection apparatus of this invention that is integrated with micro-devices capable of carrying out micro-indentation measurements.

FIG. 35 is a diagram of an apparatus of this invention for detecting a disease in a biological subject. This apparatus includes a pre-processing unit, a probing and detecting unit, a signal processing, and a disposal processing unit.

FIG. 36 shows an example of a sample filtration sub-unit in the pre-processing unit, which can separate the cells with different dimensions or sizes. This device comprises at least one entrance channel 3610, one disturbing fluid channel 3620, one accelerating chamber 3630, and two selecting channels (3640 and 3650). The angle 3660 between 3620 and 3610 ranges from 0° to 180°.

The biological subject 3601 flows in the x direction from the entrance channel 3610 to the accelerating chamber 3630. A bio-compatible fluid 3602 flows from disturbing fluid channel 3620 to the accelerating chamber 3630, it then accelerates the biological subject 3601 in the y-direction. The acceleration correlates with the radius of the biological subject and the larger ones are less accelerated than the smaller ones. Then, the larger and smaller subjects are separated into different selecting channels. Meanwhile, probes can be optionally assembled on the sidewalls of the channels 3610, 3620, 3630, 3640, and 3650. The probes could detect, at the microscopic level, electric, magnetic, electromagnetic, thermal, optical, acoustical, biological, chemical, biochemical, electro-mechanical, electro-chemical, electro-chemical-mechanical, physical, or mechanical properties.

FIG. 37 is a diagram of another example of a sample filtration unit in the apparatus of this invention. 3701 represents small cells, while 3702 represents large cells. When a valve 3704 is open and another valve 3703 is closed, biological subjects (3701 and 3702) flow towards exit A. Large cells that have larger size than the filtration hole are blocked against exit A, while small cells are flushed out through exit A. The entrance valve 3704 and exit A valve 3707 are then closed, and a bio-compatible fluid is injected through the fluid entrance valve 3706. The fluid carries big cells are flushed out from exit B. The larger cells are then analyzed and detected in the detection part of the invention.

FIG. 38 is a diagram of a pre-processing unit of an apparatus of this invention. This unit includes a sample filtration unit, a recharging unit or system for recharging nutrient or gas into the biological subject, a constant pressure delivery unit, and a sample pre-probing disturbing unit.

FIG. 39 is a diagram of an information or signal processing unit of an apparatus of this invention. This unit includes an amplifier (such as a lock-in amplifier) for amplifying the signal, an A/D converter, and a micro-computer (e.g., a device containing a computer chip or information processing sub-device), a manipulator, a display, and network connections.

FIG. 40 shows the integration of multiple signals which results in cancellation of noise and enhancement of signal/noise ratio. In this figure, a biological 4001 is tested by Probe 1 during Δt between t1 and t2, and by Probe 2 during Δt between t3 and t4. 4002 is 4001's tested signal from Probe 1, and 4003 is from Probe 2. Signal 4004 is the integration result from signal 4002 and 4003. The noise cancels out each other in certain extent and results in an improved signal strength or signal/noise ratio. The same principle can be applied to data collected from more than more than 2 micro-devices or probing units.

The micro-devices described herein, as well as some of the detection parameters and properties and processes described herein, have been used for tests on cancerous samples (e.g., liver cancer samples and breast cancer samples) and controls (i.e., noncancerous or normal samples). While these samples were not CTC samples, the tests nonetheless were relevant to this invention and indicative of the invention claimed herein as they showed advantages and improvements (for example, improved signal sensitivity) in cancer detection which will be very beneficial for CTC detections. Further, these tests have proved the concept of enhancing cancer detection signals and efficiency which is very applicable to CTC. In one set of experiments, use of the micro-devices and test parameters described herein resulted in enhanced measurement signal compared to a currently known method based on genomic analysis. Specifically, even after diluting the original cancer cell samples by over 20 times, signals differentiating the cancer cells from the normal sample were still detected. By comparison, a recently reported genomic analysis detected signal of a cancer sample that was diluted only about 5 times. The tested micro-devices, associated testing parameters, cancer and normal cell properties, and testing methodologies described herein have all showed high degree of measurement sensitivity, reliability, and repeatability.

Additional tests were carried out in the laboratory with the micro-devices described herein on certain cancerous tissue samples (with multiple samples for each type of cancer) although the micro-devices can be used for detection of other types of cancer or other types of treatment. In the tests, healthy control samples were obtained from animals with no known cancer disease at the time of collection and no history of malignant disease. Both cancerous samples and healthy control samples were collected and cultured in the same type of culture solution. The cultured samples were then mixed with a dilution buffer and diluted to the same concentration. The diluted samples were maintained at the room temperature for different time intervals and processed within a maximum of 6 hours after being recovered. The diluted samples were tested at the room temperature (20~23° C.) and in the humidity of 30%-40%. The samples were tested with a micro-device of this invention under the same conditions and stimulated by the same pulse signal.

The test results show that, in general, the control groups' tested (measured) values (i.e., measured values in relative units for the testing parameter) were lower than the cancerous or diseased groups. Under the same stimulation (in terms of stimulation type and level) with a stimulating or probing signal applied by a probing unit of the tested micro-devices, the difference shown in the measured values between the control groups and the cancerous groups became much more significant, e.g., ranging from 1.5 times to almost 8 times in terms of level of increase in such difference, compared with that without simulation. In other words, the cancerous groups' response to the stimulating signal was much higher than that of the control groups. Thus, the tested micro-devices have been proven to be able to significantly enhance the relative sensitivity and specificity in the detection and measurement of diseased cells, in comparison to the control or healthy cells.

Further, the test results show that in terms of the novel parameter utilized by the micro-device of this invention, the cancerous group and the control group showed significantly different response. Such difference is significantly greater than the measurement noise. There was a large window to separate the control groups from the cancerous groups, showing a high degree of sensitivity of the novel measurement method and apparatus.

Although specific embodiments of this invention have been illustrated herein, it will be appreciated by those skilled in the art that any modifications and variations can be made without departing from the spirit of the invention. The examples and illustrations above are not intended to limit the scope of this invention. Any combination of detection apparatus, micro-devices, fabrication processes, flow sequence, and applications of this invention, along with any obvious their extension or analogs, are within the scope of this invention. Further, it is intended that this invention encompass any arrangement, which is calculated to achieve that same purpose, and all such variations and modifications as fall within the scope of the appended claims.

All publications referred to above are incorporated herein by reference in their entireties. All the features disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example of a generic series of equivalent or similar features.

OTHER EMBODIMENTS

It is to be understood that while the invention has been described in conjunction with the detailed description thereof and accompanying figures, the foregoing description and accompanying figures are only intended to illustrate, and not limit the scope of the invention, which is defined by the scope of the appended claims. Other aspects, advantages, and modifications are within the scope of the following claims. All publications referenced herein are incorporated by reference in their entireties.

What is claimed is:

1. A micro-device comprising a micro-trench, a probe embedded along side the trench's side walls or bottom floor, a supporting structure to move the probe, and a controlling circuitry, wherein the micro-device is capable of trapping, measuring, detecting, sorting, counting, analyzing, modifying, correcting, or communicating circulating tumor cells in a biological subject by measuring a property of the circulating tumor cells at microscopic level; wherein the probe has a tip alongside the trench and the tip matches spatially with either a major groove or a minor groove of DNA.

2. The micro-device of claim 1, wherein the tip matches spatially with interlaced grooves of DNA.

3. The micro-device of claim 2, wherein the groove interval is variable.

4. The micro-device of claim 1, wherein the tip's diameter ranges from about 1 angstrom to about 10 μm.

5. A micro-device comprising a micro-trench, a probe embedded along side the trench's side walls or bottom floor, a supporting structure to move the probe, and a controlling circuitry, wherein the micro-device is capable of trapping, measuring, detecting, sorting, counting, analyzing, modifying, correcting, or communicating circulating tumor cells in a biological subject by measuring a property of the circulating tumor cells at microscopic level; wherein the tip of the probe has a tip at the end of trench and the tip matches the end of each strand of the DNA helix.

* * * * *